United States Patent [19]

Brown, Jr.

[11] Patent Number: 5,387,164
[45] Date of Patent: Feb. 7, 1995

[54] ACTIVITY GUIDEANCE DATA PROCESSING METHOD

[75] Inventor: Richard L. Brown, Jr., Eugene, Oreg.
[73] Assignee: Leap, Incorporated, Eugene, Oreg.
[21] Appl. No.: 793,485
[22] Filed: Nov. 13, 1991

Related U.S. Application Data

[63] Continuation of Ser. No. 404,675, Sep. 8, 1989, abandoned.

[51] Int. Cl.⁶ .............................................. A63B 71/00
[52] U.S. Cl. ...................................... 482/9; 482/8; 482/900; 482/901; 364/413.02; 395/375
[58] Field of Search ................ 482/1, 3, 8, 9, 52, 482/54, 57, 72, 74, 900, 901; 128/75 R, 707; 73/379, 379.01; 434/247; 364/413.02, 413.24; 385/375

[56] References Cited

U.S. PATENT DOCUMENTS

| | | | |
|---|---|---|---|
| 4,283,712 | 8/1981 | Goody | 482/8 X |
| 4,367,752 | 1/1983 | Jimenez et al. | 128/707 X |
| 4,566,461 | 1/1986 | Lubell et al. | 128/707 X |
| 4,642,769 | 2/1987 | Petrofsky | 128/421 X |
| 4,678,182 | 7/1987 | Nakao et al. | 272/129 X |
| 4,790,528 | 12/1988 | Nakao et al. | 272/73 |
| 4,830,021 | 5/1989 | Thornton | 128/707 |
| 4,842,274 | 6/1989 | Oosthuizen et al. | 272/129 |
| 4,882,677 | 11/1989 | Curran | 272/129 X |
| 4,911,427 | 3/1990 | Matsumoto et al. | 272/73 |
| 4,938,475 | 7/1990 | Sargeant et al. | 482/9 |
| 4,998,725 | 3/1991 | Watterson et al. | 482/8 X |
| 5,018,726 | 5/1991 | Yorioka | 482/8 |

OTHER PUBLICATIONS

"Physical Conditioning Equipment", Universal 1981–1982 Catalog.

*Primary Examiner*—Richard J. Apley
*Assistant Examiner*—Joe H. Cheng
*Attorney, Agent, or Firm*—Lieberman & Nowak

[57] ABSTRACT

A system, method and kit for scheduling, monitoring and improving physical exercise is provided. These goals are achieved by the use of a hand-held computer for programming the inputs of activity, individual parameters and environmental conditions; a user's manual having instructions and a diary; a guide book giving access to expert advice; and system of cards providing questions and advice. Data is entered into the computer where it is analyzed. By combining the computer analysis with the user's manual, guidebook and cards, the benefits of a personal fitness trainer are obtained.

1 Claim, 78 Drawing Sheets

Coef. of Activity

| | | |
|---|---|---|
| Aerobics .85 | Football (touch) .68 | Shuffleboard .24 |
| Bicycle 1.00 | *Frisbee* .44 | Skate (ice) .58 |
| Run/Jog 1.00 | *Frisbee* (ultimate) .75 | Skate (roller) .58 |
| Swim 1.00 | Gardening .52 | Skateboard .62 |
| Walk .95 | Golf (cart) .27 | Ski (cross-country) 1.05 |
| Wheelchair .93 | Golf (walk) .45 | Ski (downhill) .65 |
| *AirDyne* 1.05 | Gymnastics .72 | Ski (water) .57 |
| Archery .36 | Handball .78 | Snorkle .56 |
| Badminton .73 | Horseback Riding .50 | Snowshoe 1.15 |
| Backpack .68 | Horseshoes .26 | Soccer .80 |
| Ballet .82 | Housework .40 | Softball .45 |
| Ballet .82 | Hunting .58 | Softball (pitch/catch) .58 |
| Baseball .47 | Ice Hockey .80 | Squash .78 |
| Baseball (pitch/catch) .60 | Judo, Etc. .95 | Stair Climbing .85 |
| Basketball .82 | Jump Rope .78 | Table Tennis .41 |
| Basketball (shooting) .57 | Kayak .75 | Tennis .76 |
| Bed Exercise .22 | Lacrosse .80 | Treadmill .97 |
| Bicycle (stationery) | Manual Labor .61 | Volleyball .76 |
| Billiards .23 | Minitramp .71 | Water Aerobics (deep) .75 |
| Boating .39 | *NordicTrack* 1.10 | Water Aerobics (power) .82 |
| Bowling .34 | Paddleball .78 | Water Aerobics (shallow) .50 |
| Boxing .95 | Racewalking 1.08 | Weight Training .71 |
| Calisthenics .71 | Racquetball .78 | Weight Training (power) .67 |
| Canoeing .70 | Rowing (boat) .70 | Wheelchair Activities .73 |
| Circuit Training .71 | Rowing (machine) .90 | Wrestling .95 |
| Climbing .81 | Rowing (shell) .95 | Yachting .63 |
| Croquet .25 | Rugby .80 | Yoga .51 |
| Dancing .54 | Run-in-place .77 | |
| Fencing .76 | Run-in-$H_2O$ (bottom) .55 | |
| Field Hockey .80 | Run-in-$H_2O$ (deep) .83 | |
| Fishing (bank, boat) .33 | Sailing .48 | |
| Fishing (wade, ocean) .53 | Skin/Scuba Dive .69 | |
| Football (tackle) .70 | Shooting .35 | |

FIG. 8(g)

ACTIVITY GUIDEANCE DATA PROCESSING METHOD

This is a continuation of application Ser. No. 404,675, filed Sep. 8, 1989, now abandoned.

FIELD OF THE INVENTION

The present invention relates to activity or exercise guidance and the creation and maintenance of a personal exercise regime that accounts for the personal history, goals, activities and abilities of the individual exerciser, and provides recommended activities equivalent to that of a personal coach.

BACKGROUND OF THE INVENTION

Today's consumer possesses a growing interest in the benefits of regular activity, including increased energy, enhanced appearance and general feeling of well-being. More people are devoting greater amounts of time and resources to pursuing effective activity programs, geared to individual exercise needs and history.

For example, people join health clubs and then discover that the group environment is more social than productive and more stifling or pressured. Health clubs generally report higher numbers of new members around the December holiday season gradually tapering off in mid-winter as even the new members stop attending. The reasons are often related to overtraining at the outset, and resultant pain, impeding the desire to return to the spa. Health spa members thus rarely maintain a consistent exercise program.

There are a great many products that have been introduced in response to the growing need for an all inclusive, well balanced program, including complex home exercise equipment, software, books, magazines, cassettes and videotapes, and there is an increase in companies that purport to provide health assessment profiles, nutritional and dietary guidance, and even, private coaches or physiologists.

Larry Cuzzort, a fourth place finisher in the 1982 TAC Cross Country Championship at Penn State developed a computer program to account for his runs over a period of time, including weather conditions, types of terrain and other variables. Similar programs have been developed by others, including Jim Fixx's "The Running Program" which is billed as a personalized running guide for developing daily training programs. Other such programs are provided by Computer Services, Homesoft, Inc., Runsoft and the Running Coach. A tennis program is available through PC Computennis, a swimming program through Peak Performance, aerobics program from Meca, a weight lifting program from AMTI Biomechanics and a cycling program from Game Plan. Similarly, Dr. Francois Peronnet and Guy Thibault developed a large, self-contained running computer called "Hermann" which requires the intervention of its creators for the development of an individual-specific training program.

However, these programs suffer drawbacks, including a limitation to generally one activity, and a hardware (personal computer) requirement to run the software (Hermann even requires its own, large personal computer). Though some software programs profess to account for more than one activity, and there is a Borg-/Nobel chart for perceived exertion, there are presently no systems that are presented in kit form, simple and handheld, supplying a full process for exercise, i.e. accounting for all exercises and activities, geared to the specific individual user's parameters, including the affects of environment (temperature, ground or terrain conditions, etc.), and providing access to a team of expert physicians and coaches who can impart their special knowledge and skill.

SUMMARY OF THE INVENTION

It is an object of the present invention to provide the interaction, daily supervision, feedback, and personal attention provided by a good coach through a kit embodying a comprehensive activity guidance process and system.

It is another object of the present invention to provide means and a method to receive, analyze and display various aspects of an individual's activity patterns accounting for the individual's specific handicaps and abilities, and offering a select and variable array of activities.

It is another object of the present invention to establish a user profile and activity pattern with periodic daily or weekly feedback and modification capability for long-term exercise accounting, interaction and recommended enhancement.

It is yet a further object of the present invention to provide an aerobic system that is capable of use by a host of people from athlete to invalid, adult to child.

It is a still further object of the present invention to provide activity guidance that assists in preventing injury and offers a warning when weekly limits are achieved, or stress indicators are high or abnormal.

These and other objects of the invention are achieved by the provision of a system, method and kit for activity guidance comprising four basic components: (1) a hand-held computer for initial personalized programming and for periodic dynamic input and feedback based on three variables: activity (via an activity point system), individual parameters and environmental conditions of each exercise; (2) a user's manual containing instructions and a diary; (3) a guide book giving access to experts in various exercise related fields; and (4) a system of cards allowing physician, support, warranty and questions.

It is thus a feature of the invention to provide a complete exercise guidance system and kit that encompasses the plurality of exercises that its user is involved in on a daily basis, and awards points for each through a complex analysis, in a concise and user friendly way.

It is a feature of this invention to provide a kit that gives access to a panel of experts in various disciplines and the ability to receive guidance, monitoring and support.

It is a feature of this invention to provide a kit that has a training diary, instruction sheet, a hand-held computer, and a book about the fundamentals of activity by peer-respected professionals.

It is a still further feature of this book to provide an activity guidance system and kit that can be used as a coach or advisor, with a coach, or with a person's existing training program.

It is still further feature of the invention to provide a system that can be used and account for all rhythmical endurance activities and for most sports.

It is yet a further feature of the invention to provide an activity guidance system and kit that can be used by high-level athletes training for competition, by people who desire to push closer to their individual frontiers, and especially, by those of any age who desire activity.

BRIEF DESCRIPTION OF THE DRAWINGS

FIGS. 8(b) through 8(i) are flow charts of the Starting Point, Section 5;

DETAILED DESCRIPTION OF THE INVENTION

Figure 1:
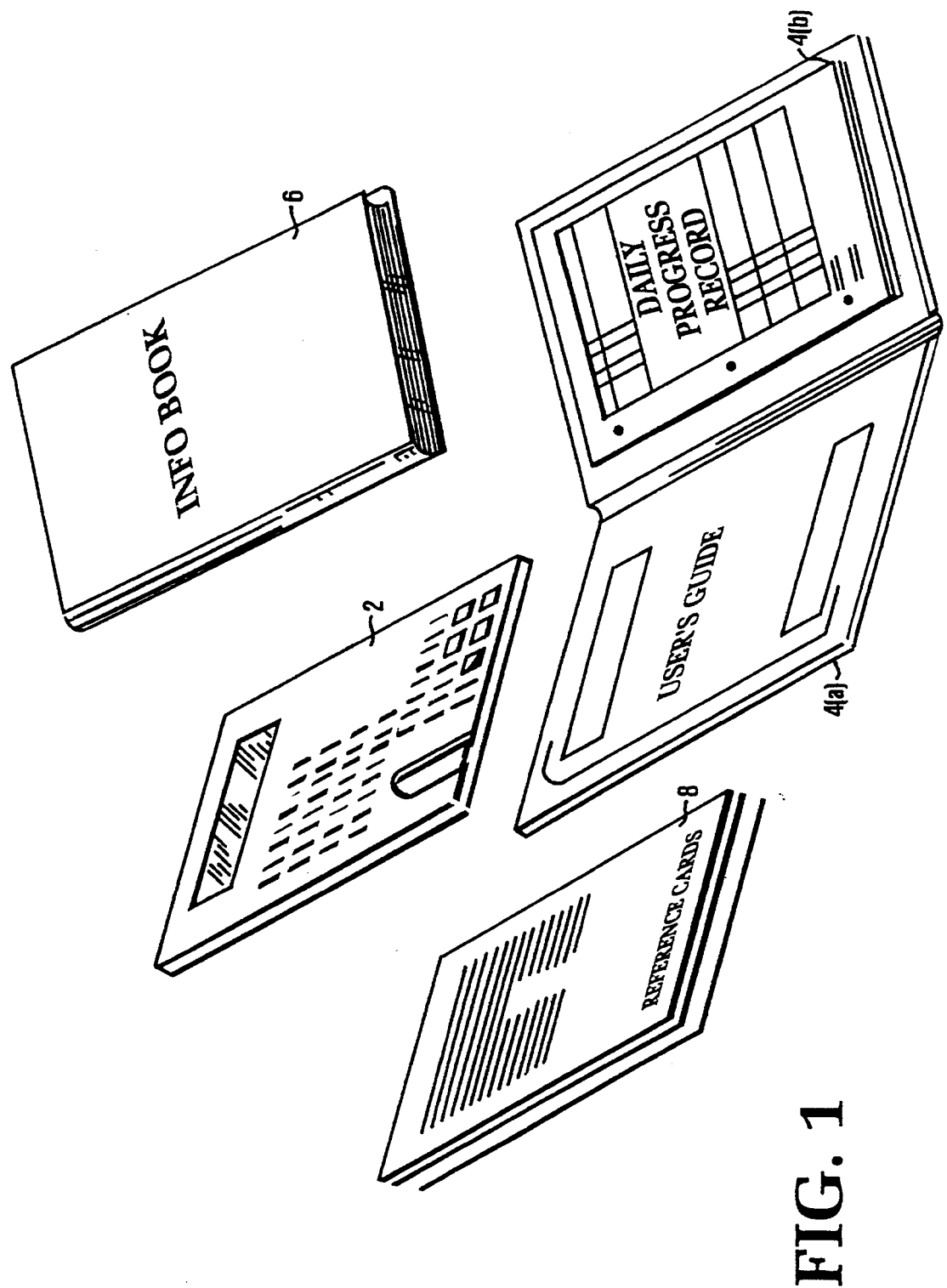
FIG. 1 is an overview of kit components.

FIG. 1 shows the four major components of the activity guidance kit. The kit contains a handheld computer 2, the user's guide 4(a) and daily progress record 4(b), the information book 6, and the reference cards 8. Handheld computer 2 functions like a personal fitness trainer, coach or exercise physiologist, by going through several steps outlined in detail below.

Generally the handheld computer is designed to reside on a desk or table, to be used for a period of approximately 15 to 20 minutes for the first use and then as little as 1 to 2 minutes each day thereafter, and generally will, via the resident software: conduct an in-depth personal interview, evaluate the current fitness level of the user, recommend a realistic exercise starting point, develop a schedule of weekly goals and allow the person to monitor the maintenance of the program. The heart of the system is a daily activity input predicated upon the use of three variables: the individual, the activity (from which there are ninety to choose from), and the environment. Likewise, the handheld computer will access recovery periods, compare daily efforts to weekly goals, and redefine the schedule if weekly goals are met (that is sufficient exercise for the week), or not met (that is insufficient activity for the period). The handheld computer 2 will record approximately 3,000 activity sessions. The specific functionality and identification of the preferred resident software are more further defined below.

As shown in FIG. 1, user's guide 4(a) and daily progress record 4(b) are the second critical components of the activity guidance kit. User's guide 4(a) provides detailed information in user-accessible format for the background and use of the handheld computer 2, and all other aspects of the kit. Daily progress record 4(b) is, as its name implies, a diary for general entry of information relating to the exercise of the user. Information book 6 contains various information and articles written by a number of key exercise doctors, Ph.D's and the like, with information on methodologies for exercise, nutrition and weight control, avoidance of injuries, recovery from injuries, training, relaxing, and the like.

Reference cards 8 include cards providing physicians information with respect to the system and a toll free support phone number for the purposes of receiving and giving information, guarantee cards, and question and answer cards which offer the user the ability to write in information request, send them to the company, and receive responses.

Figure 2:
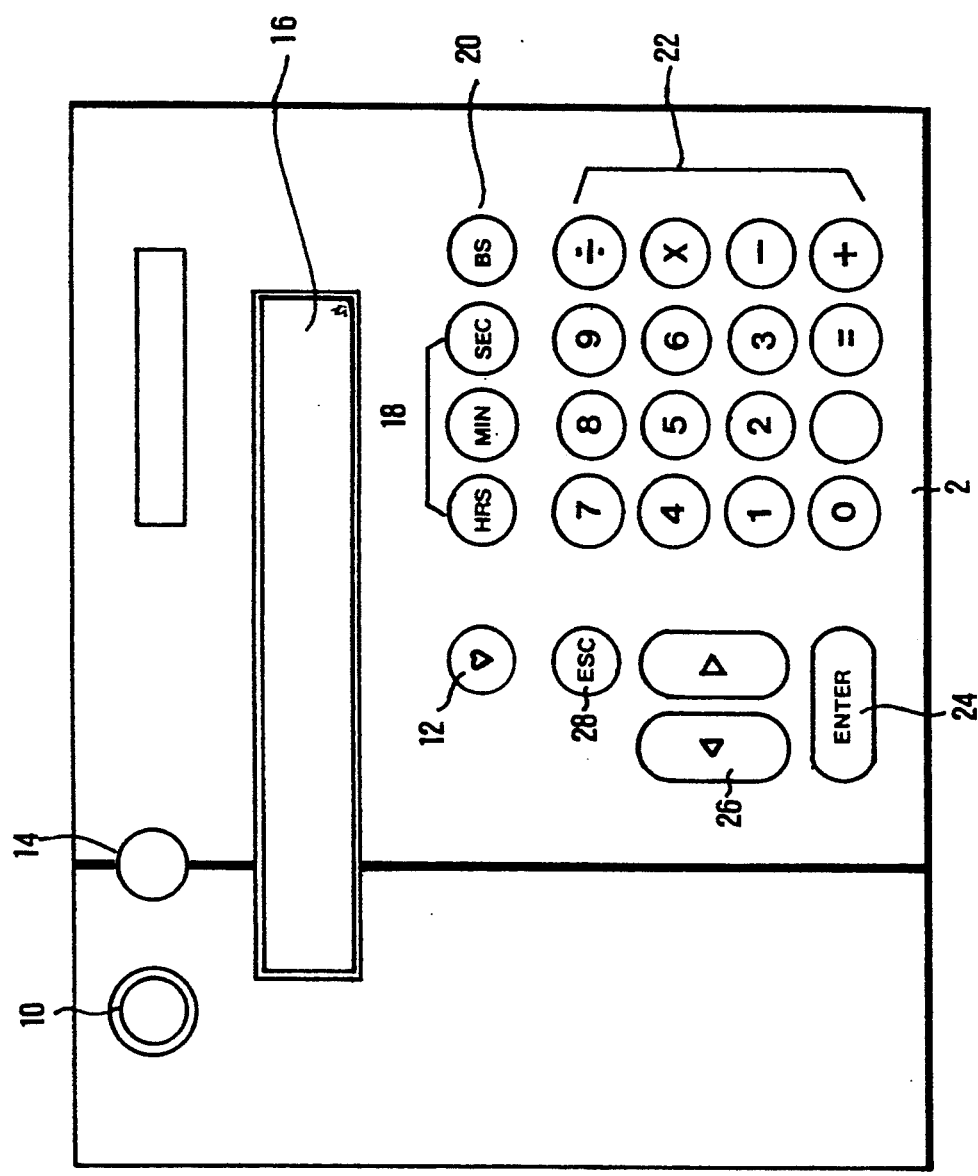
FIG. 2 is a front facial view of handheld computer 2.

FIG. 2 shows the front facial view of handheld personal computer 2. Handheld computer 2 contains a multi-character alphanumeric display 16 to prompt the user for function selection or data entry, report data entry errors, and display results of computations. On/off button 10 is pressed to turn the handheld computer 2 on and off. Heart rate timing light 14 is used in conjunction with heart button 12 for the purposes of determining heart rate. After pressing heart button 12, the light 14 is engaged and lights and the user counts for the duration of the period that the light is on and then multiplies by a factor to determined the heart rate. Heart rate is a piece of the information later to be entered via keyboard 22 and duration input switches 18 for purposes of computing the activity indicators, as further defined below. Handheld computer 2 also possesses an escape key 28 to move between program levels, cursor control 26, to move the cursor on the screen 16, entry button 24 to enter information or to reach a specific program level, and backspace button 20. The computer 2 includes a controller which coordinates the operation and includes RAM which stores data regarding the user's fitness level and expected performance, and ROM which stores the algorithms and operating software. The controller is implemented using a microcontroller chip. Hardware in the controller is used to assist in its operations.

Figure 3:
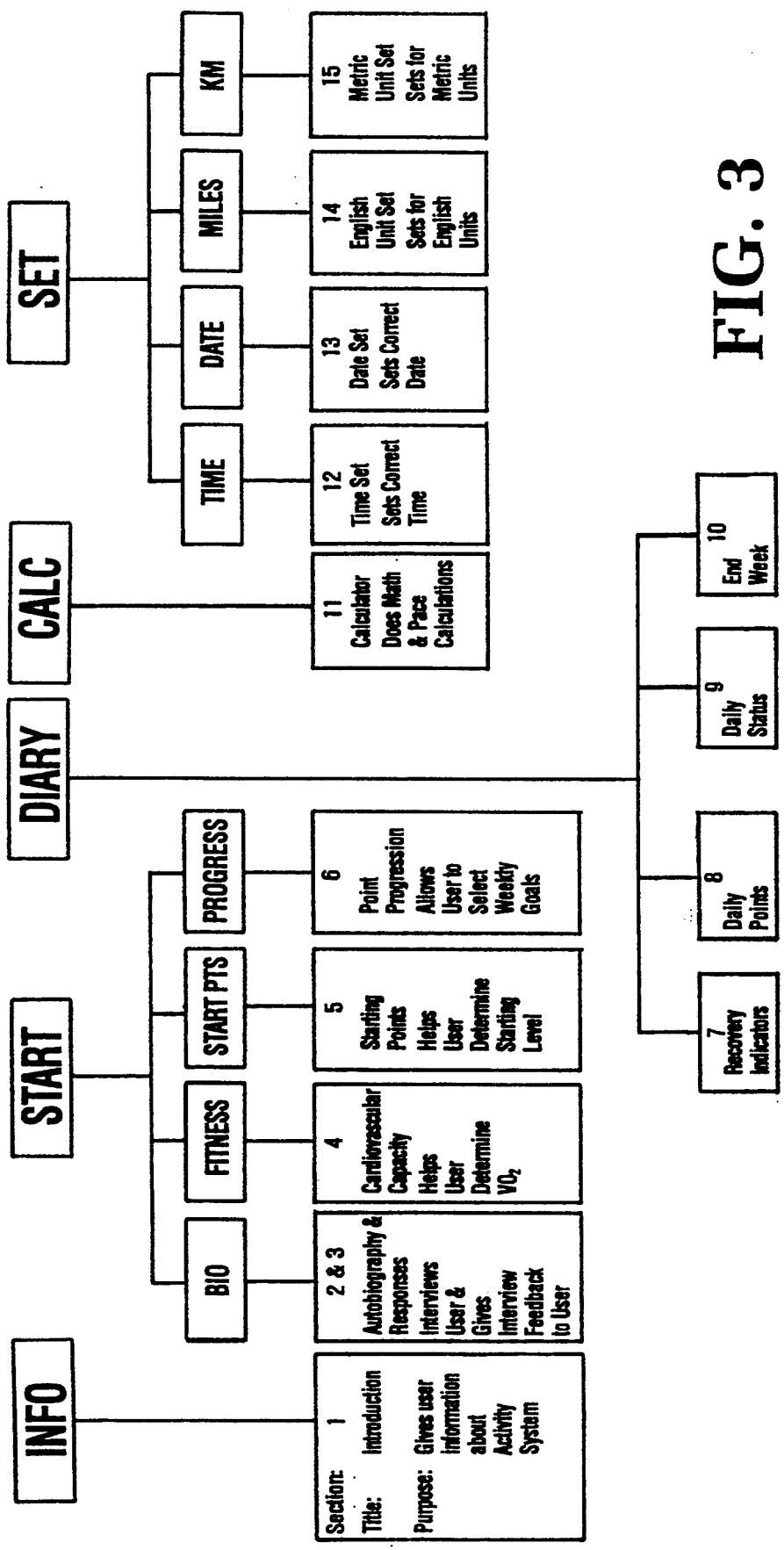
FIG. 3 is a complete system diagram.

FIG. 3 sets forth a general overview and summary of the preferred embodiment of the software resident in the handheld computer 2. The first time the user turns on the computer via On/Off switch 10, screen 16 sets forth the five categories 29 shown on FIG. 3: information 30, start 32, diary 34, calculator 36 and set 38. Generally, information 30, called Section 1 on FIG. 3, is the user information about the activity system and kit. Start 32 is used to initialize the user's current fitness level and, if entered, reveals four categories 41 on the display 16:

bio 40 which is autobiography Sections 2 and 3, fitness 42 which is for cardiovascular capacity, starting point 44 to assist the user in determining the starting level for activity, and progress 46 which includes a point progression allowing the user to select weekly goals. Fitness 42 is referred to as Section 4 (FIGS. 7(d) through (m)), Starting Points 44 as Section 5 (FIGS. 8(a) through(i)) and, Progress 46 as Section 6 (FIG. 9 (a) through (c)).

Diary 34 constitutes the daily or periodic entry system which utilizes the information produced in start 32 and assists the user in developing and following an exercise regime. Diary 34 has four components. First are recovery indicators 48, called Section 7 (FIGS. 10(a) through (c)) which help the user determine the period for recovery, a necessary ingredient in good exercise. Most prior art devices generally tend not to provide sufficient opportunity for recovery, which, I have discovered, is a critical ingredient in proper exercise. Diary 34 further includes a daily points 50, called Section 8 (FIGS. 11(a) through 11(k)), which computes the efforts of activity constituting a reflection of the day's total activity effort stored and compared with the weekly goal points. Diary 34 also includes daily status 52, Section 9 (FIGS. 12(a) through (f)) for computing the current status of the user comparing daily points against weekly goals, and end of week 54, Section 10 for computing the weekly totals and setting the goals for the following week. Each of these will be described below.

As shown in FIG. 3, calculator 36 is also provided, called Section 11 (see FIG. 14), for standard calculating functions via key pad 22 in FIG. 2. Calculator 36 can be used for purposes of performing pace calculations, or, for that matter, any other simple math.

Set 38 in FIG. 3 functions to allow the user to set various aspects of the computer 2, and if entered, display 16 will show four categories 61: time 56, date 58, miles 60 and kilometers 62. Time 56 and date 58 are utilized for purposes of setting the correct time and date, respectively, via key pad 22. Miles 60 indicates distances in english units, and kilometers 62 in metric units.

Figure 4A:
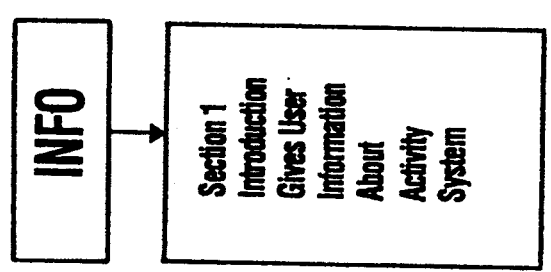
FIG. 4(a) is an overview of the Information, Section 1 of the resident software.
Figure 4B:
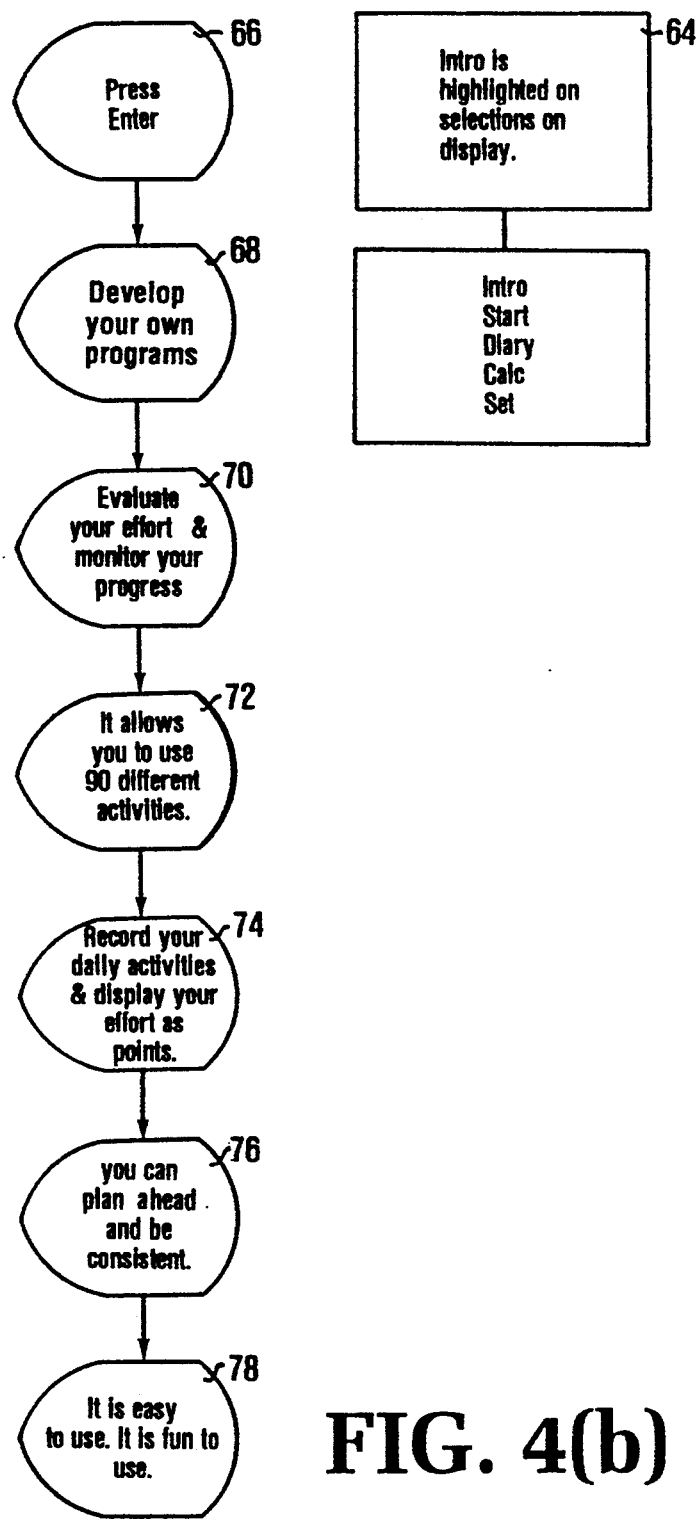
FIG. 4(b) is a flow chart of the Introduction (also called Information), Section 1 of the resident software.

When the user turns on the handheld computer 2 via on/off switch 10 (see FIG. 2) and sees the five categories 29 displayed on the screen (info 30, start 32, diary 34, calculator 36 and set 38, FIG. 3) he may move the cursor from one of the five to another of the five via cursor movement keys 26 (FIG. 2). For the first use of the machine, the user starts on the start entry 32. Should the user choose info 30, he will enter a general introductory section, as shown on FIGS. 4(a) and 4(b). As shown in FIG. 4(b), box 64 repeats the general screen 29 when the system is turned on, and provides access to introduction/information 30, via highlighting or underlining on the display 16 of intro 30. Screens 66 through 78 set forth the information listed under the preferred embodiment for the introductory section. It is to be understood that this information may be modified or expanded upon in other and further ways, without deviating from the scope of the invention herein. The primary function of the introduction section is to give general background information and assistance ("help") to the user of the activity guidance program, process, system and kit.

Via escape button 28, if the user has entered info 30, he may move back to the first screen 29, giving the opportunity to move the cursor from info 30 to start 32.

As stated above, start 32 is entered to initialize the system, that is to set its parameters properly and specifically to reflect the user's individual characteristics and parameters. After initializing the system through start 32, the user may access diary 34, calculator 36 or set 38.

Figure 5A:
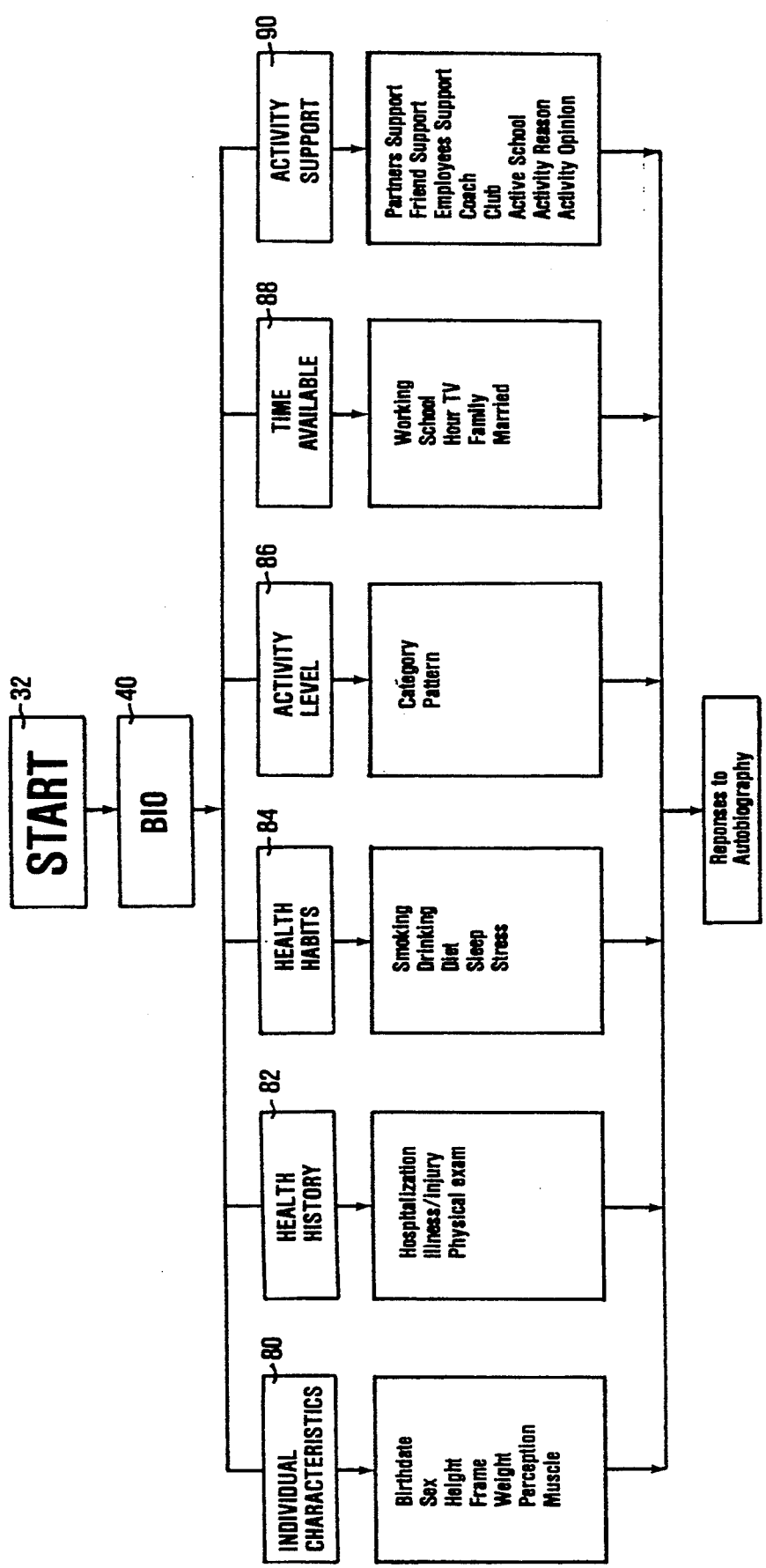
FIG. 5(a) is an overview of the Autobiography, Section 2 of the resident software.

When start 32 is entered on screen 29, and bio 40 is in turn entered, the user will see the six selections set forth in FIG. 5(a), the flow charts of which are set forth on FIGS. 5(b) through 5(j).

When autobiography 40 is entered, an indication is first given as to the percentage of completion of the autobiography. If complete, the user will be so informed and directed to diary 34. If incomplete the user will proceed to complete it. Autobiography 40 accounts for individual characteristics 80, including, sex, height, frame, weight, perception and muscle. Each of these individual characteristics 80 are utilized for the purposes of establishing an activity index to determine what the proper activity patterns will be for the individual, as set forth in further detail below. Another critical element in autobiography is the health history 82, the health habits 84 (smoking, drinking, diet, sleep and stress), the activity level 86, the time available for exercise 88, and the activity support 90. FIGS. 5(b) through 5(j) set forth in specific detail the preferred flow charts for the autobiography 40 set forth in FIG. 5(a).

When the user has completed all of the sub-sections of "bio" 40, Section 2, the user then proceeds to Section 3 responses to autobiography set forth in FIGS. 6.

Figure 5B:
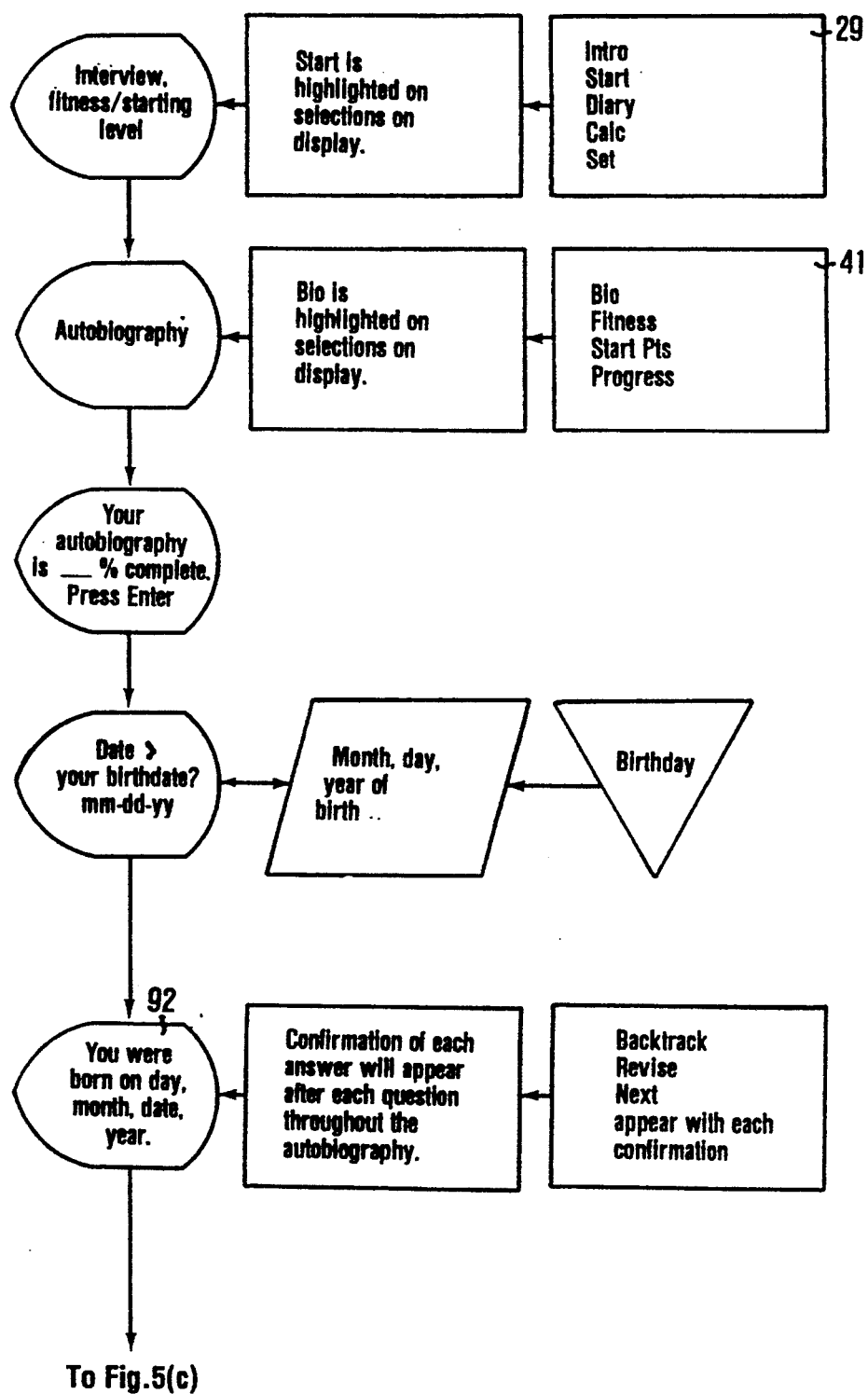
FIGS. 5(b) through 5(m) are flow charts of the Autobiography, Section 2.
Figure 5C:
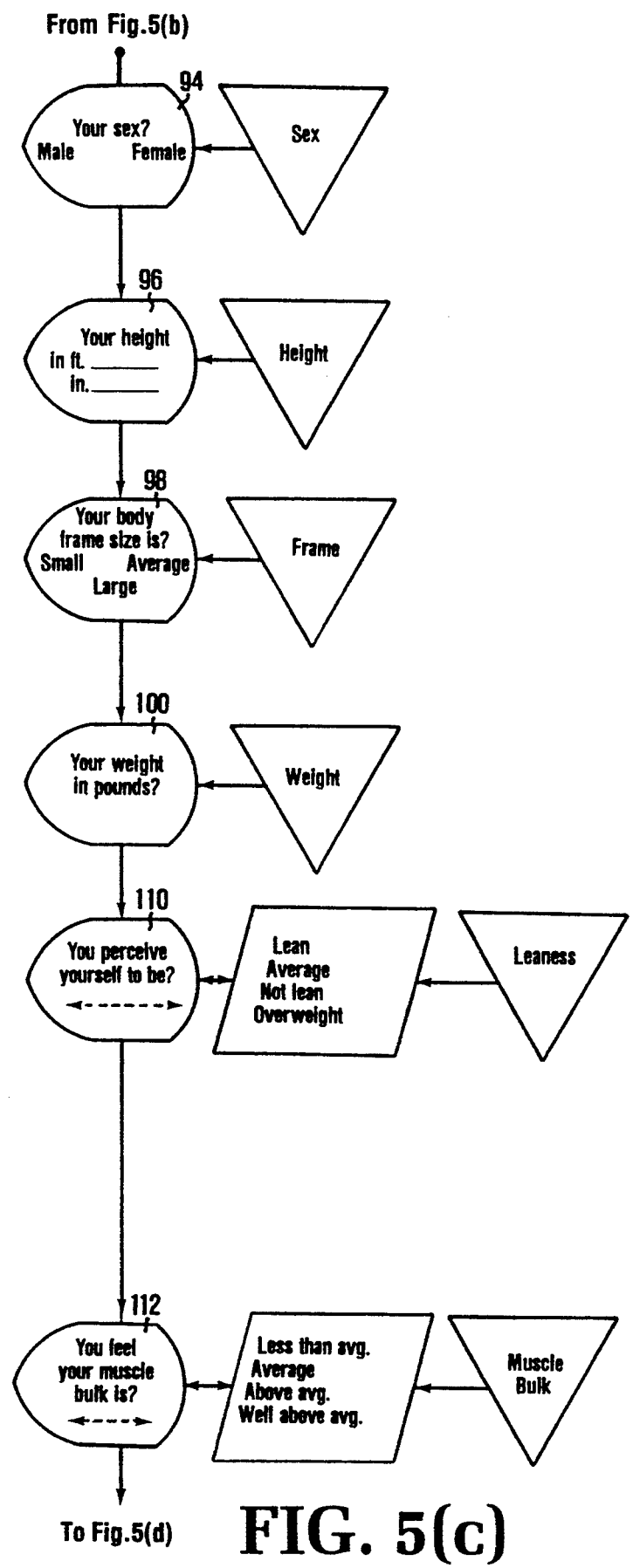
Figure 5D:
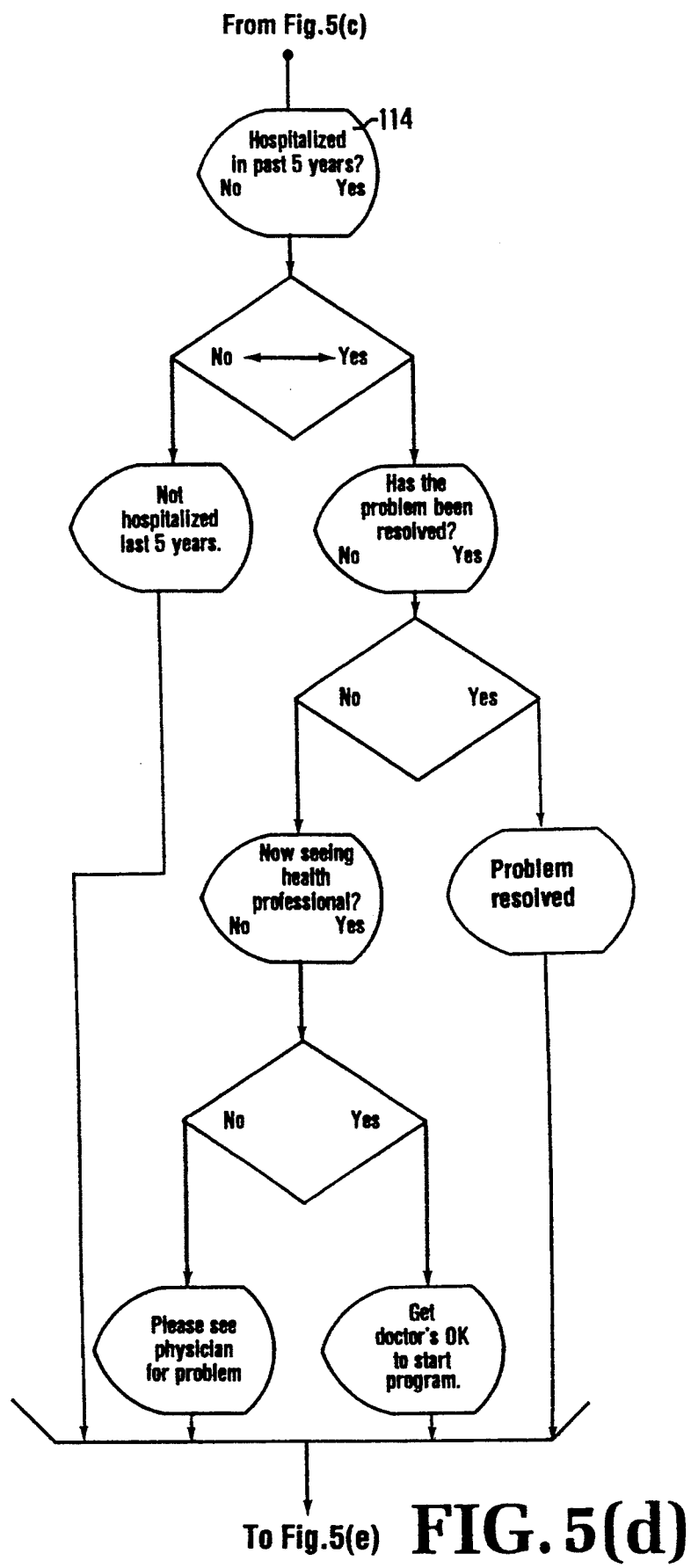

FIGS. 5(b) through 5(j) are the specific preferred flow charts for the autobiography 40. FIG. 5(d) commences with two steps to enter the autobiography 40 showing first screen 29 then screen 41 with the selection of "bio". It must be understood that each of the prompts on the various screens are utilized for purposes of gathering information which are entered in certain select formulas for determining various activity levels and achieving activity points, as set forth in greater detail below. The information gathered through the responses indicated on FIGS. 5(b) through 5(j) are entered in Section 3 responses to autobiography shown in FIG. 6, into the formulas set forth therein.

Screen 92 in FIG. 5(b) requests entry of the birthday of the user. For each question requested in Section 2 autobiography, set forth in FIGS. 5(b), et al., there is a confirmation of each answer appearing after each question. Below the confirmation the cursor aligns with the words "backtrack, revise or next". This allows the user, as the words imply, to either modify a previous answer or to proceed to the next. FIG. 5(c) continues with the request for information with screen 94 requesting the sex of the user, screen 96 requesting the height, screen 98 requesting the body size (small, average or large), screen 100 the user's weight in pounds, screen 110 perception of the user, and screen 112 muscle bulk of the user. Although the system provides guidance, it must be understood that the information provided is subjective, that is, it is the user's own interpretation of himself. The purpose of the exercise is to allow the user to sculpt his own exercise regime in any manner that would be satisfactory for his own perceived abilities and needs. The user does not know what the affect of proper or improper answers will be, and thus is urged by the particular request to provide his own belief of an accurate answer.

Screen 110 concerning perception gives four possible outcomes: lean, average, not lean or overweight. Likewise screen 112 allows four choices for muscle bulk, including less than average, average, above average, or well above average. As shown on these flow charts, the triangle indicates where the information provided proceeds to be processed in the autobiography Section 3, as described in greater detail below.

Figure 5E:
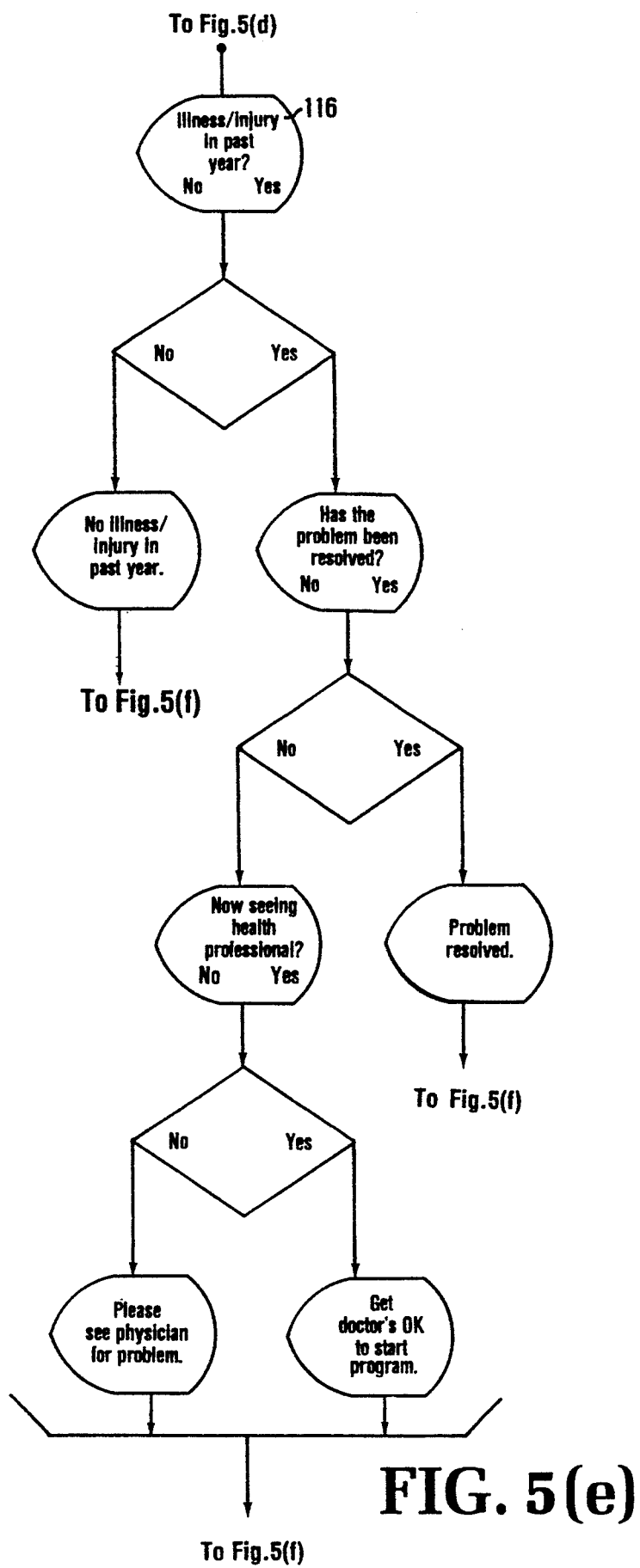
Figure 5F:
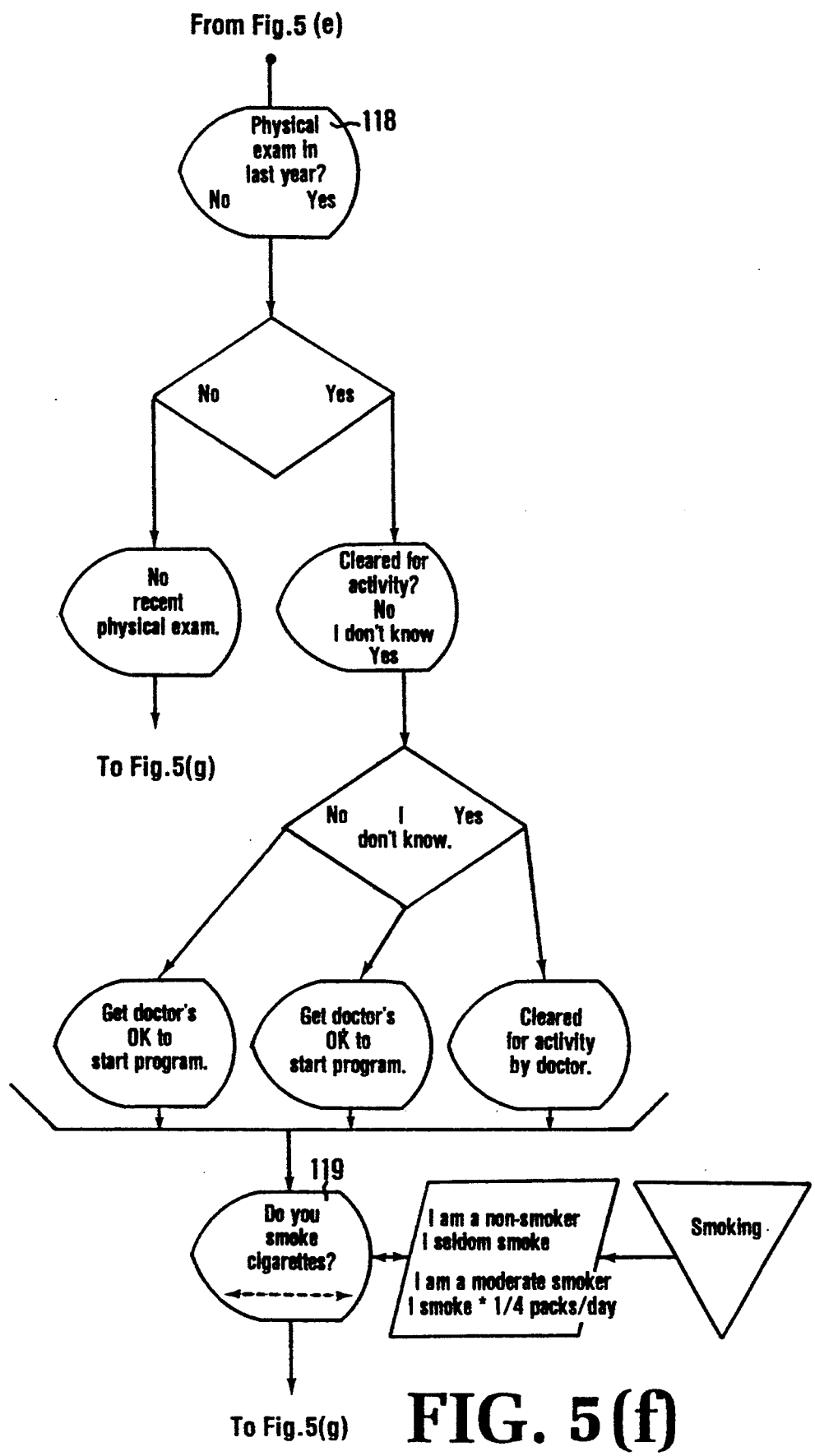

FIGS. 5(d), 5(e) and 5(f) concern the medical status of the user. Again it is critical to have a system set specifically for the user's individual parameters, and thus the user must indicate his medical condition. Screen 114 requests input as to whether the user has been hospitalized in the past five years. If yes, as shown in FIG. 5(d), the user is prompted to answer further questions concerning resolution of the problem, or the continuance of medical treatment. Akin to the qualities a good coach would impart, this information is critical for setting up an exercise regime that will not incur further medical damage. FIG. 5(e) prompts the user to answer screen 116 concerning an illness or injury in the past year. This request is distinct from screen 114 which concerns hospitalization, in probing the present medical condition, by analysis of the previous 12 months. Like FIG. 5(d), 5(e) prompts the user to indicate whether the problem has been resolved or whether the problem is continuing. If the problem is continuing, the user is prompted to get his treating physician's approval before starting the program.

FIG. 5(f), screen 118 seeks to determine whether a physical examination has been conducted in the last 12 months. Again it is critical to determine whether the patient has any hidden medical conditions. If the user has not been cleared for activity, he is prompted to receive doctor's approval before starting the program. FIG. 5(f), screen 119, requests the user to set forth whether he is a smoker or not. Critical to this analysis is the determination of the volume of oxygen ("VO$_2$"), to determine the amount of oxygen that the user has available, or could properly apply to the exercise.

Figure 5G:
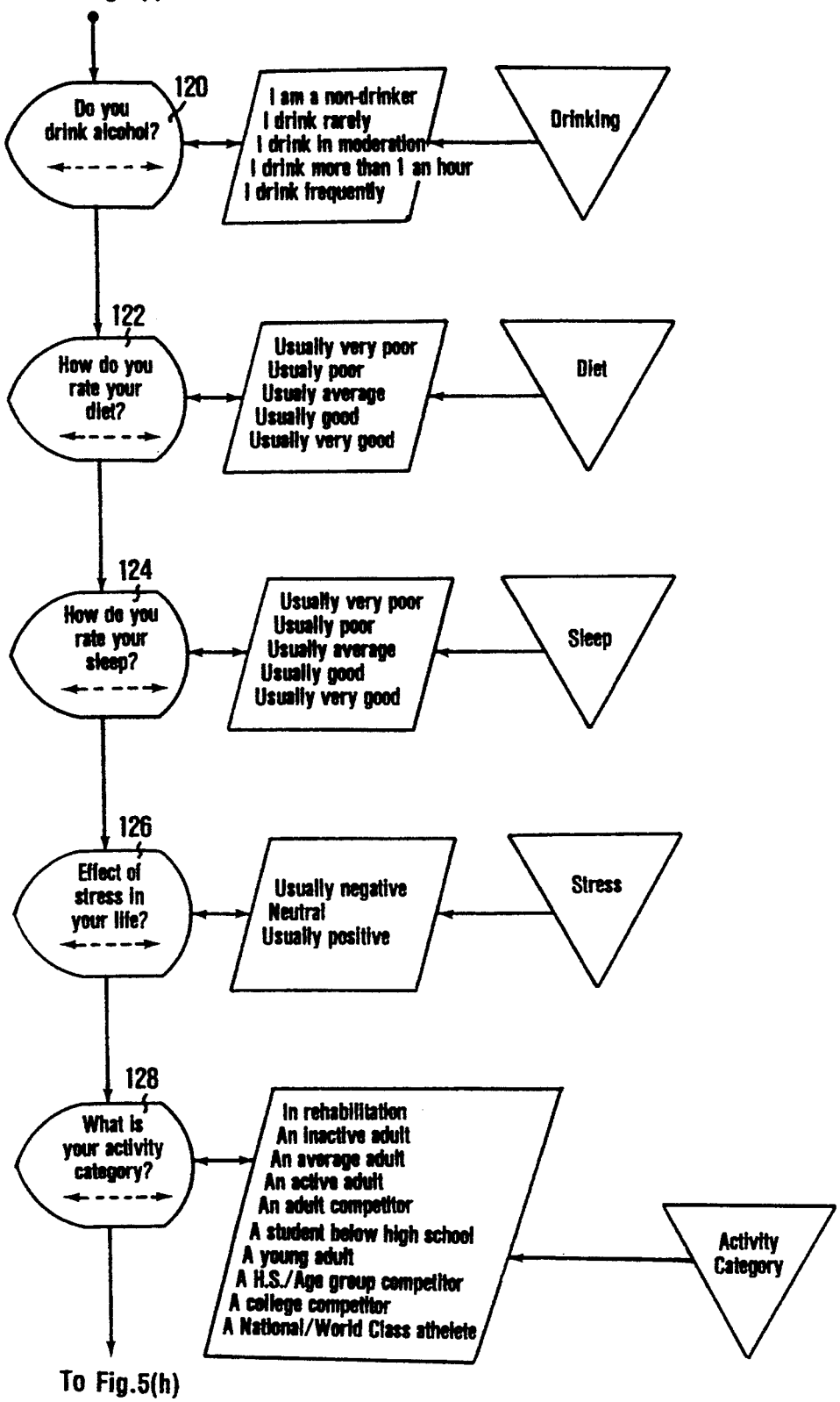

FIG. 5(g) prompts the user to indicate the extent of the user's drinking (screen 120), diet (screen 122), sleep (screen 124), affective stress in the user's life (screen 126), activity category (screen 128). I have discovered that all these factors are critical in properly determining an exercise regime for the user.

Figure 5H:
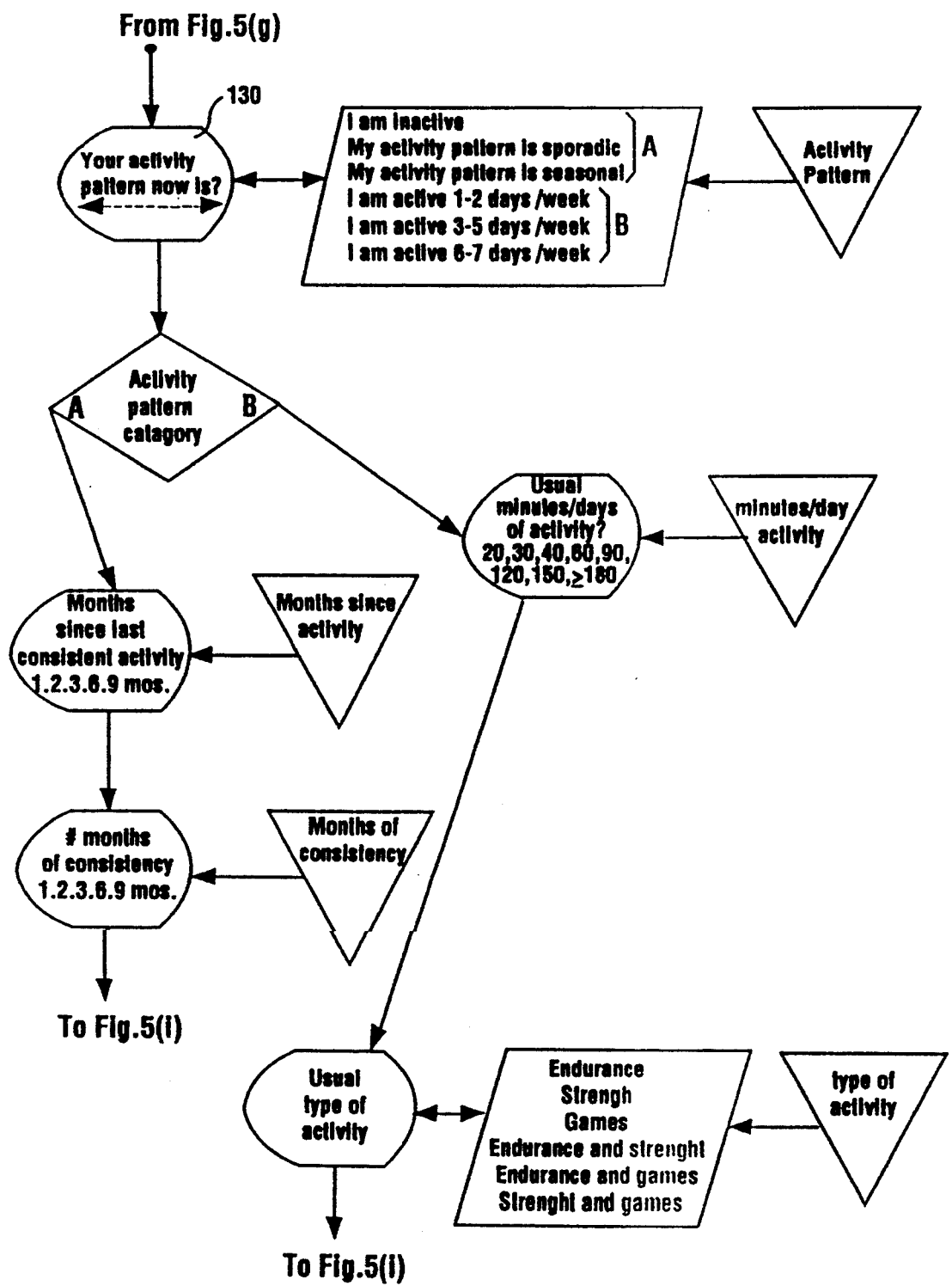

FIG. 5(h) commences with screen 130 seeking to determine what the user's present activity pattern is, whether inactive, sporadic, or seasonal, and under each of these three categories, the extent of each.

Figure 5I:
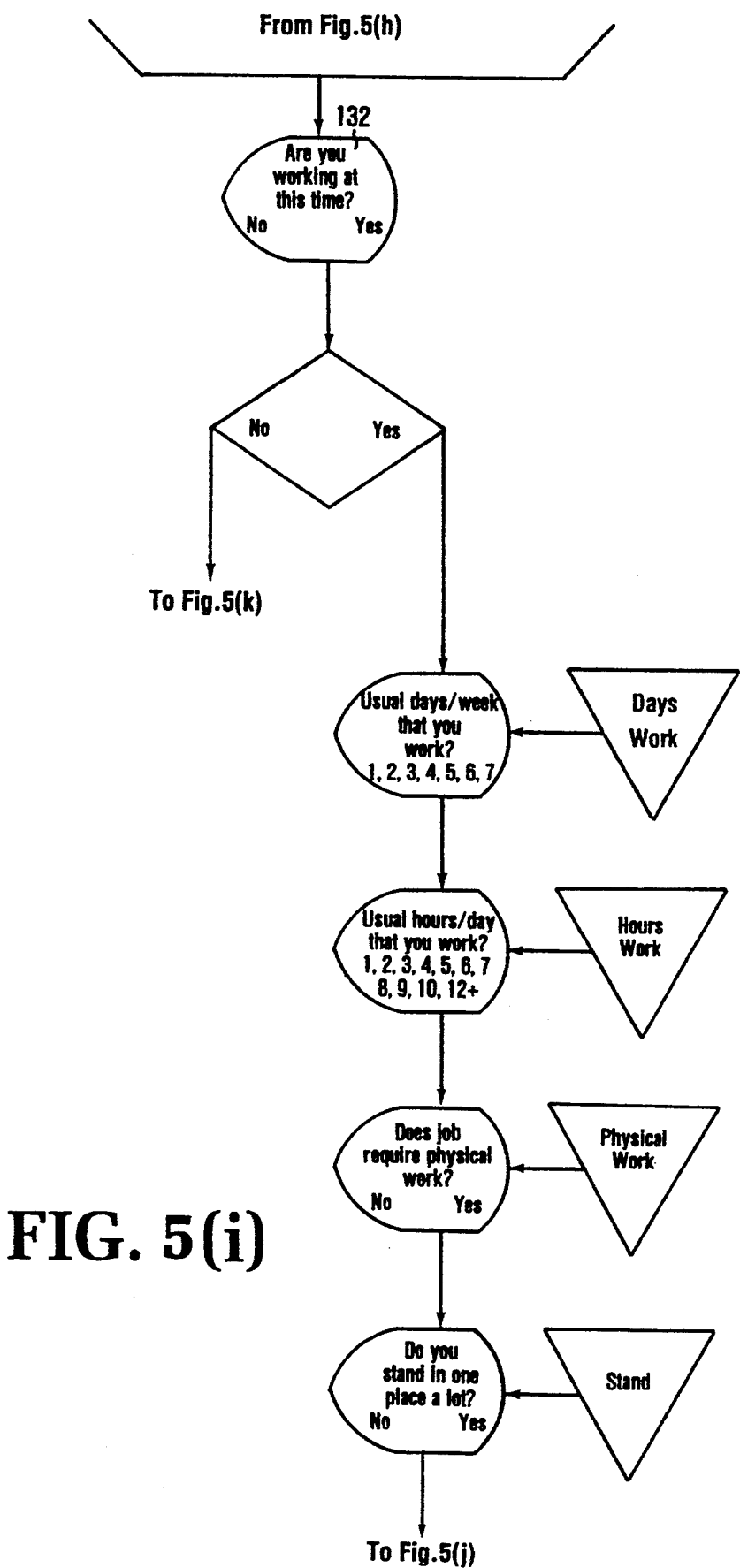
Figure 5J:
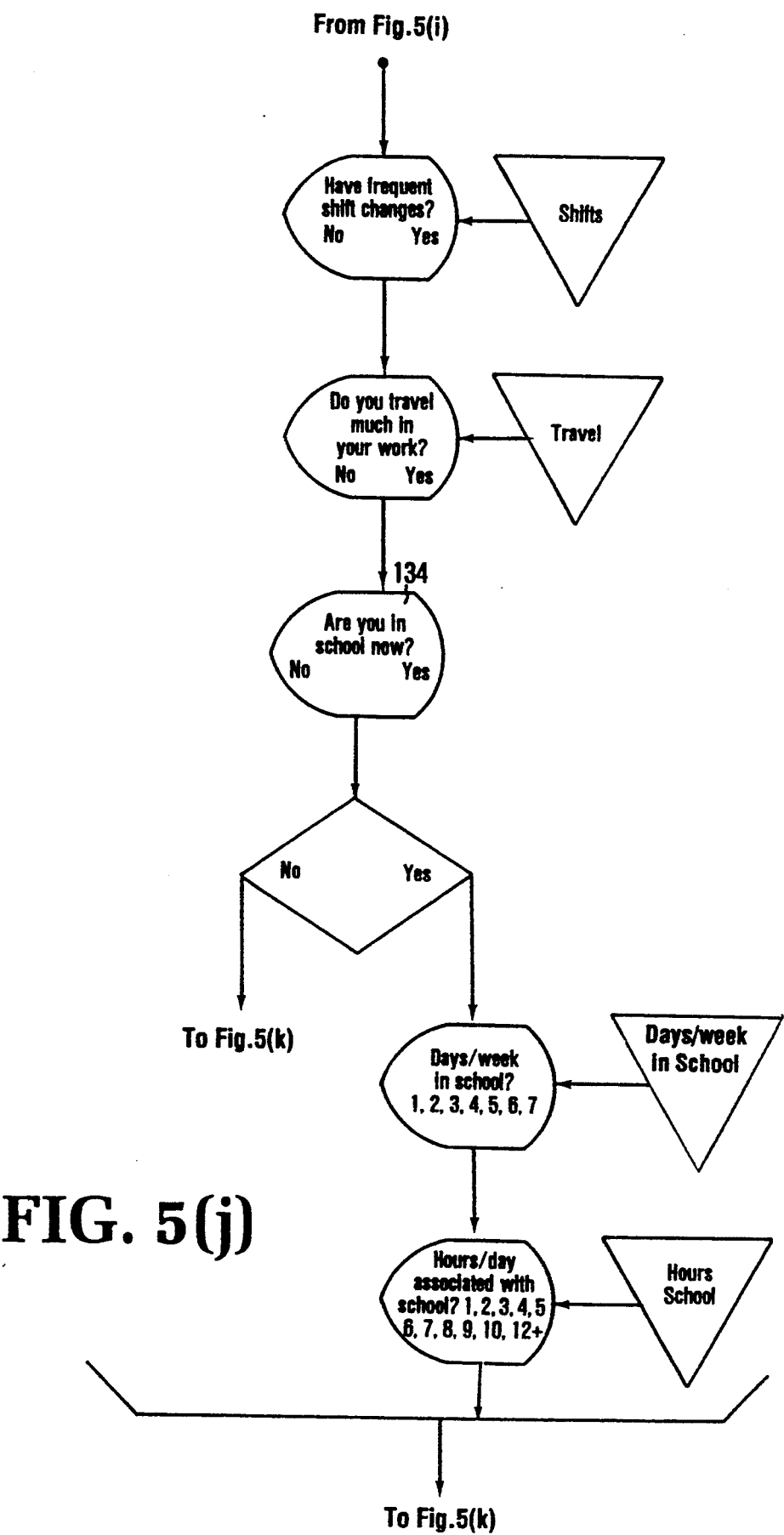

FIG. 5(i) commences with screen 132 to determine whether the user is working at the time. This parameter is critical again to show the extent of the availability of time to devote to activity. Likewise in FIG. 5(j), screen 134 prompts the user to indicate whether he or she is in school at the time. Again this relates to the amount of time available that the user has.

Figure 5K:
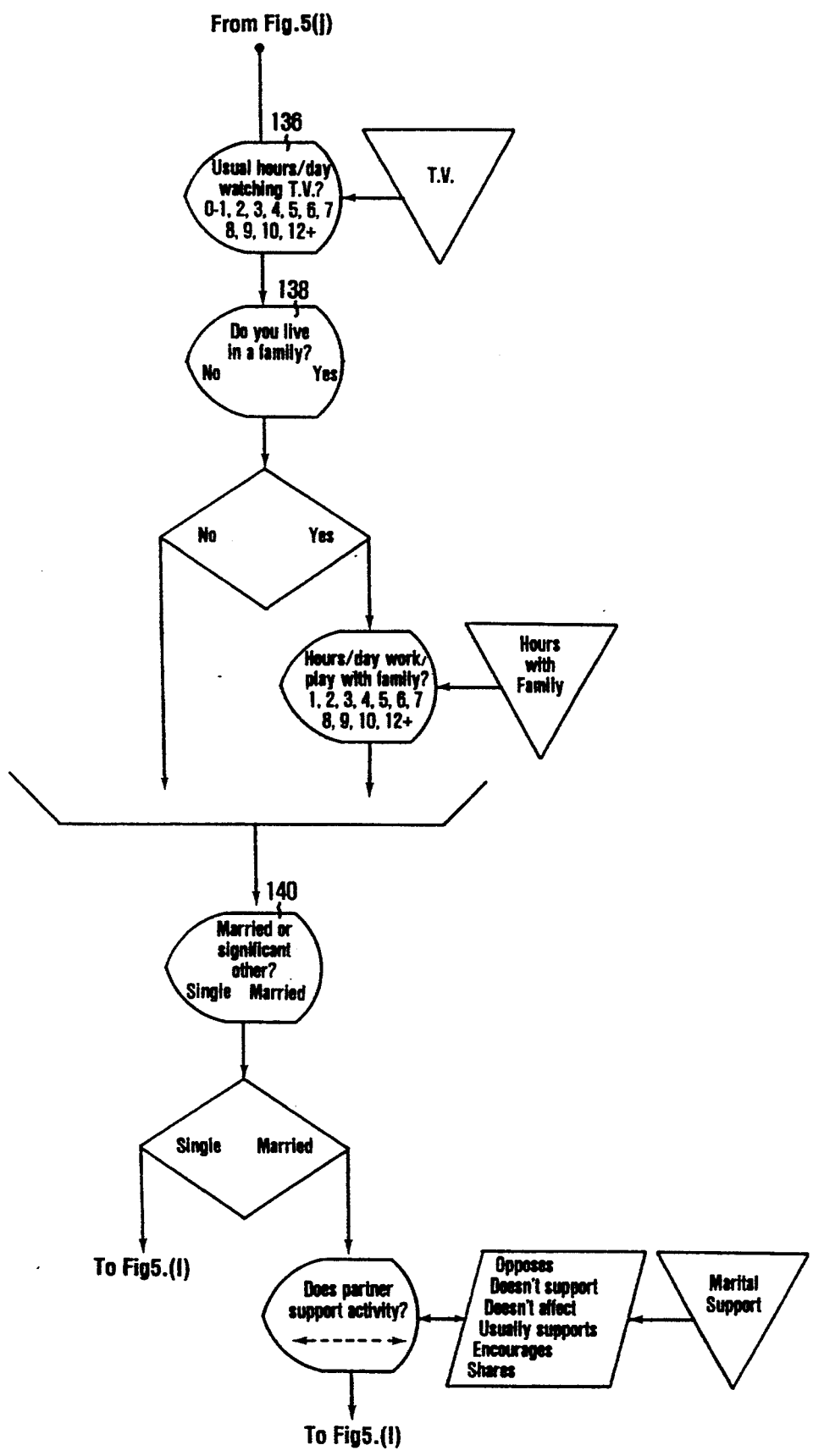
Figure 5L:
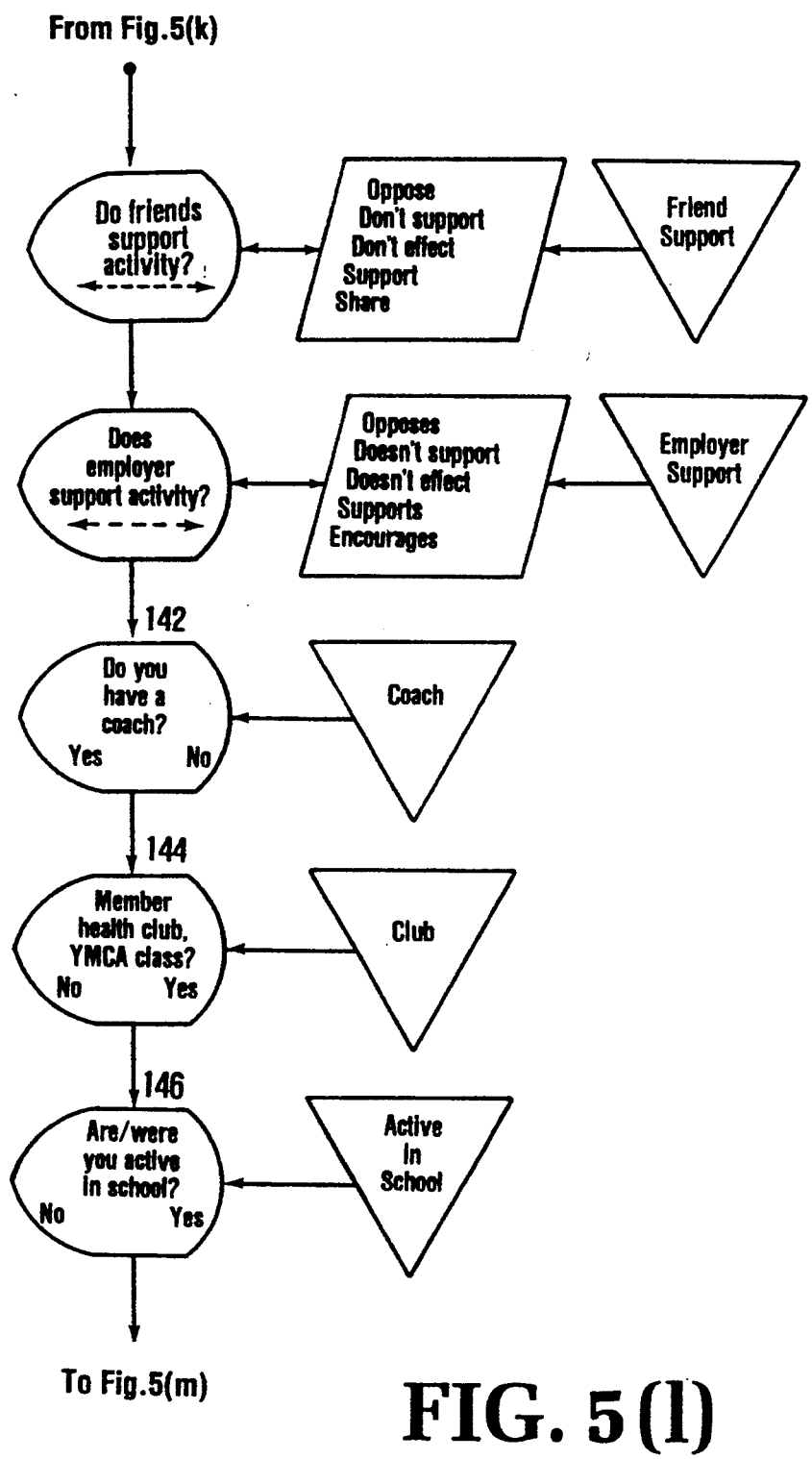
Figure 5M:
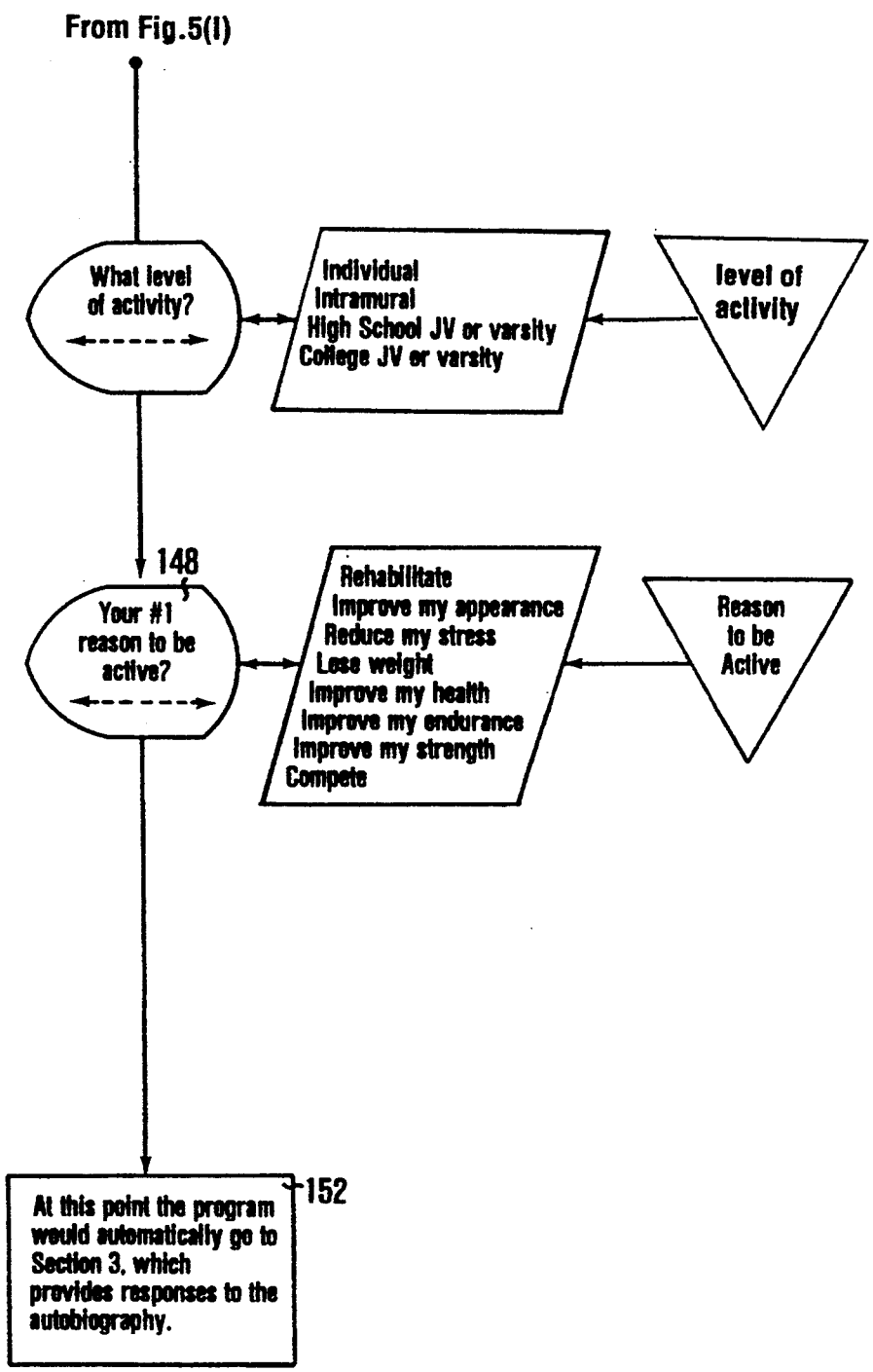

FIG. 5(k) prompts the user to indicate how much time is spent watching TV (screen 136), and whether the user lives in a family or not (screen 138). FIG. 5(k) further prompts the user to indicate whether the user is married (screen 140), an aid in determining the extent of support for activities. As shown in FIGS. 5(k), 5(l) and 5(m), activity support 90 (FIG. 5(a)) is determined. The particular elements important in this determination are the existence of partner, friend, and employer support, the presence or absence of a coach, club, the activity in school, activity reasons (screen 48 in FIG. 5(j)), and activity opinion (screen 150 in FIG. 5(m)).

Figure 6A:
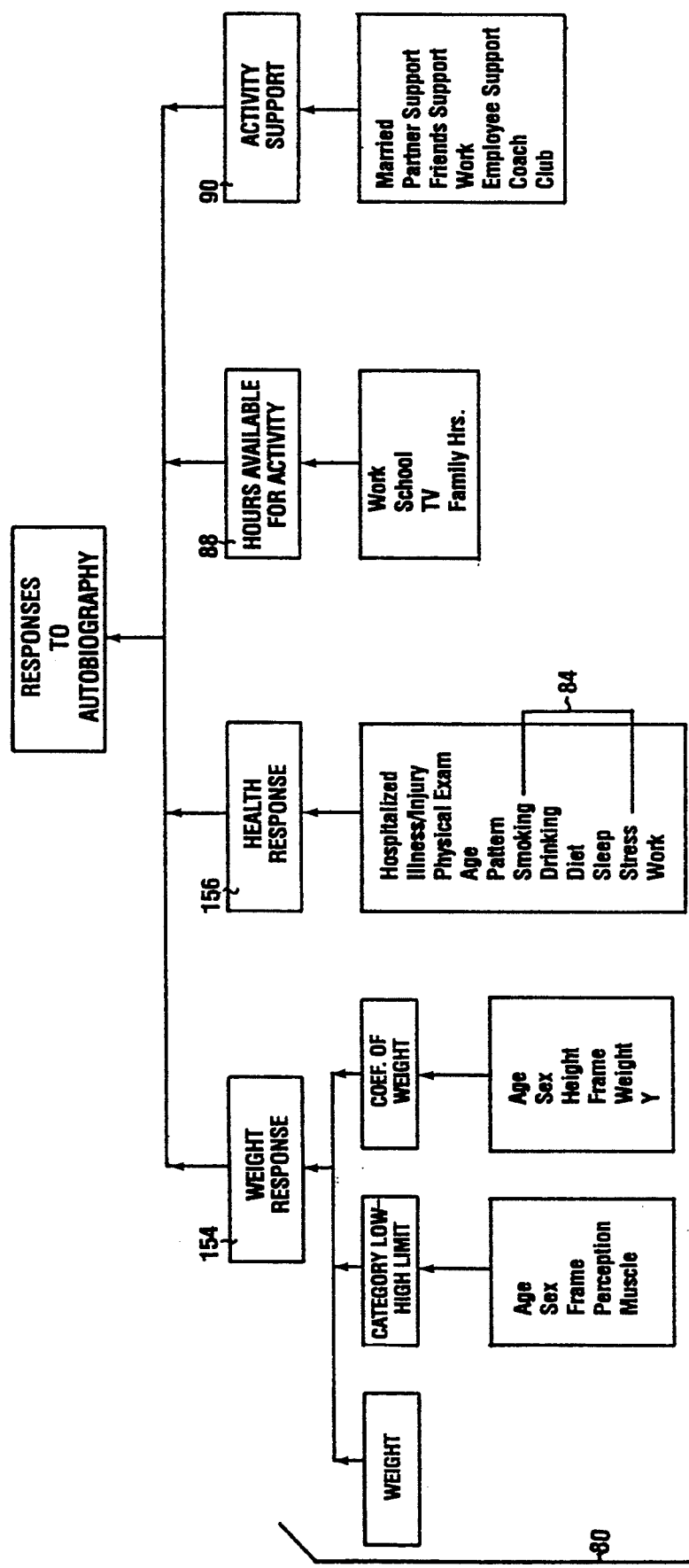
FIG. 6(a) is an overview of the Responses to Autobiography, Section 3.

Upon completion of Section 2, as set forth in box 152 on FIG. 5(m), the user proceeds immediately to responses to autobiography. All FIGS. 6 set forth calculation for the responses to the autobiography, showing how the various aspect of Section 2 are integrated into Section 3, and the mathematical computations involved in determining activity level. As shown in FIG. 6(a) the individual characteristics 80 are entered into weight response (box 154). Health history 82, health habits 84 and activity level 86 are entered into health response (box 156). Likewise hours available for activity 88 and activity support 90, combined with weight response 154 and health response 156 are all brought together into the determination of starting points 44 (FIG. 8).

Figure 6B:
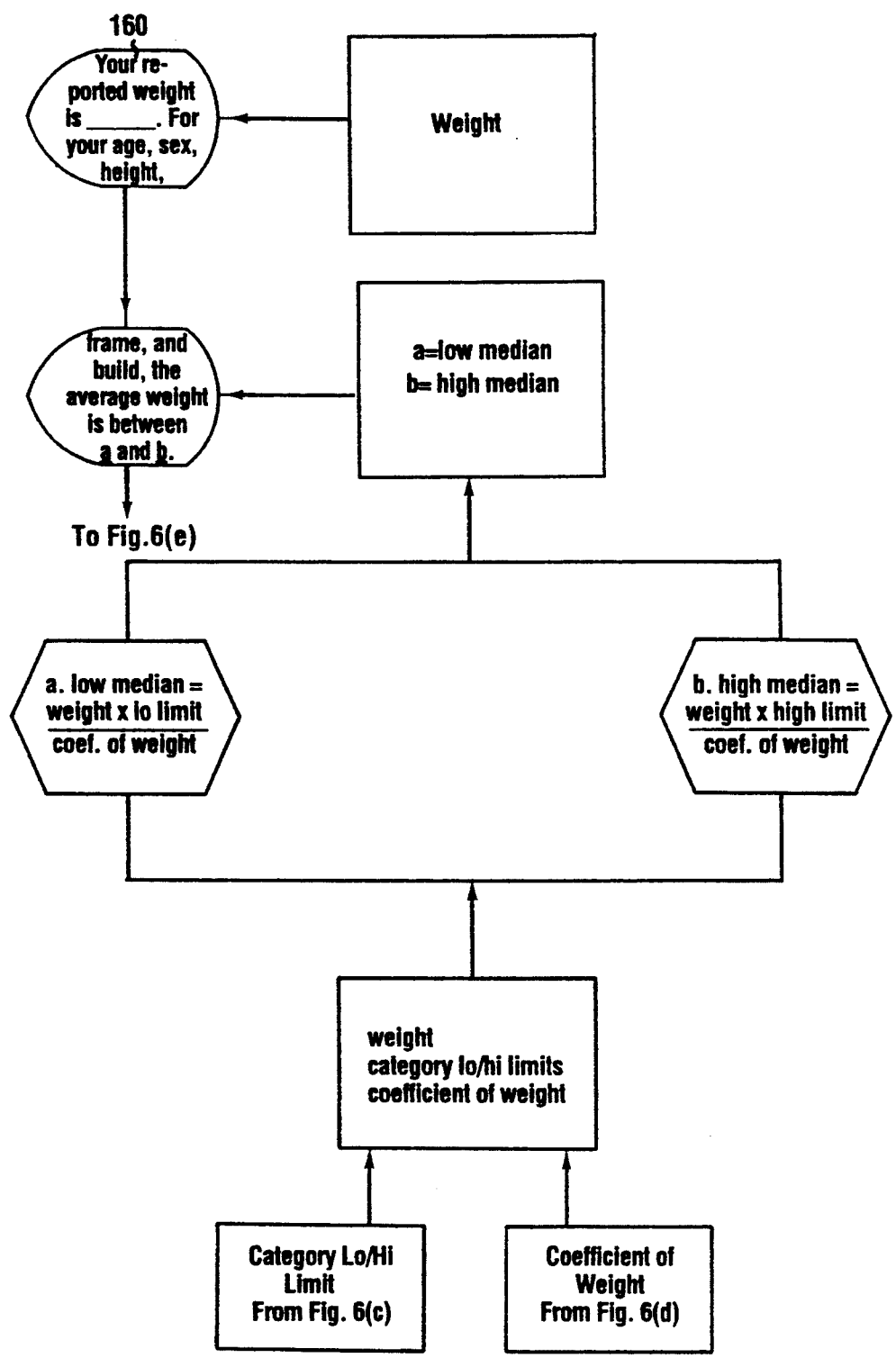
FIGS. 6(b) through 6(i) are flow charts of the Responses to Autobiography, Section 3.
Figure 6C:
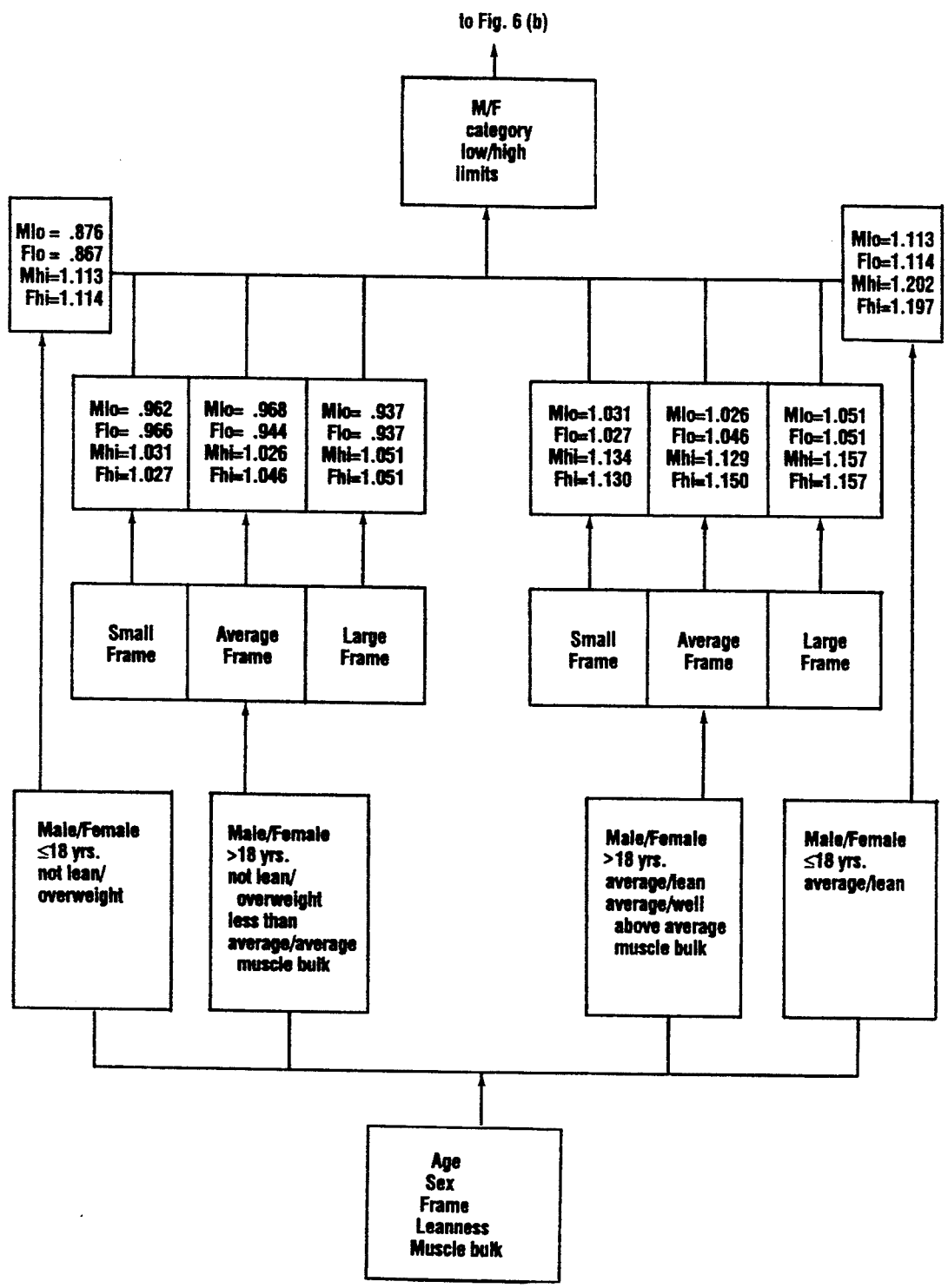
Figure 6D:
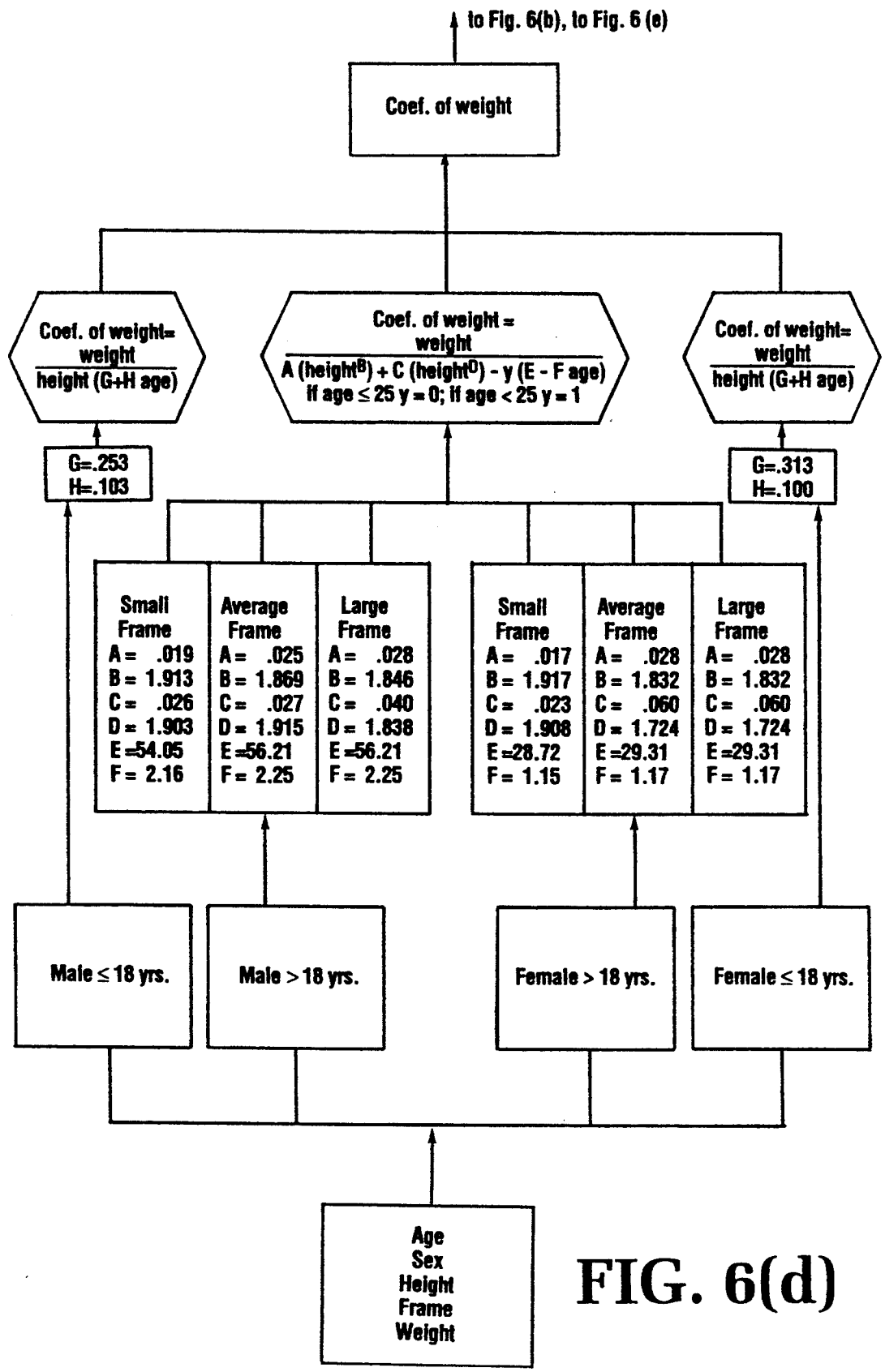
Figure 6E:
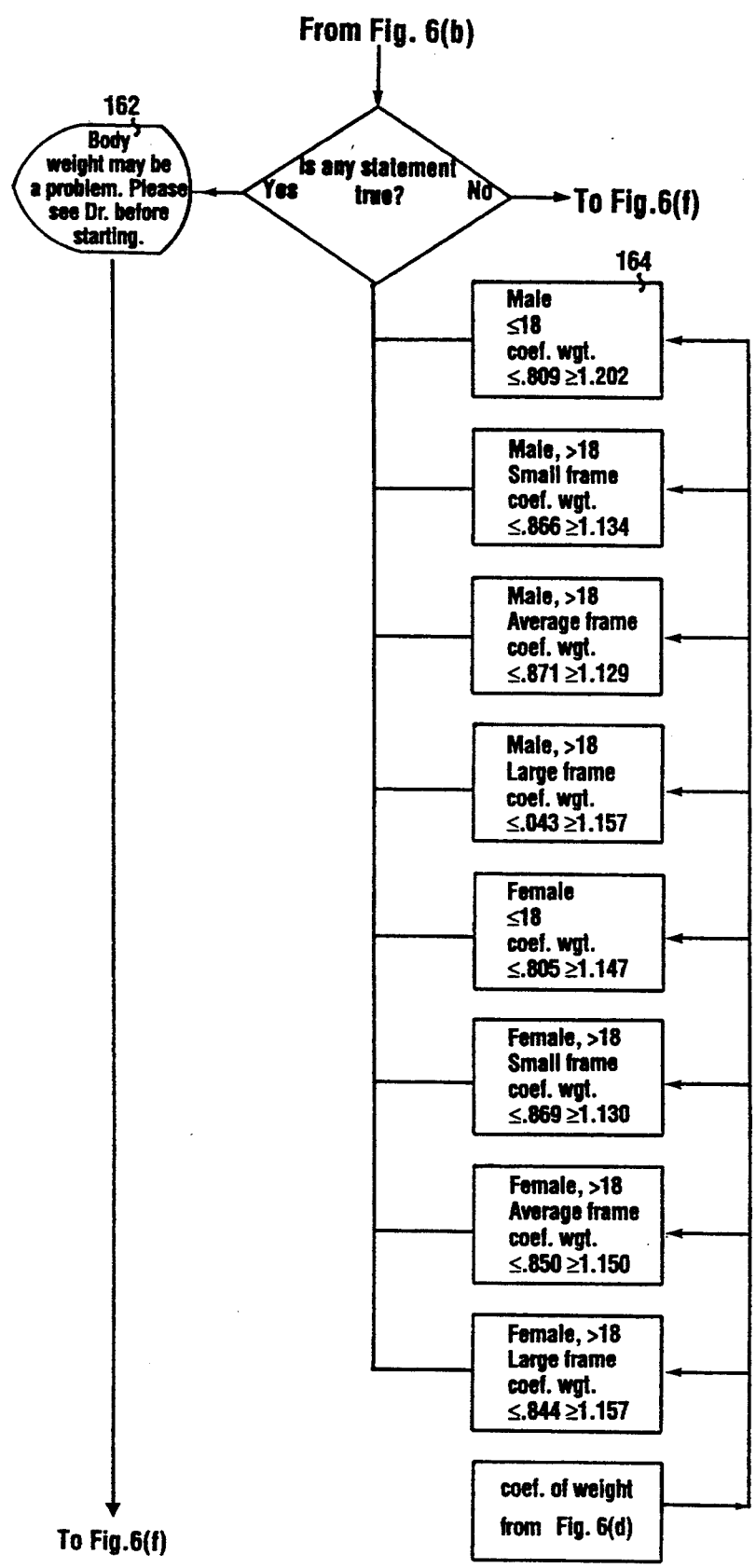

The first screen 160 in FIG. 6(b) sets forth the reported weight from reference 2.5 (screen 100, FIG. 5(c)). From the information provided on age, sex, frame, and build, the program determines an average weight range between A, as a low median weight and B, as a high median weight. Determination is set forth on FIGS. 6(b) through 6(e). The calculation is based upon determining what I have discovered to be "coefficients of weight" and specific "category limits".

Low median weight and high median weight are calculated as follows:

3.2.1 Low Median $= \dfrac{\text{weight} \times \text{category low limit}}{\text{coef. of weight}}$ 3.2.2 High Median $= \dfrac{\text{weight} \times \text{category high limit}}{\text{coef. of weight}}$ 3.3 Category high low limits
   Low limits vary between .865 & 1.114
   High limits vary between 1.026 & 1.205

3.4 Coef. of weight for:
   $Y = 0$ or $1$ older than 18; male; small frame $=$ $$\dfrac{\text{weight}}{.019\,(\text{height}^{1.913}) + .026\,(\text{height}^{1.903}) - Y(54.05 - 2.16\,\text{age})}$$

older than 18; male; average frame $=$ $$\dfrac{\text{weight}}{.025\,(\text{height}^{1.869}) + .027\,(\text{height}^{1.915}) - Y(56.21 - 2.25\,\text{age})}$$

older than 18; male; large frame $=$ $$\dfrac{\text{weight}}{.028\,(\text{height}^{1.846}) + .040\,(\text{height}^{1.838}) - Y(56.21 - 2.25\,\text{age})}$$

18 or less; male $= \dfrac{\text{weight}}{\text{height}\,(.253 + .103\,\text{age})}$ older than 18; female; small frame $=$ $$\dfrac{\text{weight}}{0.17\,(\text{height}^{1.917}) + .023\,(\text{height}^{1.908}) - Y(28.72 - 1.15\,\text{age})}$$

older than 18; female; average frame $=$ $$\dfrac{\text{weight}}{.019\,(\text{height}^{1.912}) + .029\,(\text{height}^{1.875}) - Y(29.31 - 1.17\,\text{age})}$$

older than 18; female; large frame $=$ $$\dfrac{\text{weight}}{.028\,(\text{height}^{1.832}) + .060\,(\text{height}^{1.724}) - Y(29.31 - 1.17\,\text{age})}$$

18 or less; female $= \dfrac{\text{weight}}{\text{height}\,(.313 + .100\,\text{age})}$ After screen 160 sets forth the average weight between A and B low median and high median, the next screen 162 will be displayed only if there is a body weight problem. A body weight problem is determined as set forth in boxes 164, by determining the sex, frame, and coefficients of weight for the individual user. I have found that my specific coefficients of weight are key triggers to an indication of a weight problem, and these ranges are set forth in FIG. 6(e).

Figure 6F:
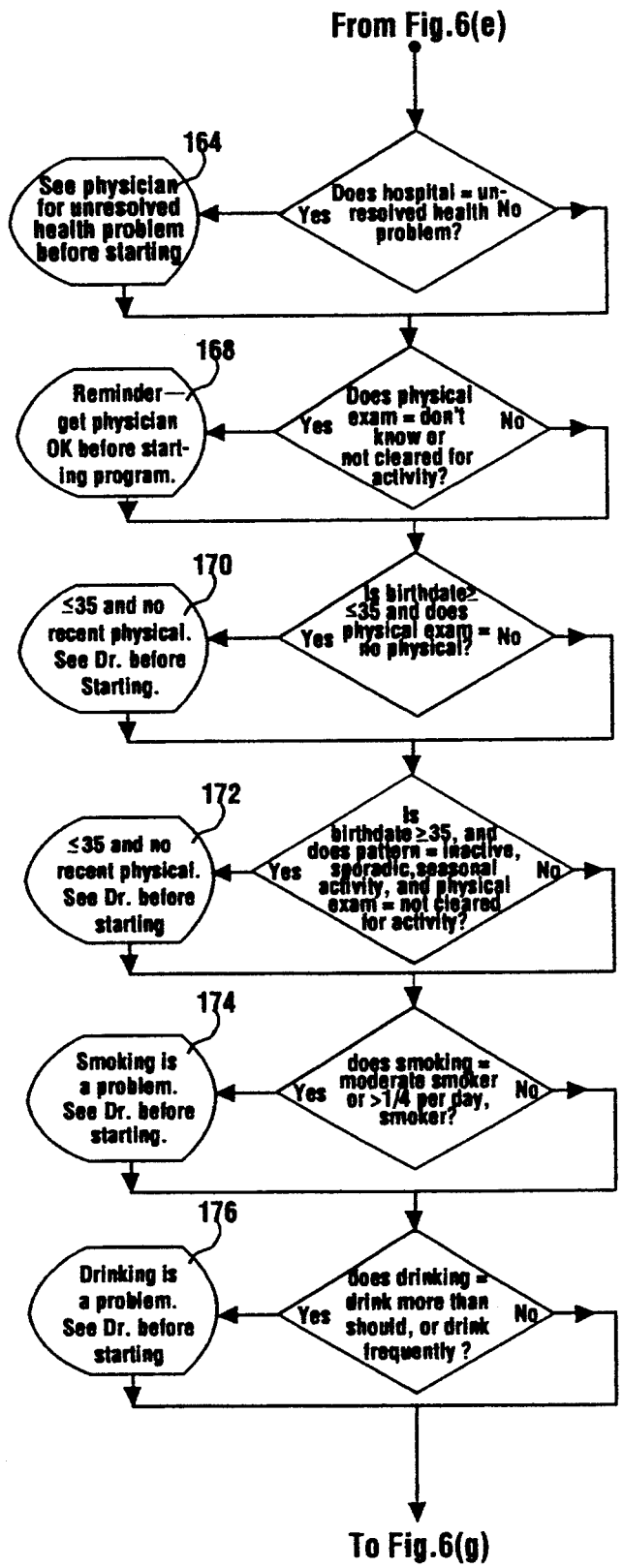

FIG. 6(f) represents a series of other screens 164 through 176 which will be set forth depending upon the answer provided in Section 2 above. Screen 164 indicates that there is a non-resolved health problem, as triggered in response to that given previously. Likewise screen 168 reminds the patient to get a physician's approval before starting the activity, screen 170 indicates that no physical has been had within the prior 12 month period of time, and a physical is recommended. Screen 172, also suggesting that a doctor be seen before starting, arises when the user indicates that he is inactive, sporadic, involved in seasonal activity, or not clear for activity. Screen 174 is triggered if the person is a moderate smoker or greater that ¼ pack per day smoker. If the user drinks frequently, then screen 176 is triggered again suggesting that the patient visit a doctor before commencing the exercise regime.

Figure 6G:
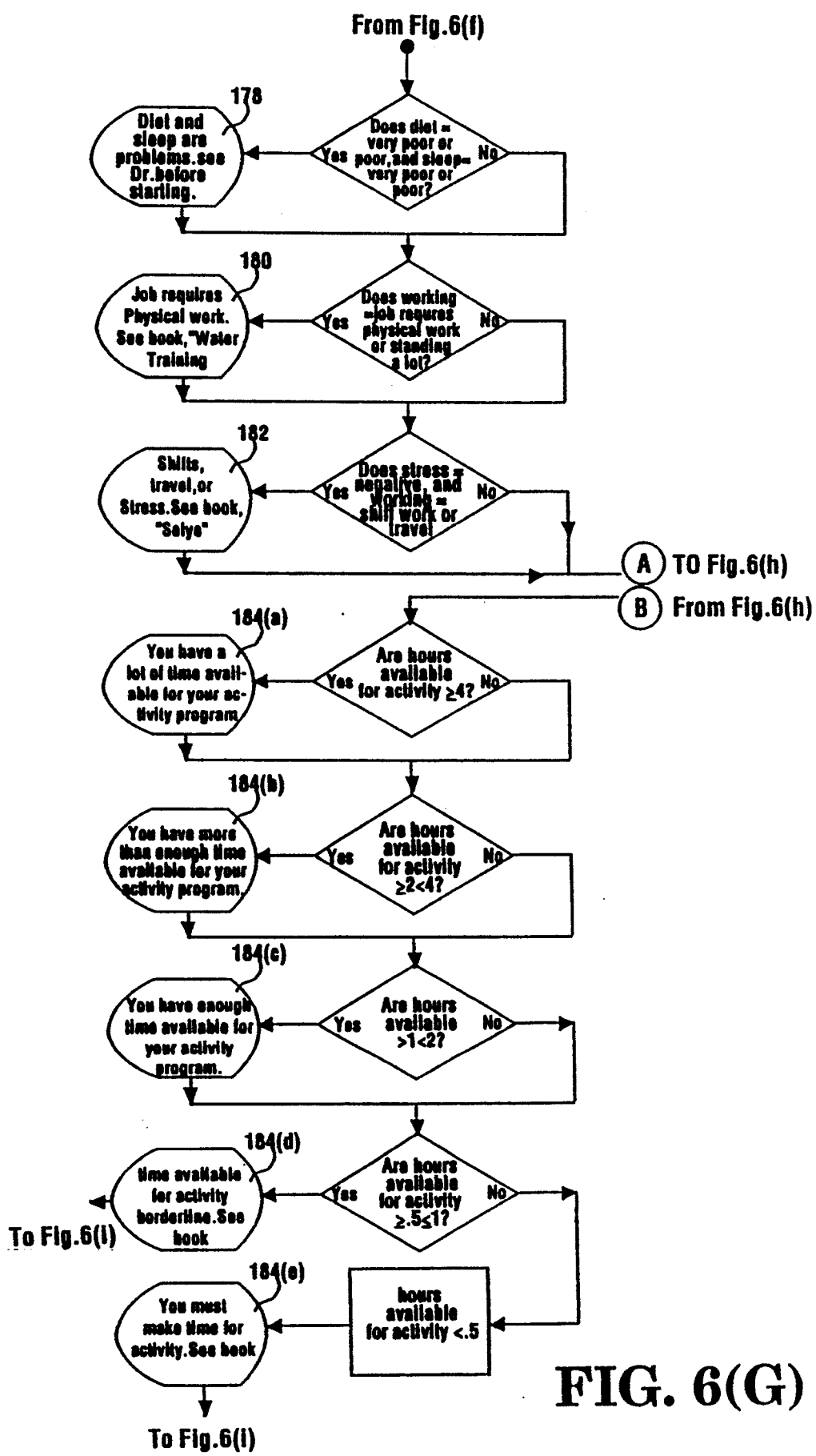
Figure 6H:
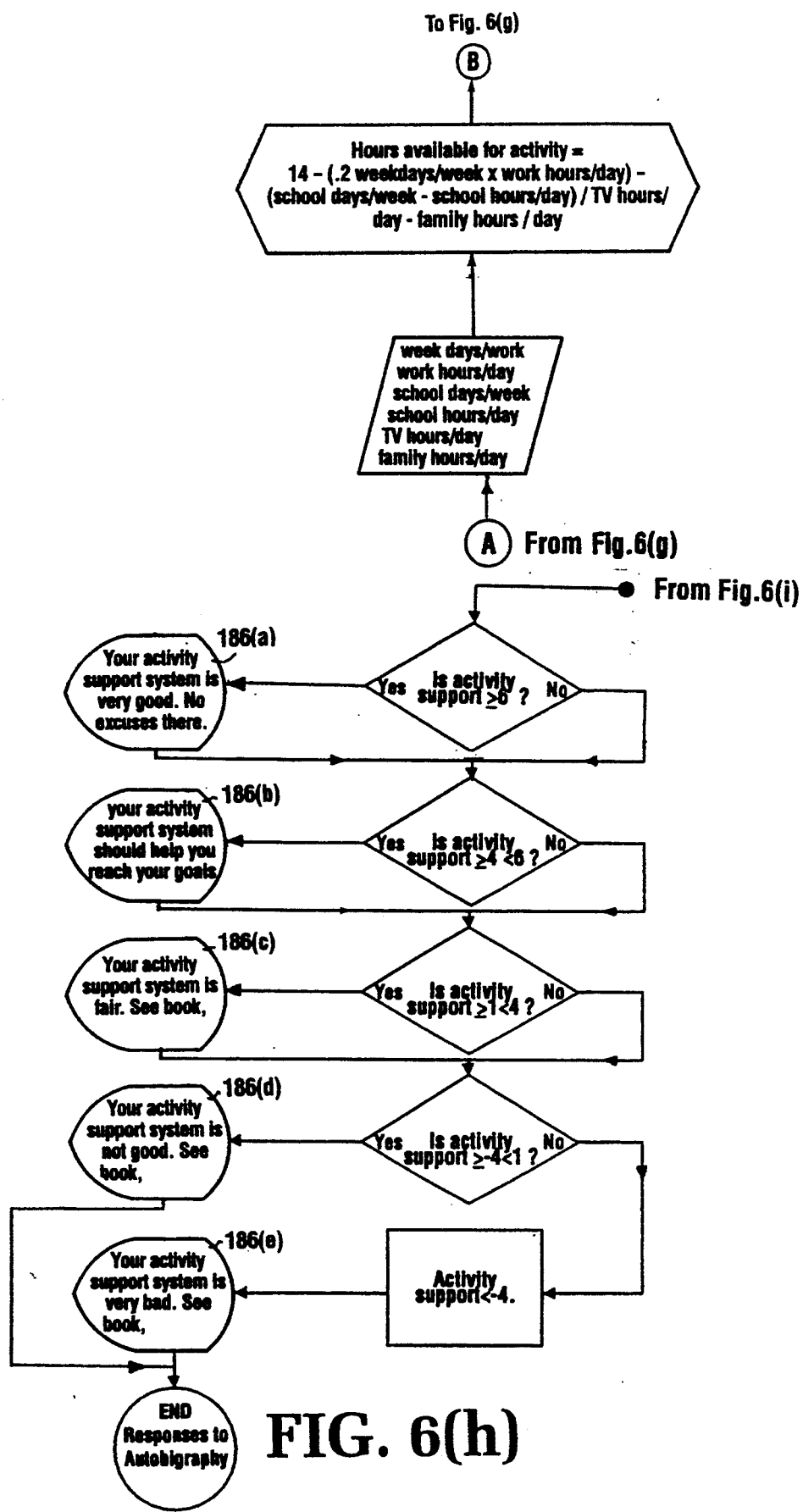

Screens 178 through 182 are shown at the top of FIG. 6(g). Screen 178 further recommends that the user see a doctor as a consequence of diet or sleep problems, predicated upon responses given in Section 2.13 and 2.14 above.

One of screens 184(a) through 184(e) will be triggered depending upon a determination of hours available for activity, Section 3.15. Hours available for activity are determined as follows:

3.15.1 Hours available for activity=14−(0.2 work hours per week)−(0.2 school hours per week)−TV hours per day)−(family hours per day)

Figure 6I:
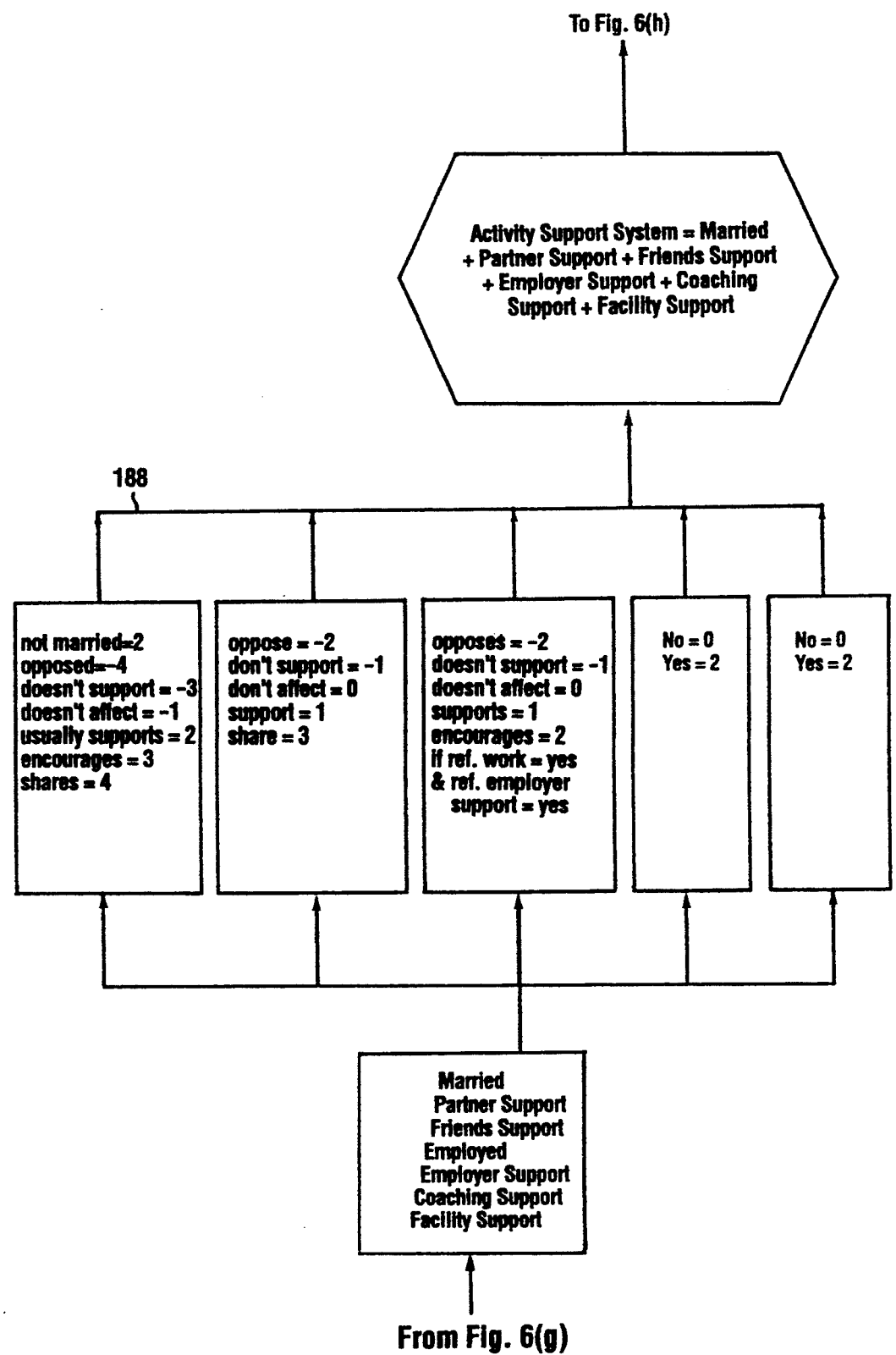

One of screens 186(a) through 186(e) will be triggered as a consequence of the computation indicated in FIG. 6(i), and concerning the activity support system possessed by the user. The activity support system can either help or hurt the user's abilities to reach the user's exercise goals, and consequently are important. As shown in FIGS. 6(i) boxes 188, various numerical quantities have been assigned to the information provided under Sections 2.22 through 2.26 (see FIG. 6(a), and activity support box 90). Based on the information provided above, and the numbers assigned as shown in box 188, FIG. 6(i), the activity support system is gauged on a scale of negative six to positive six (approximately). If greater than six activity, the support system is very good, if less than negative four the activity support system is very bad. Activity support system is calculated by adding up a number assigned for marriage (screen 188(a)), partner support, friend support, employment, employer support, coaching support and faculty support.

A matter of importance in determining proper amount of exercise for the user of the system is also a determination of fitness level, which is indicated as box 42 on FIG. 3, and is broken out in detail in FIGS. 7(a) through 7(m). When the user enters fitness 42, the volume of oxygen consumed ($VO_2$) is determined. Generally cells will only work because they can get oxygen. There is a short period of time when they can exist without oxygen but its not life sustaining. The way oxygen gets to the cells is through the respiratory system and then the circulatory system. The efficiency of those systems determines how much oxygen can get to the cells over any given time. The volume of oxygen ($VO_2$) processed by the cells is determined over a period of time. When people take the $VO_2$ tests the amount of oxygen consumed is measured. The determination is generally done by measuring carbon dioxide and oxygen on its return to the machine. Volumetric result indicates how much oxygen is indeed processed and that automatically measures the efficiency of the respiratory system, and in turn the cardiovascular system. People process oxygen depending upon the various aspects of their training. For example, world class runners can process about 75 to 80 ml of oxygen per kilogram of body weight. Cardiac rehabilitation patients on the other hand can only process 17 ml. The average person is closer to the 17 than to the 80. Consequently, it is important to determine the $VO_2$.

Figure 7A:
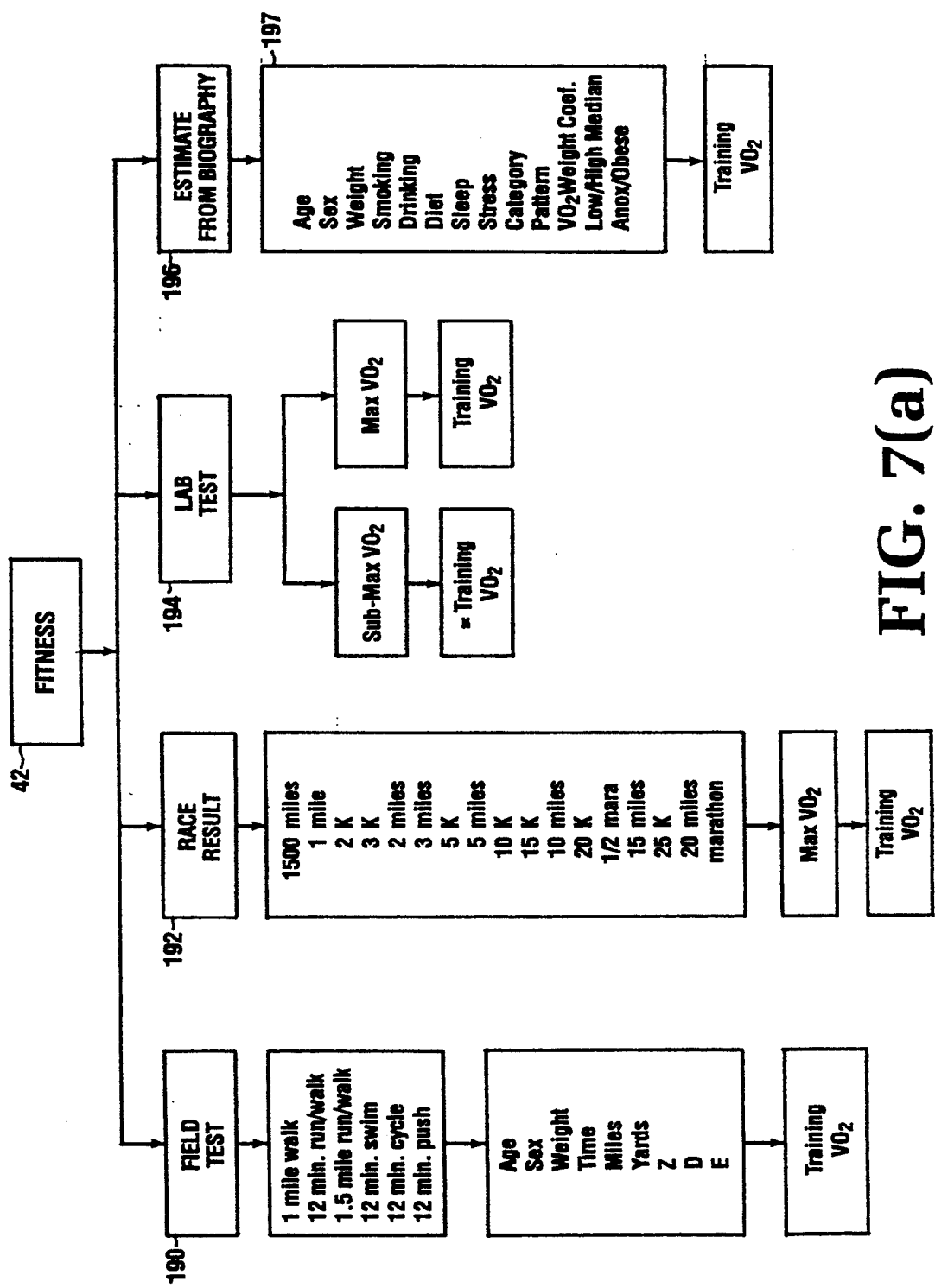
FIGS. 7(a) and 7(b) is an overview of the Fitness, Section of the resident software.
Figure 7B:
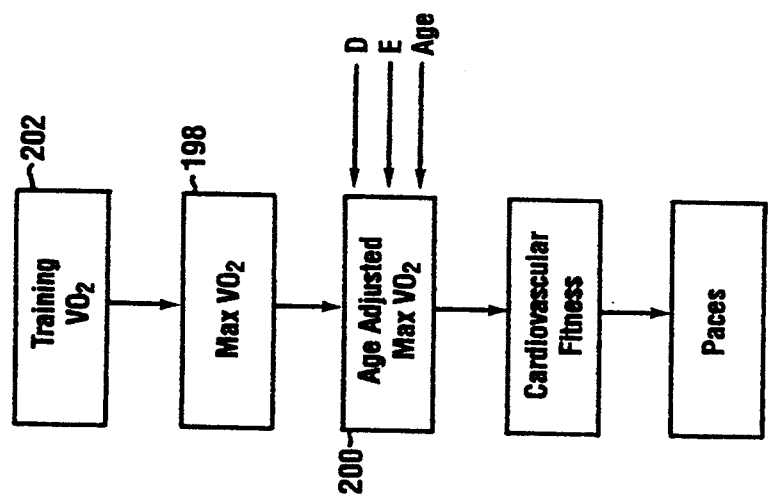

FIG. 7(a) shows four ways in which the invention determines training $VO_2$, including field test 190, test results 192, lab test 194, and estimate from the biography 196. FIG. 7(b) shows a general overview of the calculation of cardiovascular fitness and paces from a determination of training $VO_2$, that is by determining max $VO_2$ 198 and age adjusted max $VO_2$ 200. The specific flow charts setting forth the formulas for determining cardiovascular fitness 42 under Section 4 are set forth in FIGS. 7(c) through 7(m).

Figure 7C:
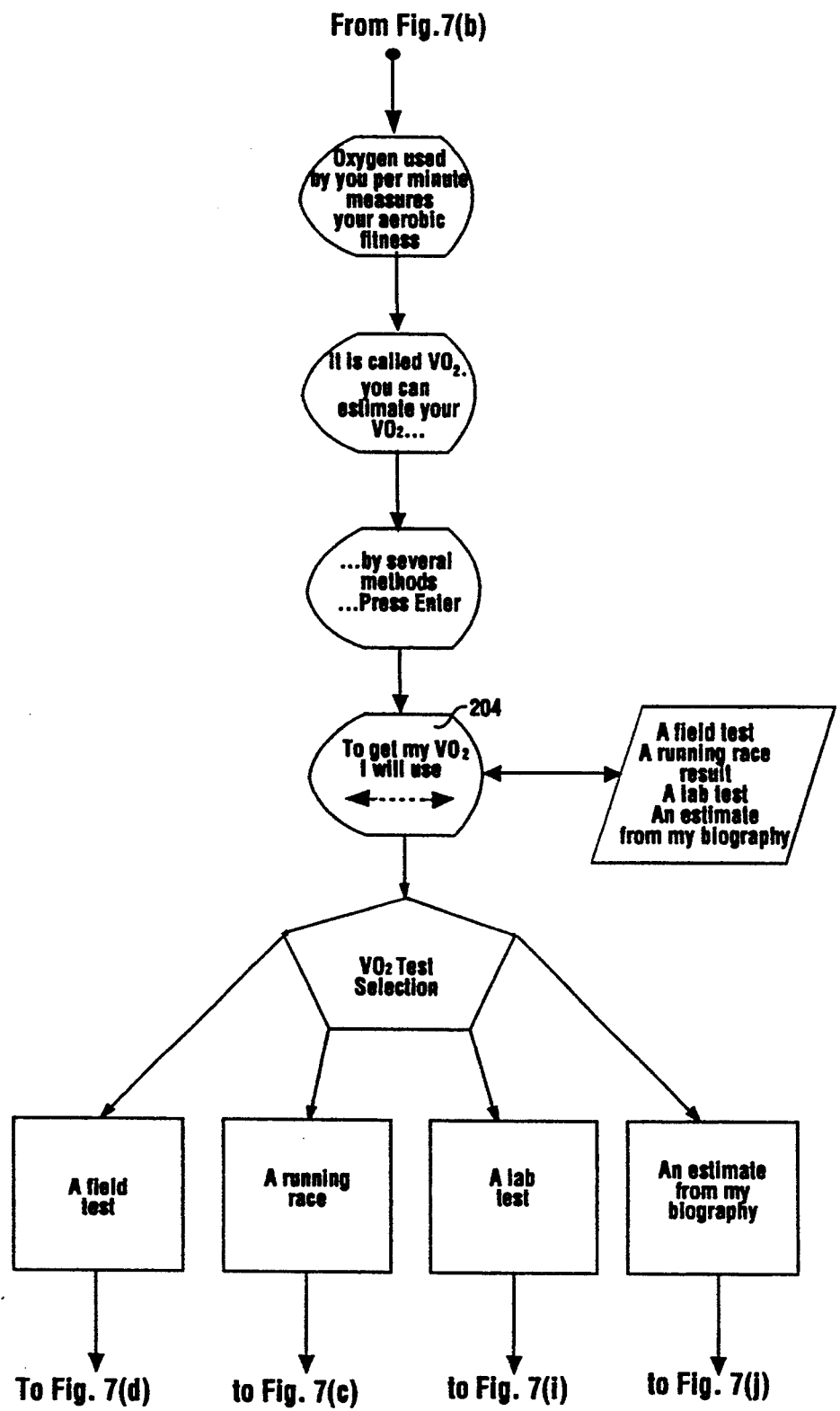
FIGS. 7(c) through 7(m) are flow charts of the Fitness, Section 4.
Figure 7D:
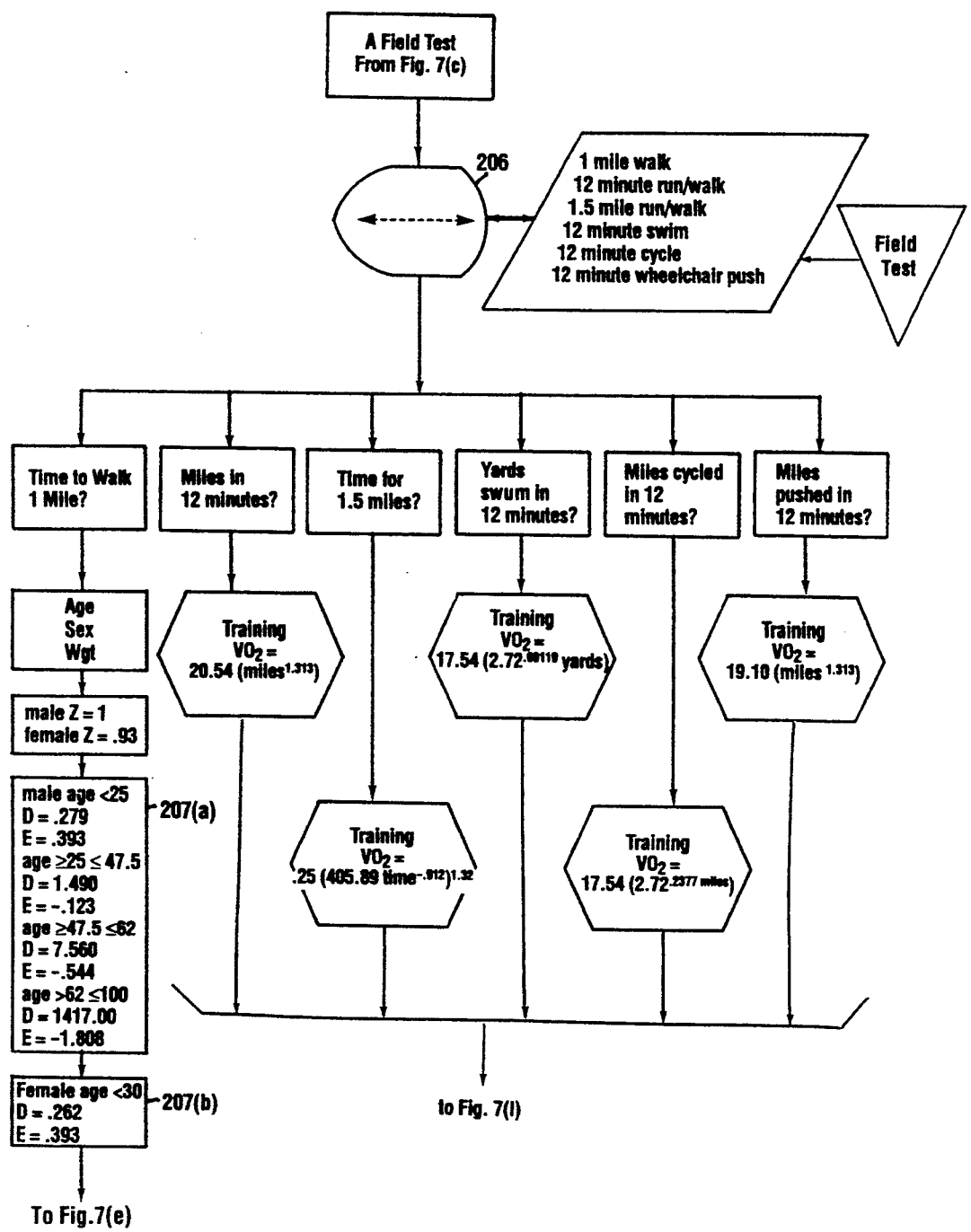
Figure 7E:
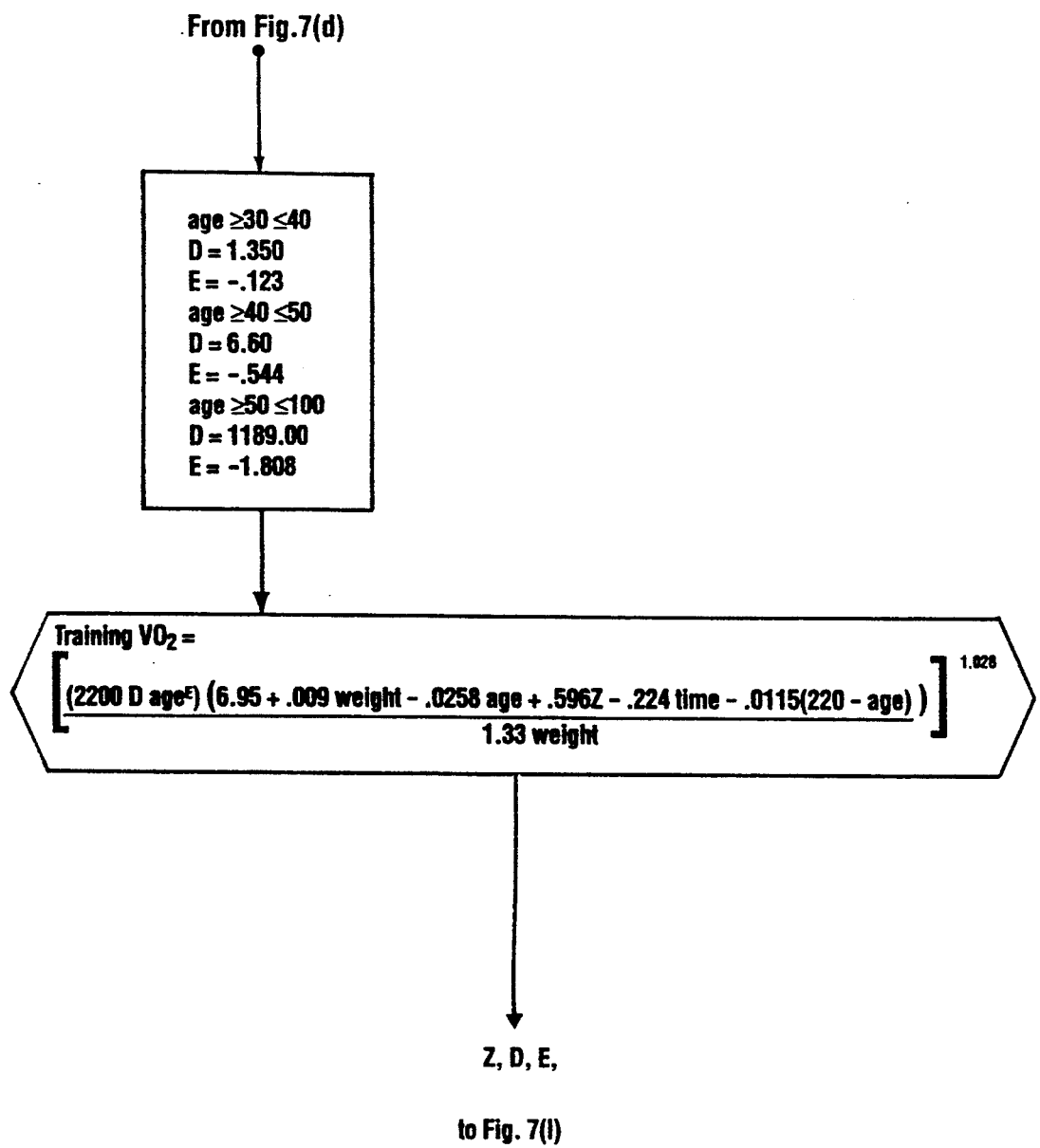

In order to determined training $VO_2$, FIG. 7(c), the user may select on display 204 field test, a running race, a lab test, or an estimate from the bibliography. If field test is selected, FIG. 7(d), display 206 allows the user to select from a one mile walk, a twelve minute run/walk, a 1½ mile run/walk, a twelve minute swim, a twelve minute cycle, or a twelve minute wheel chair push. After the user completes the selected exercise selected under display 206, and enters either the time to walk the mile, the miles in twelve minutes, the time for the 1½ miles, the distance swam in twelve minutes, the miles cycled in twelve minutes, or the miles pushed in the wheel chair in twelve minutes, training $VO_2$ is determined in accordance with the formulas set forth on FIG. 7(d) and FIG. 7(e). The formulas used to determine training $VO_2$ from the walk, run, swim, cycle or push set forth below:

4.2.1 Training $VO_2$ from 1 mile walk =

$$\left[ \frac{(2200\ D(age^E)(6.95 + .009\ \text{weight} - .0258\ \text{age} + .596\ Z - .224\ \text{Time} - .0115\ (\text{age} - 220))}{1.33\ \text{weight}} \right]^{1.023}$$

$Z = 0$ or $1$
$D = .262$ to $1417$
$E = -1.808$ to $.393$ 4.2.2 Training $VO_2$ from 12 minute run/walk = $20.54\ (\text{miles}^{1.313})$ 4.2.3 Training $VO_2$ from 1.5 mile run/walk =

$$.25\ [405.89\ (\text{time}^{-.912})]^{1.32}$$

4.2.4 Training $VO_2$ from 12 minute swim = $17.54\ (2.72^{.00119}\ \text{yards})$ 4.2.5 Training $VO_2$ from 12 minute cycle = $17.54\ (2.72^{.2377}\ \text{miles})$ 4.2.6 Training $VO_2$ from 12 minute wheelchair push =

$$19.10\ (\text{miles}^{1.313})$$

Figure 7F:
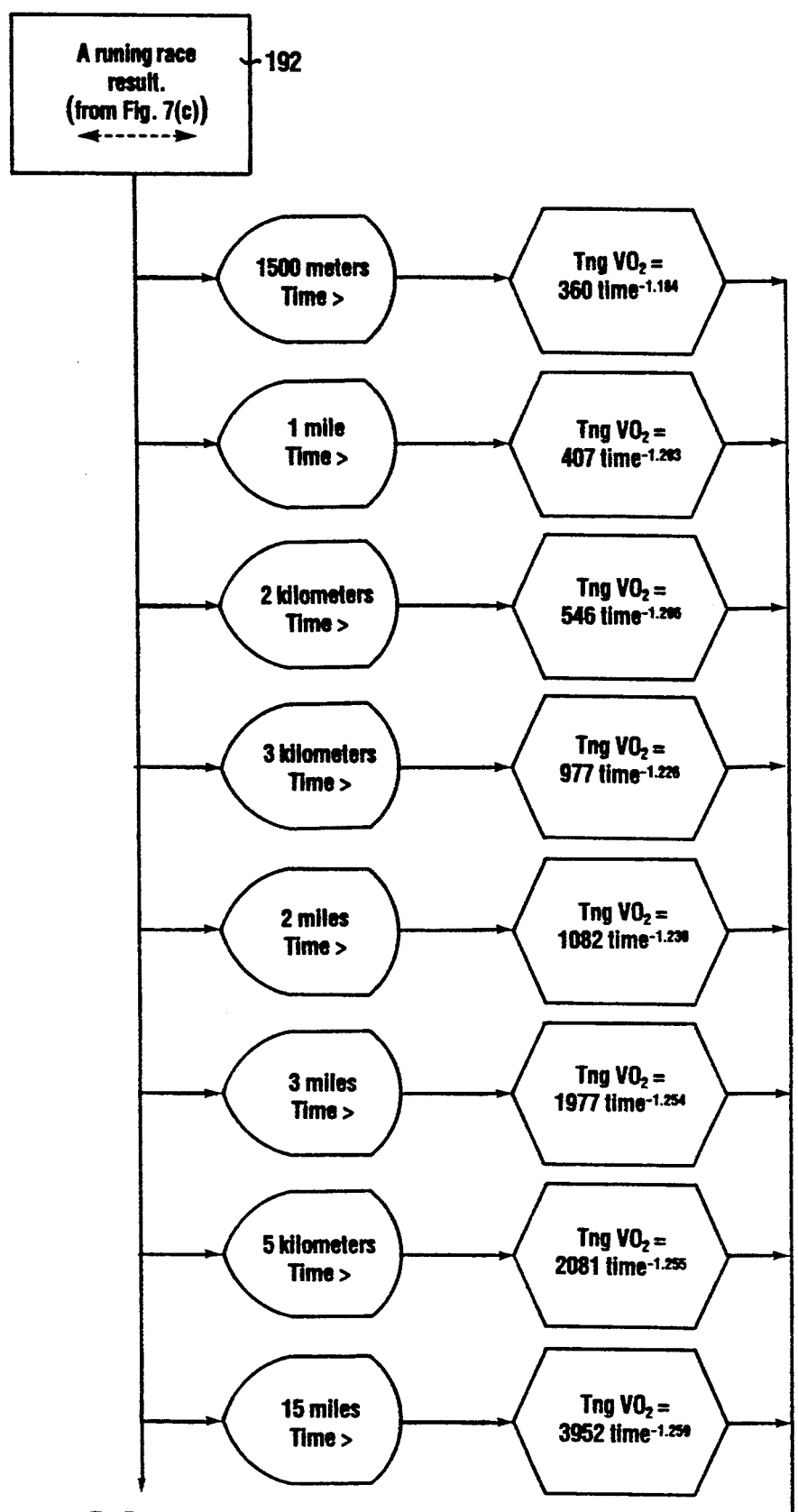
Figure 7G:
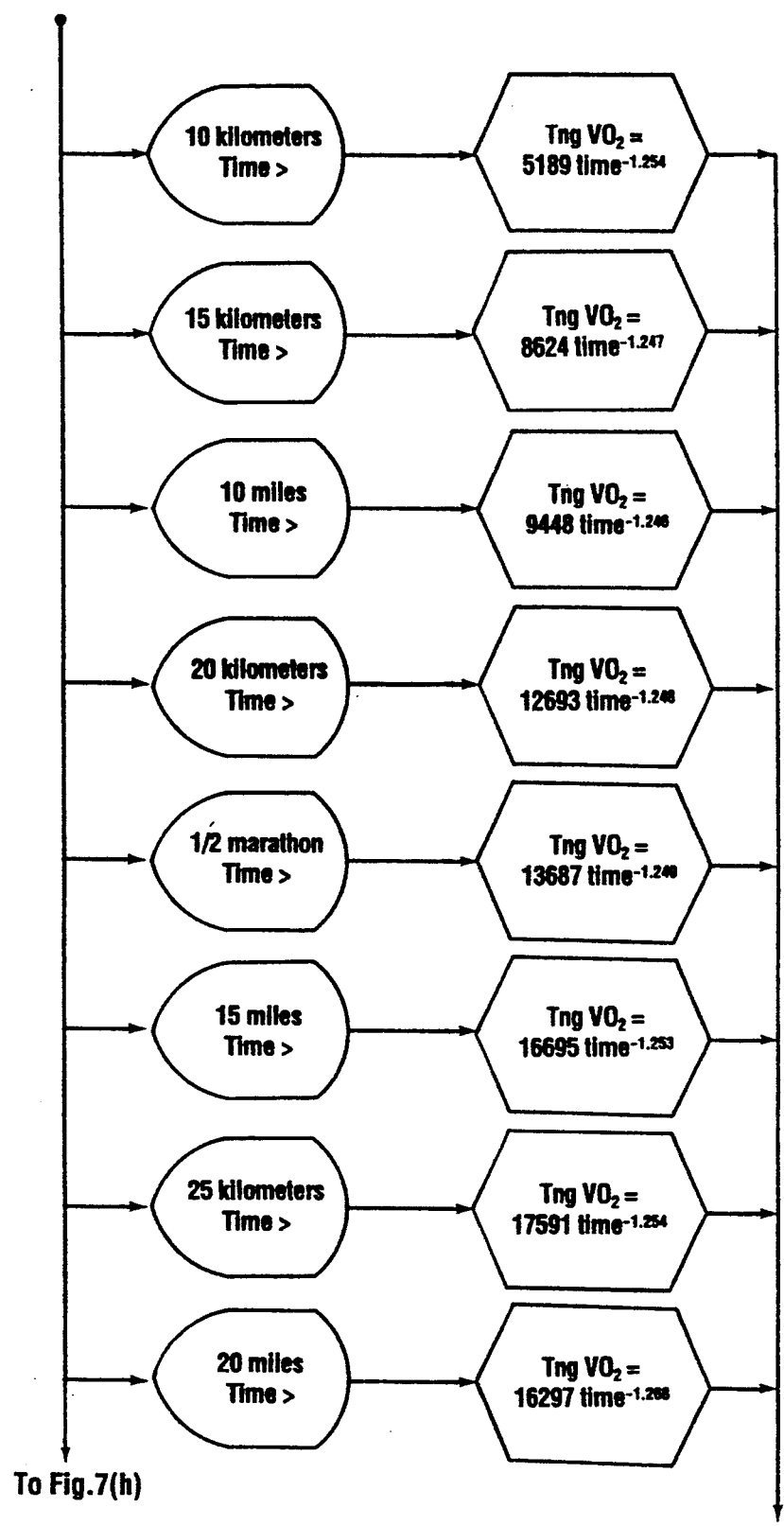
Figure 7H:
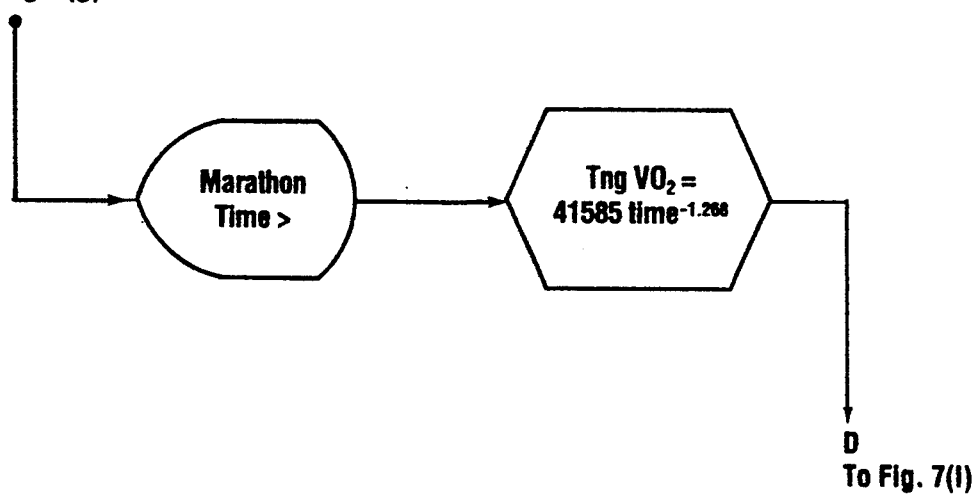

FIG. 7(f) shows the computation if a running race is selected as shown in box 92 in FIG. 7(a). Training $VO_2$ from the running race are determined in accordance with the formulas set forth in FIGS. 7(f), 7(g) and 7(h), and are set forth as follows:

4.3 Training VO₂ from a running race result=
4.3.1 = 360 (time$^{1.184}$)
4.3.2 = 407 (time$^{-1.203}$)
4.3.3 = 546 (time$^{-1.206}$)
4.3.4 = 997 (time$^{-1.226}$)
4.3.5 = 1082 (time$^{-1.230}$)
4.3.6 = 1977 (time$^{-1.254}$)
4.3.7 = 2081 (time$^{-1.255}$)
4.3.8 = 3952 (time$^{-1.259}$)
4.3.9 = 5189 (time$^{-1.254}$)
4.3.10 = 8624 (time$^{-1.247}$)
4.3.11 = 9448 (time$^{-1.246}$)
4.3.12 = 12693 (time$^{-1.248}$)
4.3.13 = 13687 (time$^{-1.249}$)
4.3.14 = 16695 (time$^{-1.253}$)
4.3.15 = 17591 (time$^{-1.254}$)
4.3.16 = 26297 (time$^{-1.268}$)
4.3.17 = 41585 (time$^{-1.268}$)

Figure 7I:
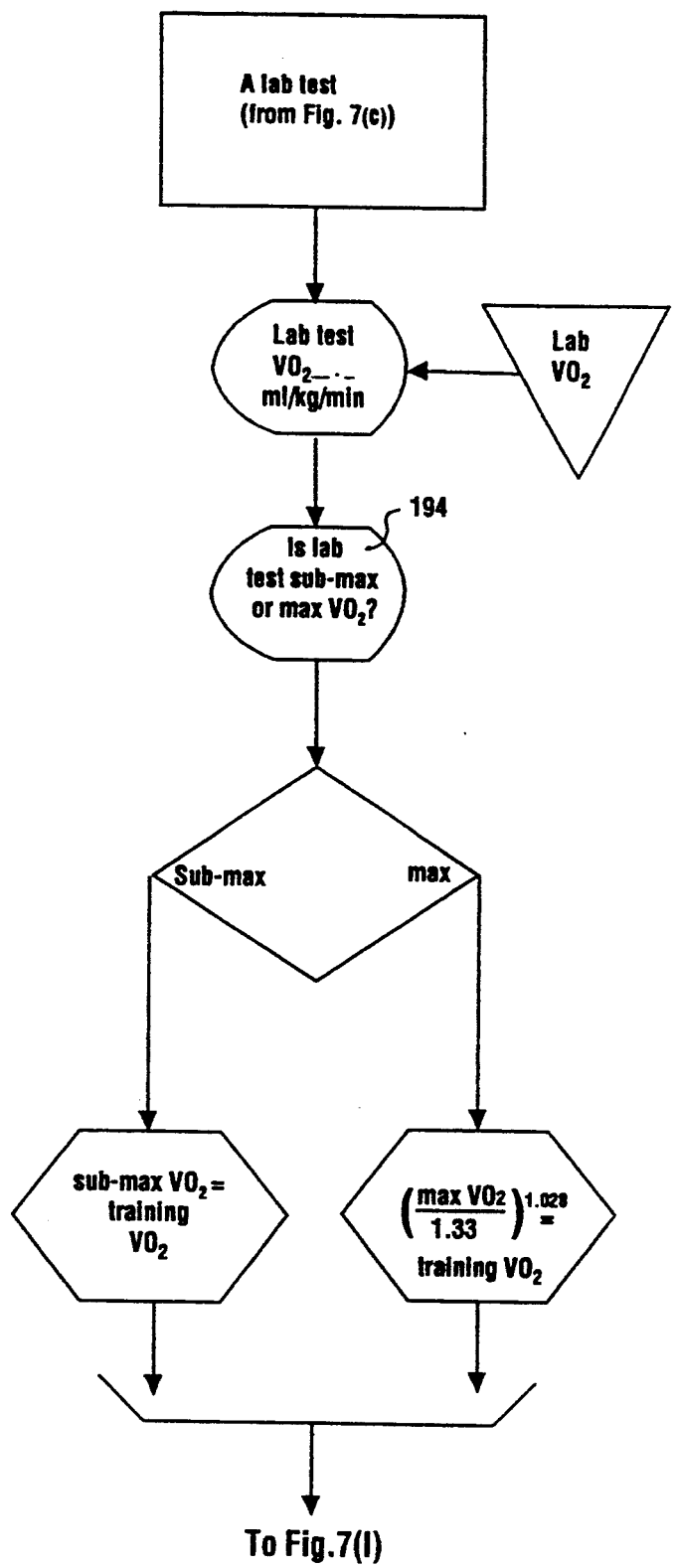

If lab test 194 is selected under fitness 42 (FIG. 7(a)), then, as shown in FIG. 7(i), the user is requested to enter whether the lab test is sub-max or max VO₂ 194 in order to determine whether the lab test results must be modified. If sub-max, then the number entered equals the training VO₂, if max, then the following formula applies:

$$4.4.2 \text{ Training VO}_2 \text{ from Max VO}_2 \text{ lab test} = \frac{(\text{Max VO}_2)^{1.028}}{(1.33)}$$

Figure 7J:
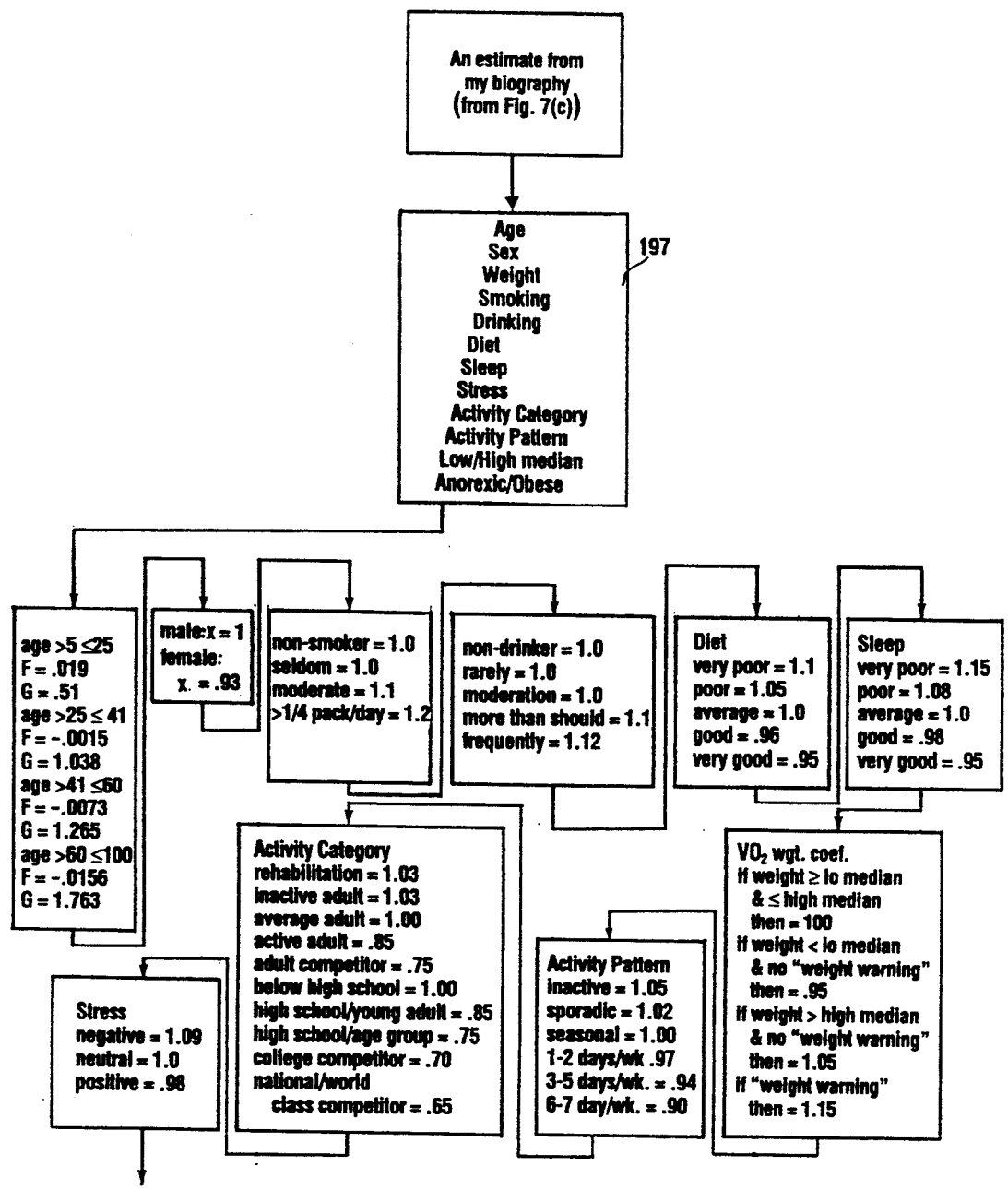
Figure 7K:
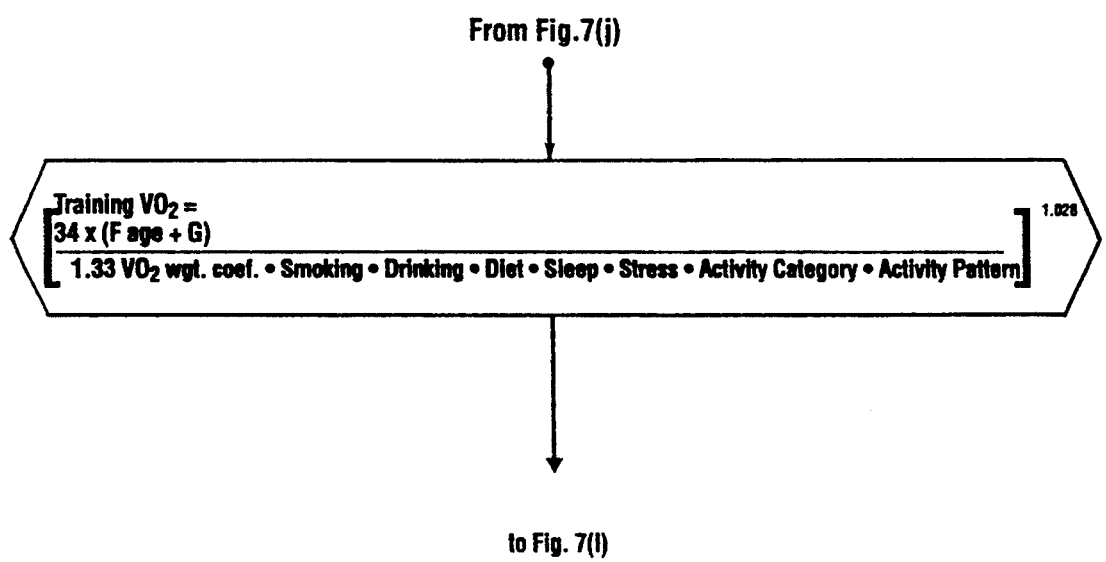

If the user chooses to estimate from the autobiography 196 the training VO₂ (see FIG. 7(a)), this calculation is set forth in FIG. 7(j) and 7(k). The estimate from the autobiography 196 accounts for the various parameters set forth in box 197 on FIG. 7(a), namely the user's age, sex, weight, smoking, drinking, diet, sleep, stress, category, pattern, VO₂ weight coefficient, low/high median weight, whether the user is anorexic/obese. This information was inserted by the user in response to the autobiography Section 2, under start 32 (see FIG. 3). This information is used to determined VO₂ coefficient (f) and (g), as set forth in FIG. 7(j), and then entered into the formula for determining training VO₂ as set forth in FIG. 7 (k) as follows:

4.5.1 Training VO₂ from biography estimate =

$$\left[ \frac{34X(F \text{ age} + G)}{1.33 \text{ VO}_2 \text{ wt coef} \times \text{smk} \times \text{drink} \times \text{diet} \times \text{sleep} \times \text{stress} \times \text{act wt} \times \text{act pat}} \right]^{1.028}$$

The formula was determined by mathematical analysis, and utilizes the variables 197 in order to calculate training VO₂.

Figure 7:
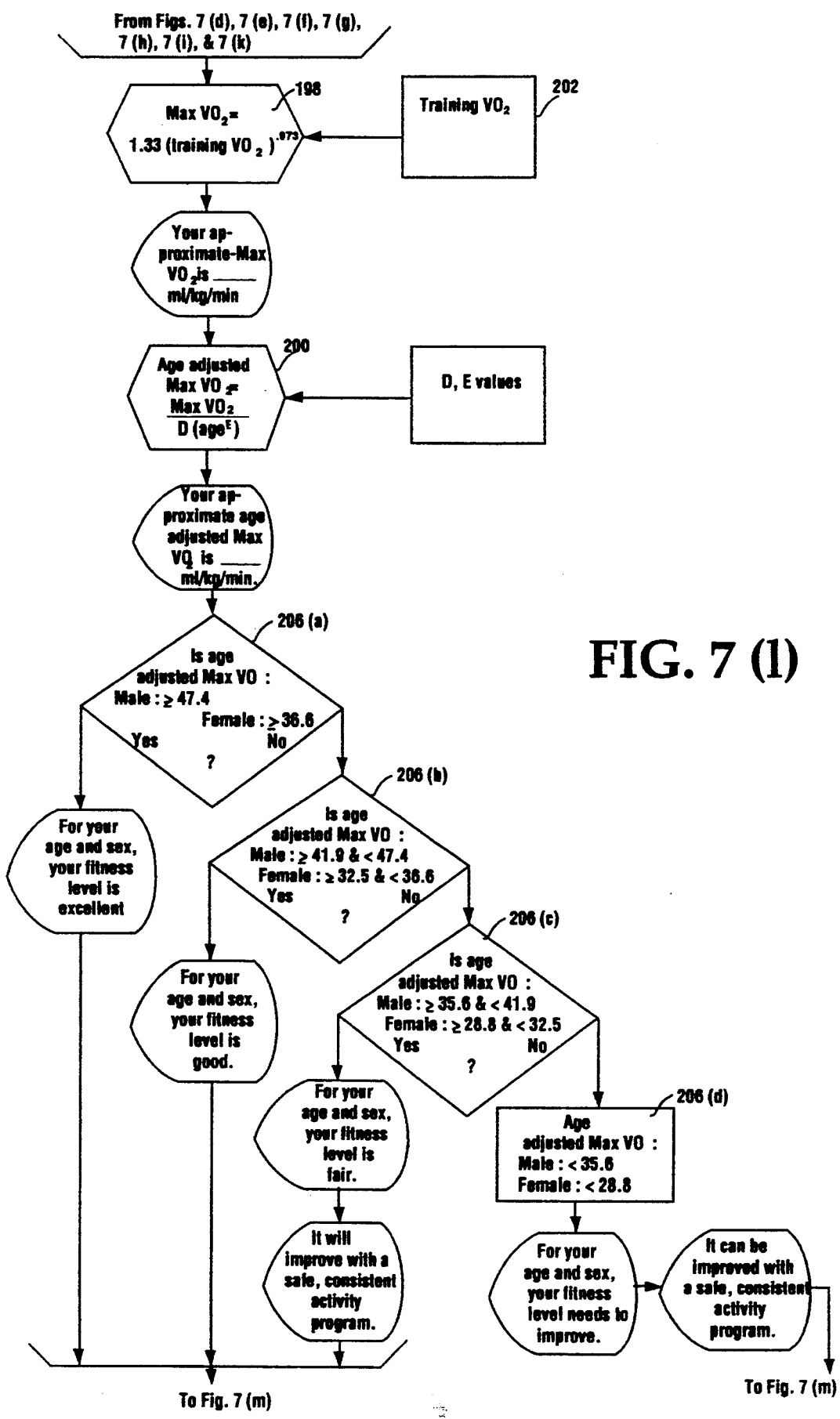
Figure 7M:
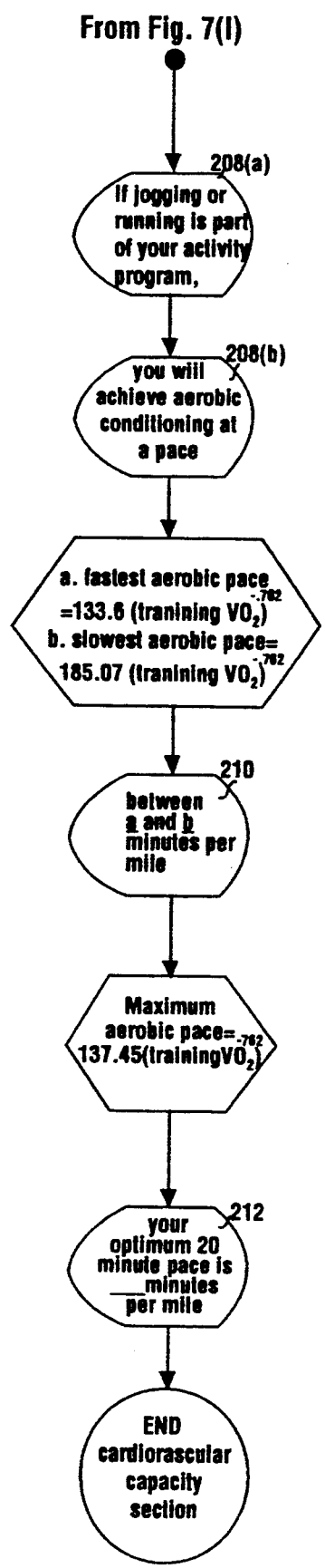

Cardiovascular capacity is not identical to training VO₂, but rather depends upon max VO₂, together with an age adjustment, as set forth in FIGS. 7(l) and 7(m). Clearly, regardless of exercise, as a person ages, is VO₂ consumption is reduced, and thus an age factor must be entered into any proper and comparative exercise regime. The max VO₂ is determined from the training VO₂ in accordance with the following formula:

4.6.1 Max VO₂ = 1.33 (training VO₂$^{0.973}$)

Max VO₂ 198 is then converted to age adjusted max VO₂ 200 utilizing the (d) and (e) values which depend from age, sex and weight, as set forth in boxes 207(a) (male) and 207(b) (female), determined in accordance with the formulas set forth in the formulas 7 (d) and 7 (e) above. Aged adjusted max VO₂, depending from variables (d) and (e) is determined in accordance with the following formula.

$$4.7.1 \text{ Age Adjusted Max VO}_2 = \frac{\text{Max VO}_2}{D(\text{age}^E)}$$

As set forth in FIGS. 7(1), boxes 206(a) through 206(d), if age adjusted max VO₂ is greater than or equal to 47.4 and the user is male, or greater than or equal to 36.6 and the user is female, then the display indicates that the user's fitness level is excellent. From "good" to "needs to be improved" levels are set forth in boxes 206(b) through 206(d) of FIG. 7(l).

As set forth in FIG. 7(m), screen 208(a) and 208(b) state various information concerning paces for jogging, if jogging is part of the exercise program for the user. It must be understood that this system in distinct from those of the prior art which are generally solely for Jogging or running, since some 90 activities are involved, as further defined in greater detail below. However, since jogging is a usual and typical part of most activities, information is provided for the user, predicated upon certain formulas set forth in FIGS. 7(m) and below, to indicate to the user what the optimum aerobic pace, fastest aerobic pace, and slowest aerobic pace should be. This information is calculated and displayed on screens 210 and 212 respectively. The formulas are as follows:

4.11.1 Slowest aerobic pace = 135.07 (training VO₂$^{-0.762}$)
4.11.2 Fastest aerobic pace = 133.60 (training VO₂$^{-0.762}$)
4.11.3 Optimum aerobic pace = 137.45 (training VO₂$^{-0.762}$)

Now that this information has been inputted, and in order to complete the user profile, the user must enter and determine starting points 44 (FIG. 3). The starting points function 44 takes the level of effort that the user is currently expending—or feels he/she can safely expend—on a weekly basis and combines it with the fitness level 42 to determine "goal points" for the first, and subsequent weeks of activity. The program establishes a safe progression of effort that will assist the user in becoming consistent with the activity program.

Figure 8A:
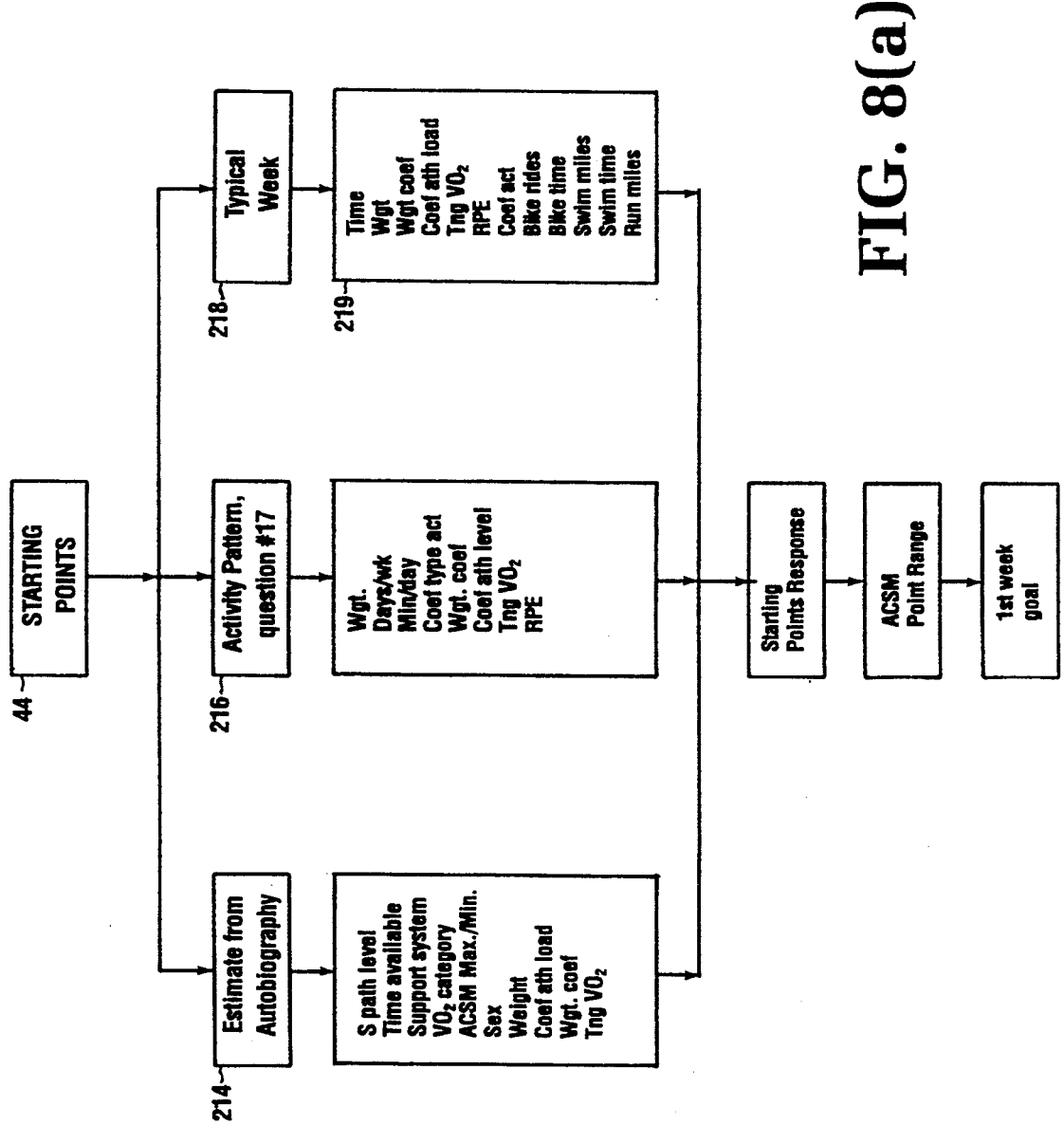
FIG. 8(a) is an overview of the Starting Points, Section 5 of the resident software.
Figure 8B:
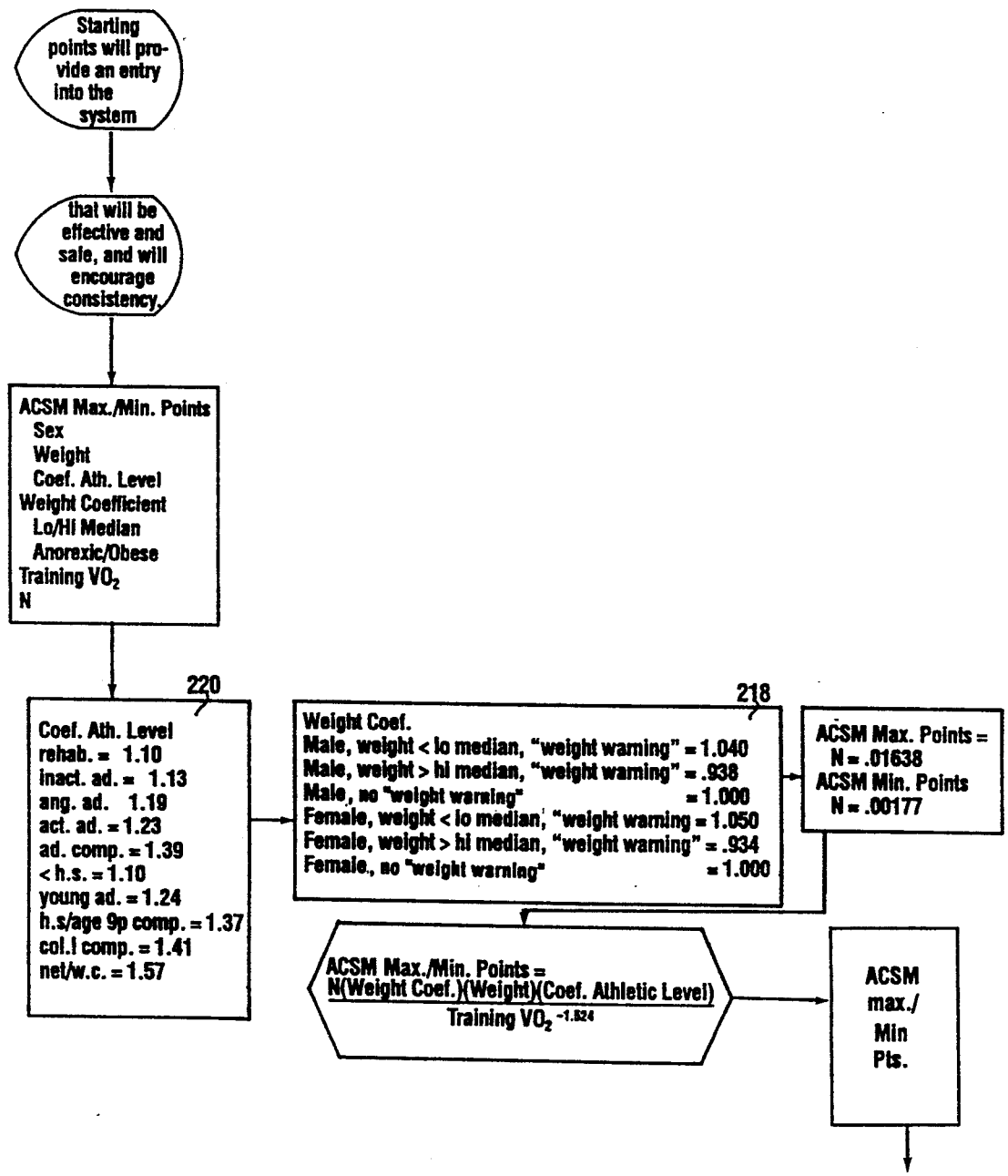
Figure 9A:
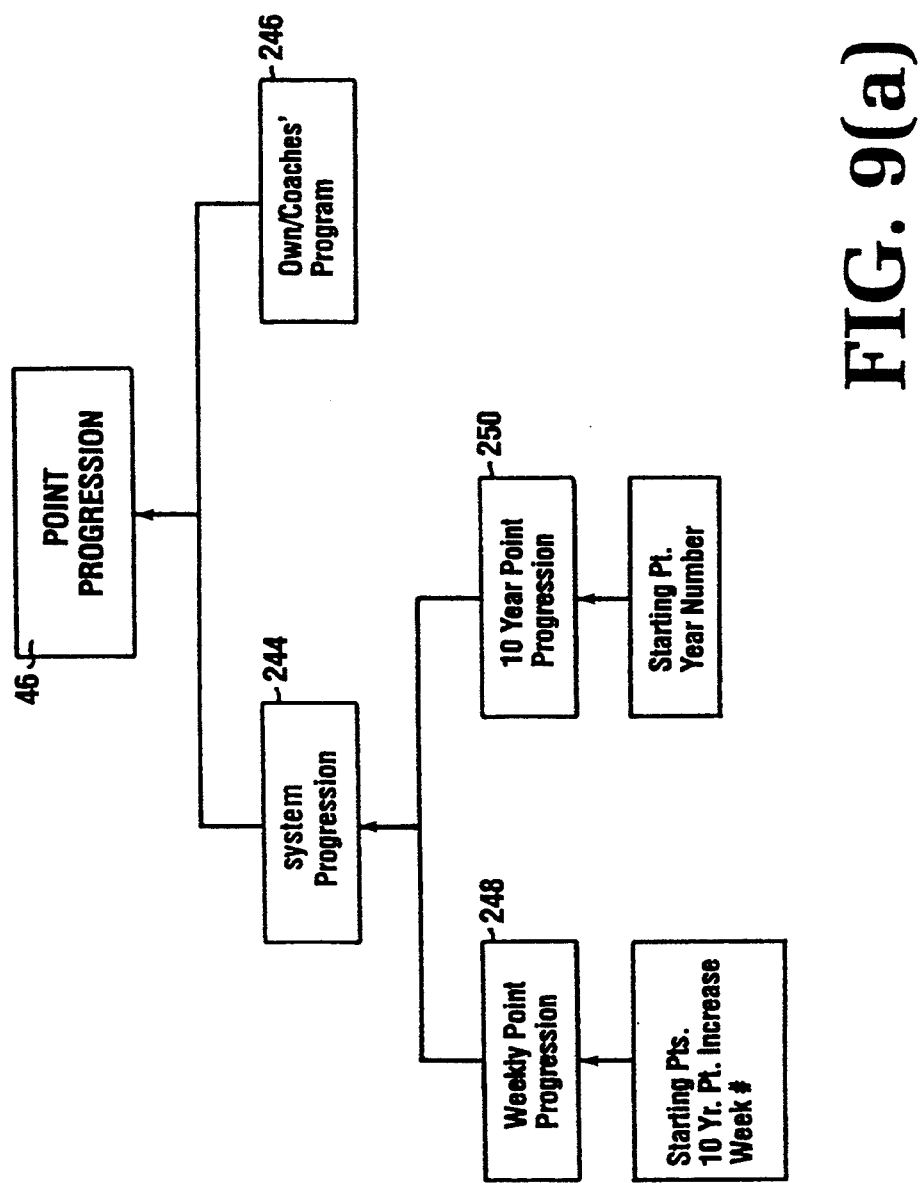
FIG. 9(a) is an overview of the Point Progression, Section of the resident software.

Choices available for setting the starting points 44 are shown generally, by overview, on FIG. 8(a), and comprise estimate from autobiography 214, activity pattern 216, and typical week 218. The flowchart for this selection is set forth on FIG. 8(b).

Figure 8C:
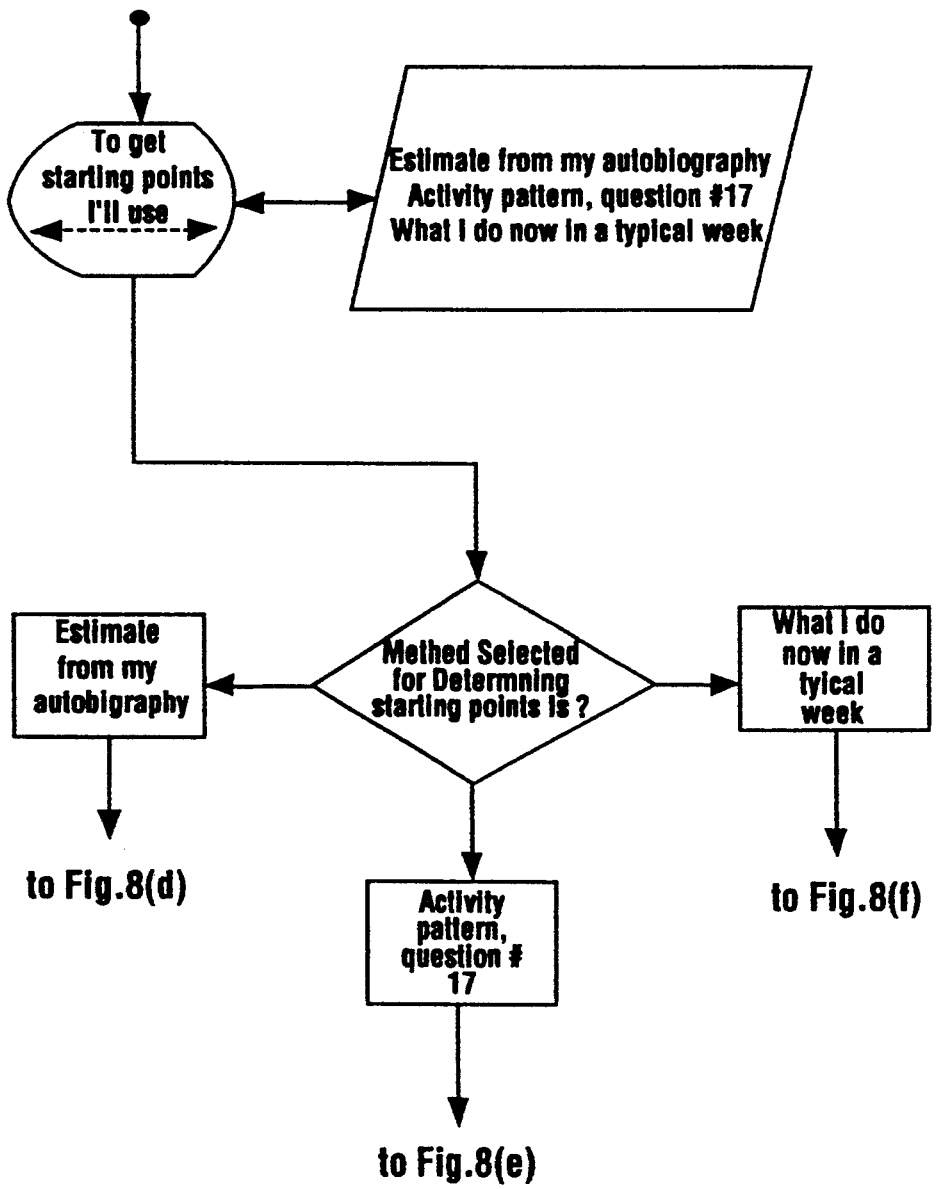
Figure 8D:
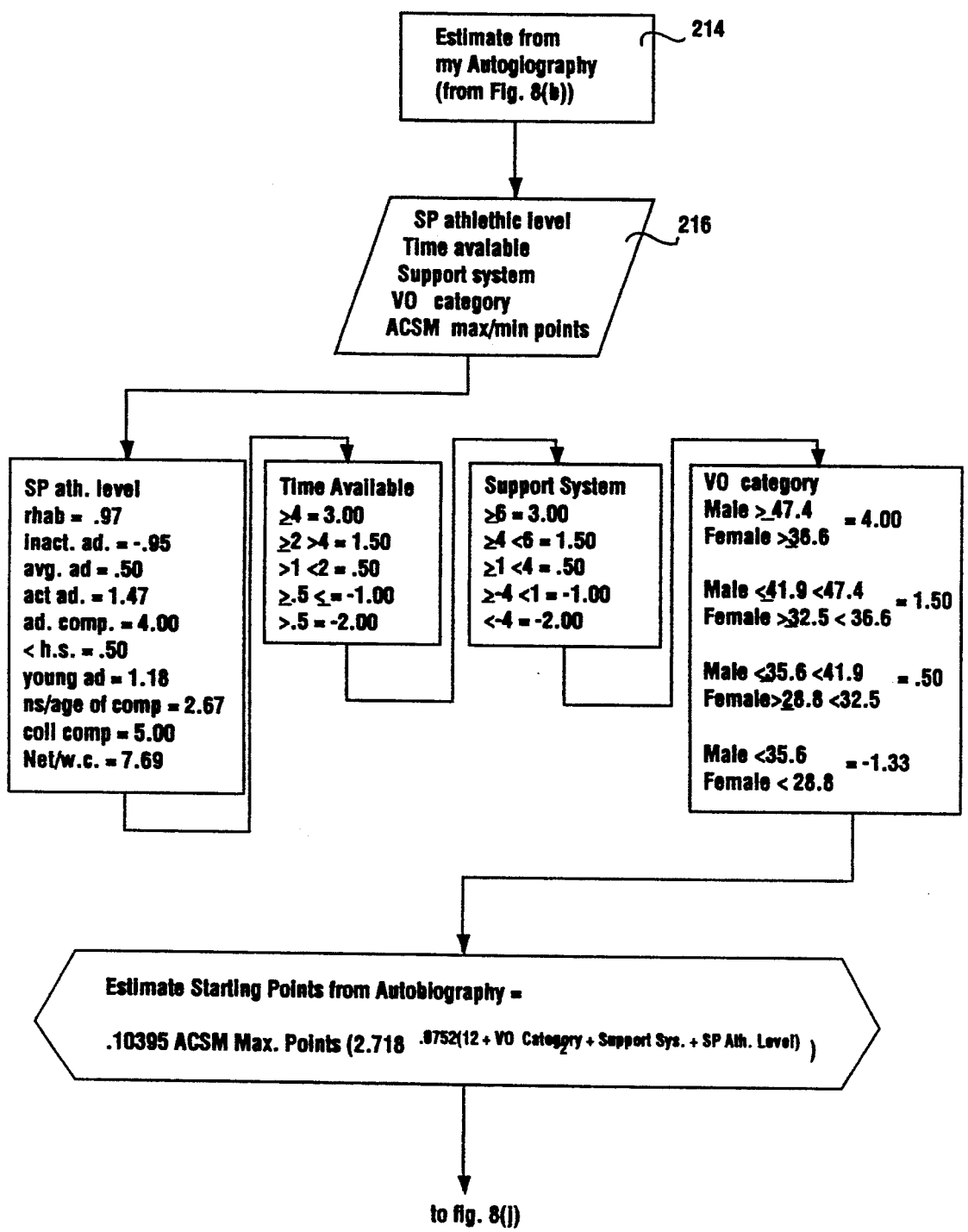
Figure 8E:
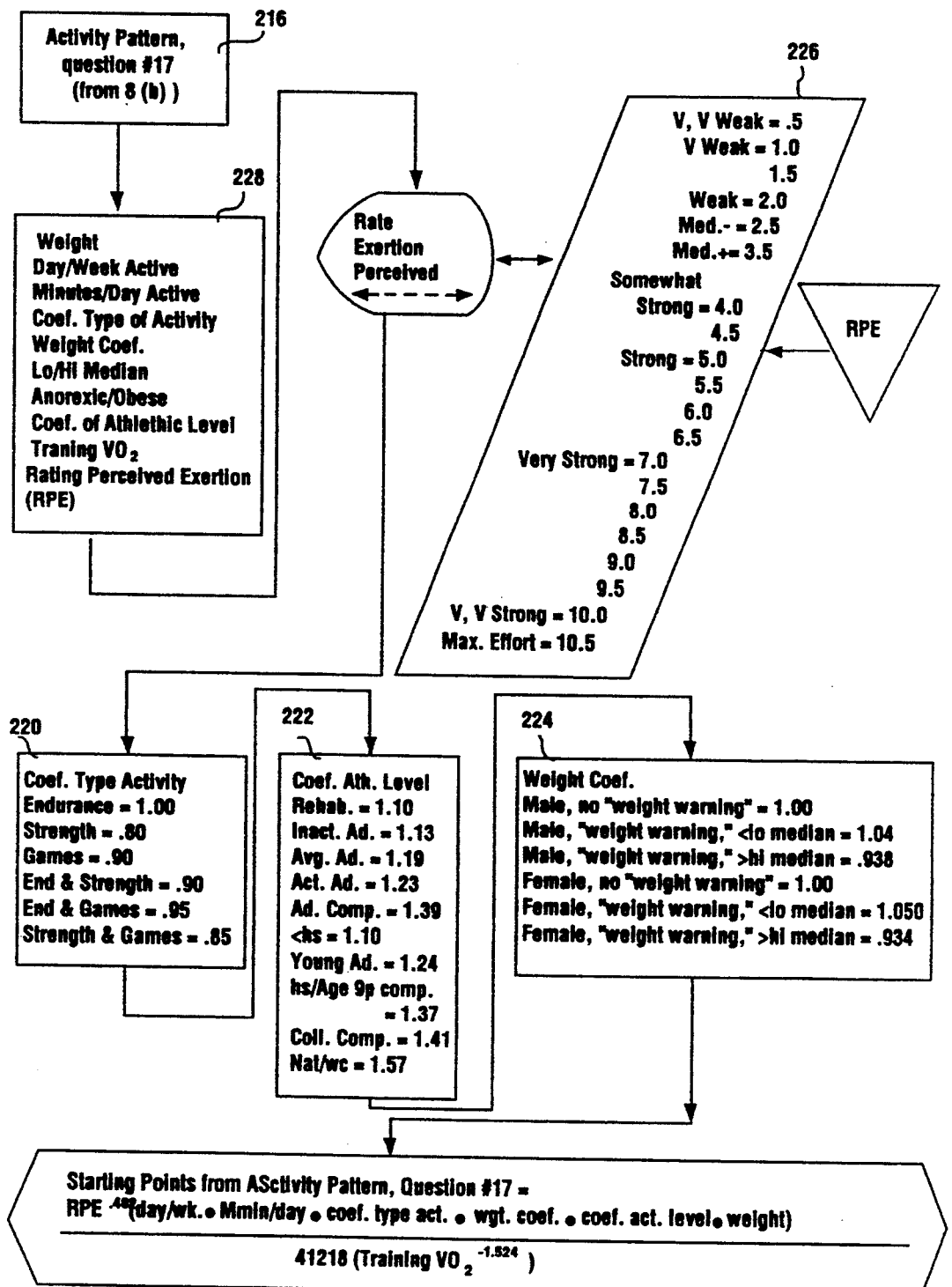
Figure 8F:
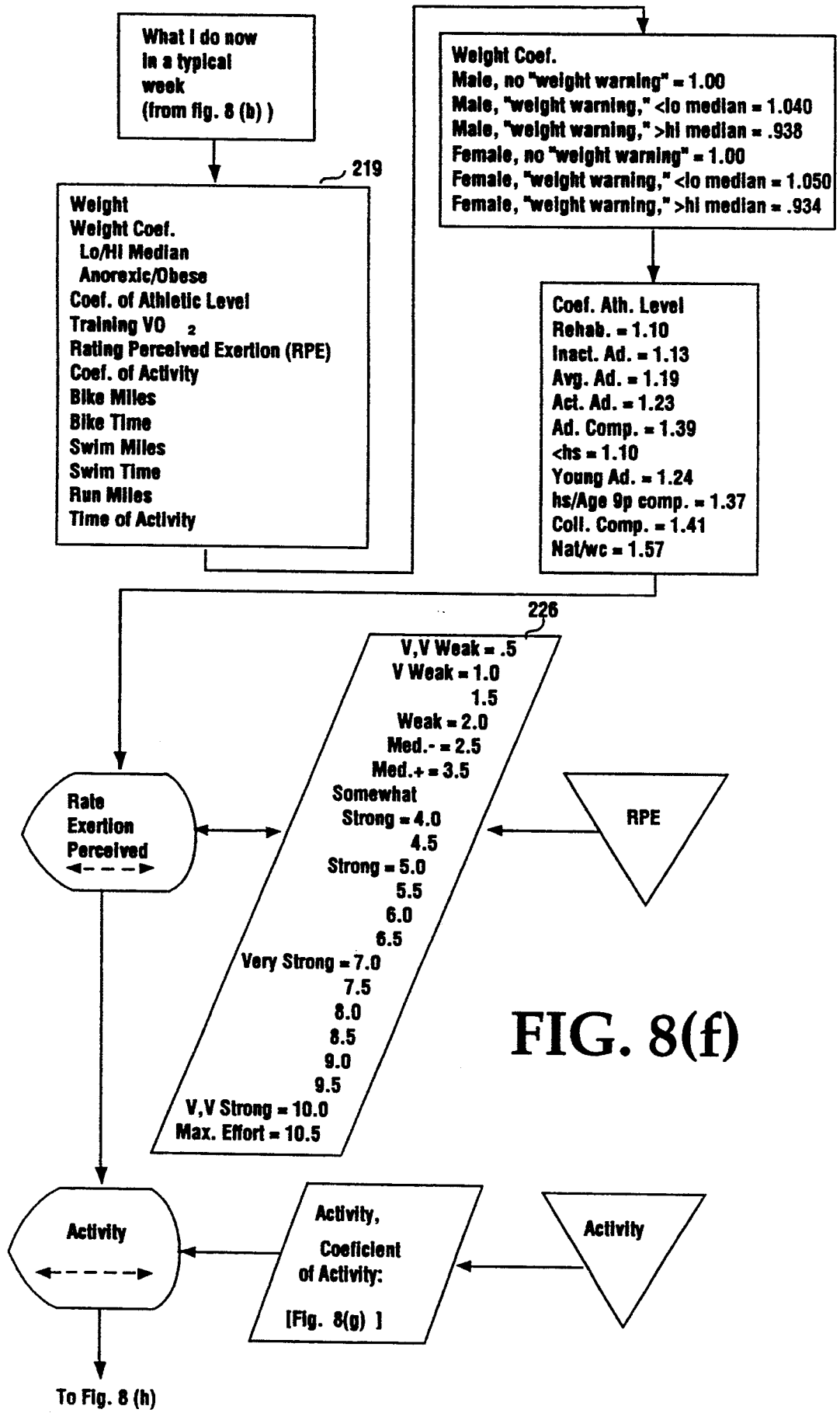
Figure 8H:
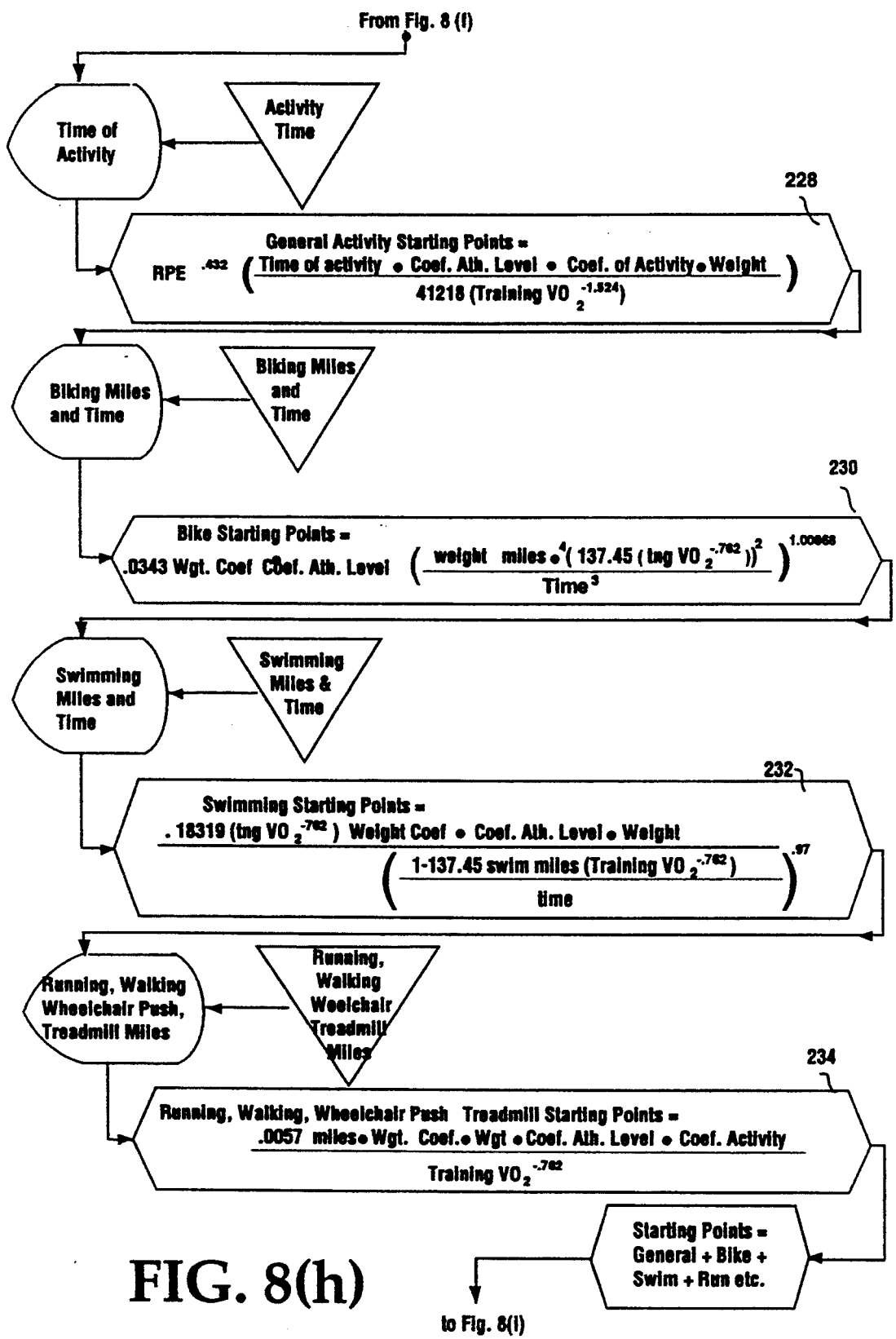

If the user selects the estimate from autobiography 214, the determination of starting points is arrived in accordance with the formulas set forth on FIGS. 8(c) and 8(d). Information for this computation is received from various section above, as shown in box 214. [ACSM mean American College of Sports Medicine, which sets forth exercise guidelines for minimum and maximum exercise which has been used, as set forth herein, as a partial basis for the activity point system.] The formulas shown in FIGS. 8(c) for determining ACSM max and min points) are combined with the formula in FIG. 8(d) to determine the starting points from autobiography:

5.1.1.5.3 *ACSM* Max Points =

-continued $$\frac{.01638(\text{weight coef}) \times (\text{weight}) \times (\text{coef.ath.level})}{\text{training VO}_2^{-1.524}}$$

5.1.1.6 ACSM Min Points =

$$\frac{.00177(\text{weight coef}) \times (\text{weight}) \times (\text{coef.ath.level})}{\text{training VO}_2^{-1.524}}$$

Weight Coef. = .934 to 1.040 (see box 218, FIG. 8(c))
Coef.ath.Level = 1.10 to 1.57 (see box 220, FIG. 8(c))

After completion of the ACSM Min and Max points (FIG. 8(c)), the starting points are estimated in accordance with the formula set forth in FIG. 8(d), as follows:

5.1.1.7 Estimate Starting Points from Autobiography=0.10395ACSM max pts[2.718^{0.0753}(12+VO2-cat.+time+supprt+spath]spath level=0.95 to 7.69

If starting points 44 is determined by typical week 218, resort must be had to determining the coefficients of activity, set forth in FIG. 8(g). These coefficients have been determined by me based on literature of metabolic expenditure or metabolic rate during these activities. Consequently, they depend from intensity; assuming the same intensity across the board, the coefficients of activity (FIG. 8(g)) are rated based upon the highest effort required.

Effort required and the coefficients of activity (FIG. 8(g)) are only a portion, albeit critical, of the overall exercise picture. In the case of starting points 44 being determined by activity pattern 216, it is important to include a coefficient for the type of activity 220, coefficient of athletic level 22, with coefficient 224 and rating of perceived exertion ("RPE") 226. These are based on answers and information supplied by the user, the source of which is identified in box 228. Starting points from activity pattern 216 are determined in accordance with ,the formula set forth in FIG. 8(e), as follows:

5.1.2.3 Starting Points from Activity Pattern =

$$\frac{RPE^{.432}(\text{day/wk} \times \text{min/day} \times \text{c.type act} \times \text{wt coef} \times \text{c.a.level} \times \text{wt})}{41218(\text{training VO}_2^{-1.524})}$$

If typical week 218 is selected for determining starting FIGS. 8(a and f). Calculations are made for general activity starting points 228, bike starting points 230, swimming starting points 232, and running, walking, wheelchair push, treadmill starting points 234, and summed 236 to give total starting points.

5.1.3.1 General Activity Starting Points =

$$\frac{RPE^{.432}(\text{Time} \times \text{wt coef} \times \text{coef ath level} \times \text{wt} \times \text{coef act})}{41218(\text{training VO}_2^{-1.524})}$$

5.1.3.2 Bike Starting Points = .0343 wt coef ×

$$\text{coef ath level} \left[ \frac{(\text{weight}(\text{miles}^4)(137.45(\text{tng VO}_2^{-.762}))^2}{\text{Time}^3} \right]^{1.00868}$$

5.1.3.3 Swimming Starting Points =

-continued $$\frac{18319(\text{training VO}_2^{-.762})\text{wt coef} \times \text{coef ath level} \times \text{sex wt factor}}{\text{Time}^2} \left[ 1 - \frac{137.45 \text{ miles}(\text{tng VO}_2^{-.762})}{\text{Time}} \right]^{.97} \cdot \text{weight}$$

5.1.3.4 Running, walking, wheelchair push, treadmill Starting $$\text{Points} = \frac{.0057 \text{ miles} \times \text{wt coef} \times \text{wt coef ath level} \times \text{coef activity}}{\text{training VO}_2^{-.762}}$$

Figure 8I:
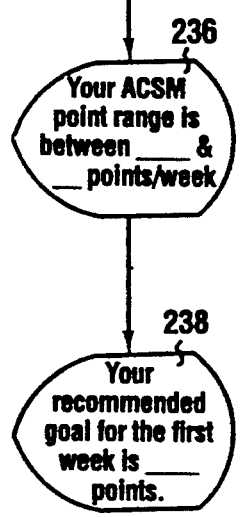

As shown on FIG. 8(i) starting points, whether they are determined from an estimate from the autobiography 214, from the activity pattern and response to question number 17 (in which the user has imputed the kinds of activities and levels he's involved in), or based on a typical week 218, FIG. 8(a), it's point ranges then set forth, based on the ACSM max/min points, screen 236 and FIG. 8(i), and the recommended goal for the first week is set forth in screen 238 on FIG. 8(i), from the starting points.

"ACSM" refers to the American College of Sports Medicine (ACSM) which issued suggestions for minimum activity. However, ACSM did not use the variables of the individual, the activity, or the environment for determining these numbers. ACSM simply said that a person should work between 20 minutes, three times a week to one hour, five times a week. By the foregoing equations, these values have been converted to pinpoint the individual's specific exercise program.

Figure 9B:
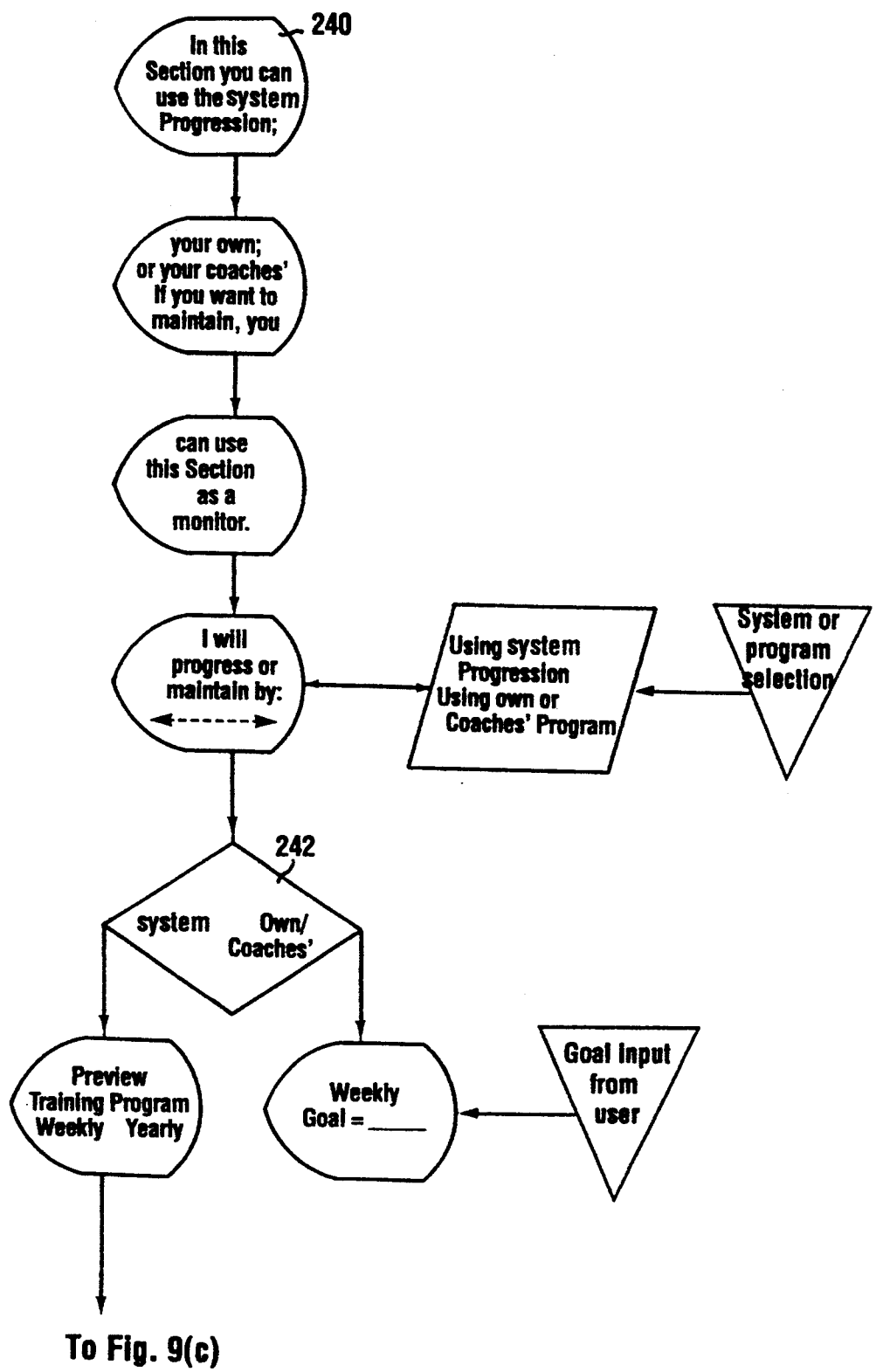
FIGS. 9(b) and 9(c) are flow charts of the Point Progression, Section 6.

Progress or point progression 46 can then be selected by the user, as shown in FIG. 3. If the user, immediately after completing the starting point 44, presses the escape 28 (FIG. 2) and moves the cursor to the right using cursor control 26, the user will enter progress 46. If the user presses enters progress 24, the user will then enter the point progression Section 6 (FIG. 9(a)). The point progression section tells the user in screen 240 (FIG. 9(b)) that the operation of the progression can now be used thereby using the program as a monitor. Under the program, the user may choose between a progression program set by the computer, or his own desired progression, or a coach's assisted progression. Thus, decision box 242 in FIG. 9(b) provides the selection. The "mentor" progression 244 and the "own/coaches" program 246 are set out in general terms in FIG. 9(a). If the user chooses progression 244, the user may see a weekly point progression for weekly monitoring, based on daily entries, or a ten year point progression, boxes 248 and 250 respectively in FIG. 9(a). Thus the user may preview the program, even over a ten year period. It must be understood that as the user progresses through a consistent activity, the user's basic variables will change and therefore the program is continually adjusted, just as a coach or physiologist would adjust the program based on progress. Consequently if the user has selected the progression program 244, the schedule is set into the computer to be used for weekly goal points.

Figure 9C:
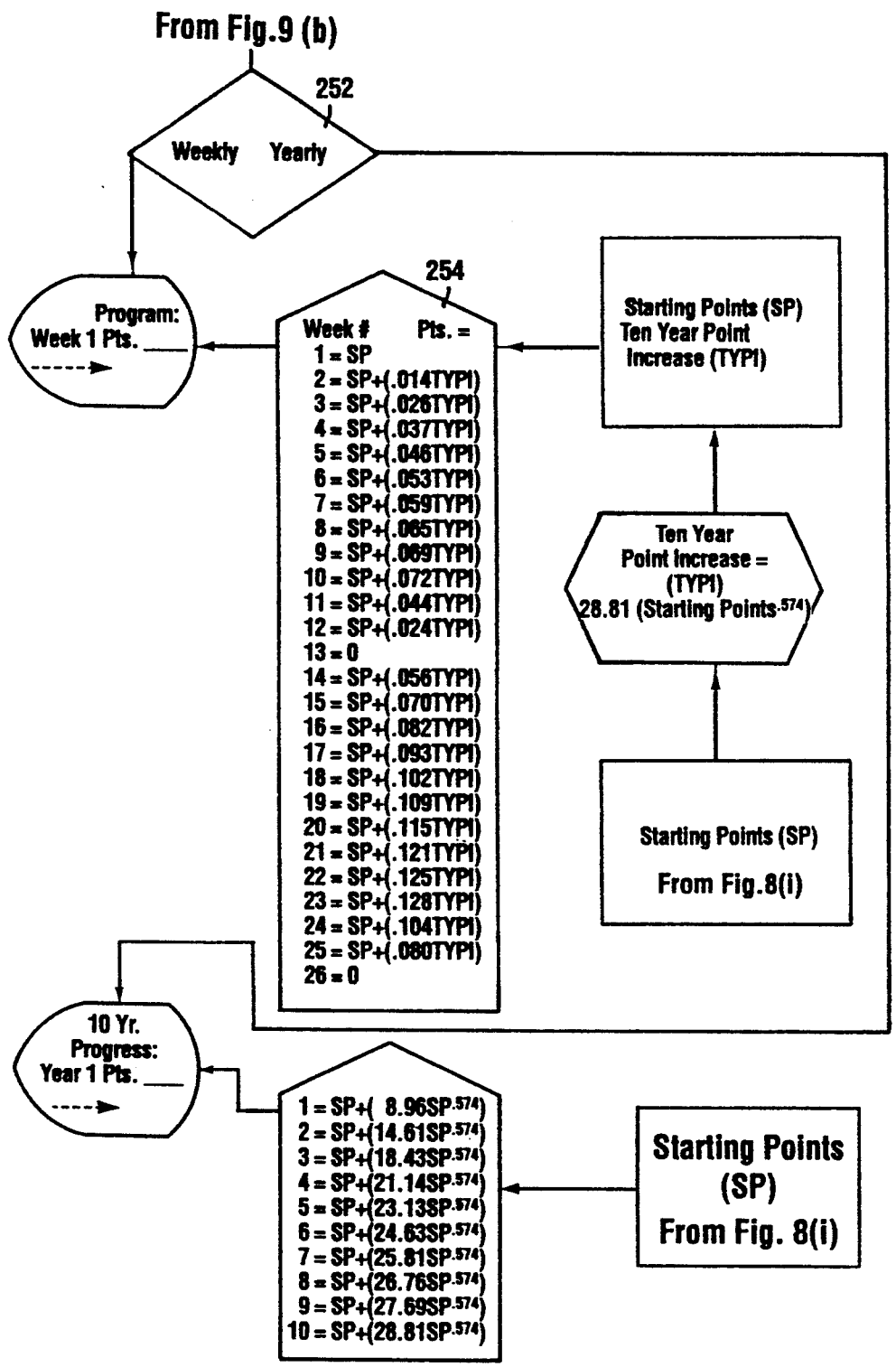

The next decision after selection of progression 244 or program 246, is decision box 252, on FIG. 9(c), which allows the user to determine whether a weekly program is sought to be reviewed or a ten year program is sought to be reviewed. As is shown in box 254 in FIG. 9(c), the week number point determination is based upon the variables of the starting point and the "TYPI" the ten year point increase The formulas for these determinations are set forth in FIG. 9(c) and repeated below:

Section 6  Point Progression
6.1.1  Weeks 2–25 = Starting Points + A(TYPI)
        A = .014 to .128
        TYPI = 28.81 (starting points$^{.574}$)
        Week #1 = SP
        Weeks #13 & 26 = 0
6.2.1   Points at end of years 1 to 10 =
        starting points + B (starting points$^{.574}$)
        B = 8.96 to 28.81

The information previewed and provided pursuant to Section 6, is merged under the diary section, which includes the daily use, most typically used by the user after completion of the start 32 (FIG. 3). As stated above, start 32 is utilized to initialize the system to the particular parameters of the user. Consequently at this juncture, the system has been set to the user's individual and independent needs and exercise regime, the program points have been established, and the user can then move the cursor to the diary section and press enter, at which point the day, date and day of the week will be displayed. The user may then press enter again, at which point the user will be able to choose between recovery indicators 48, daily points 50, daily status 52, and end of week 54 (FIG. 3).

Figure 10A:
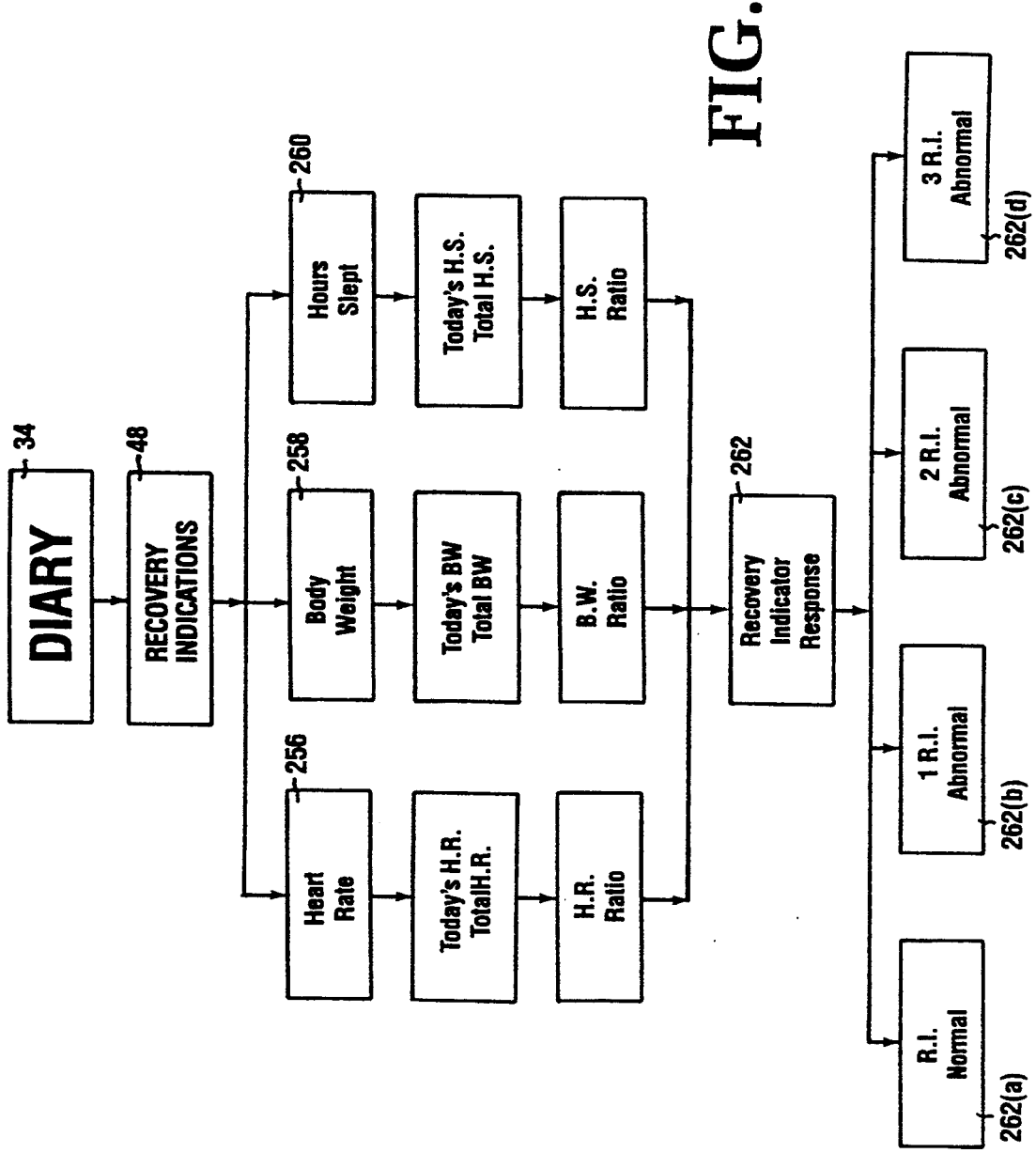
FIG. 10(a) is an overview of the Recovery Indicators of the Diary, Section 7.
Figure 10B:
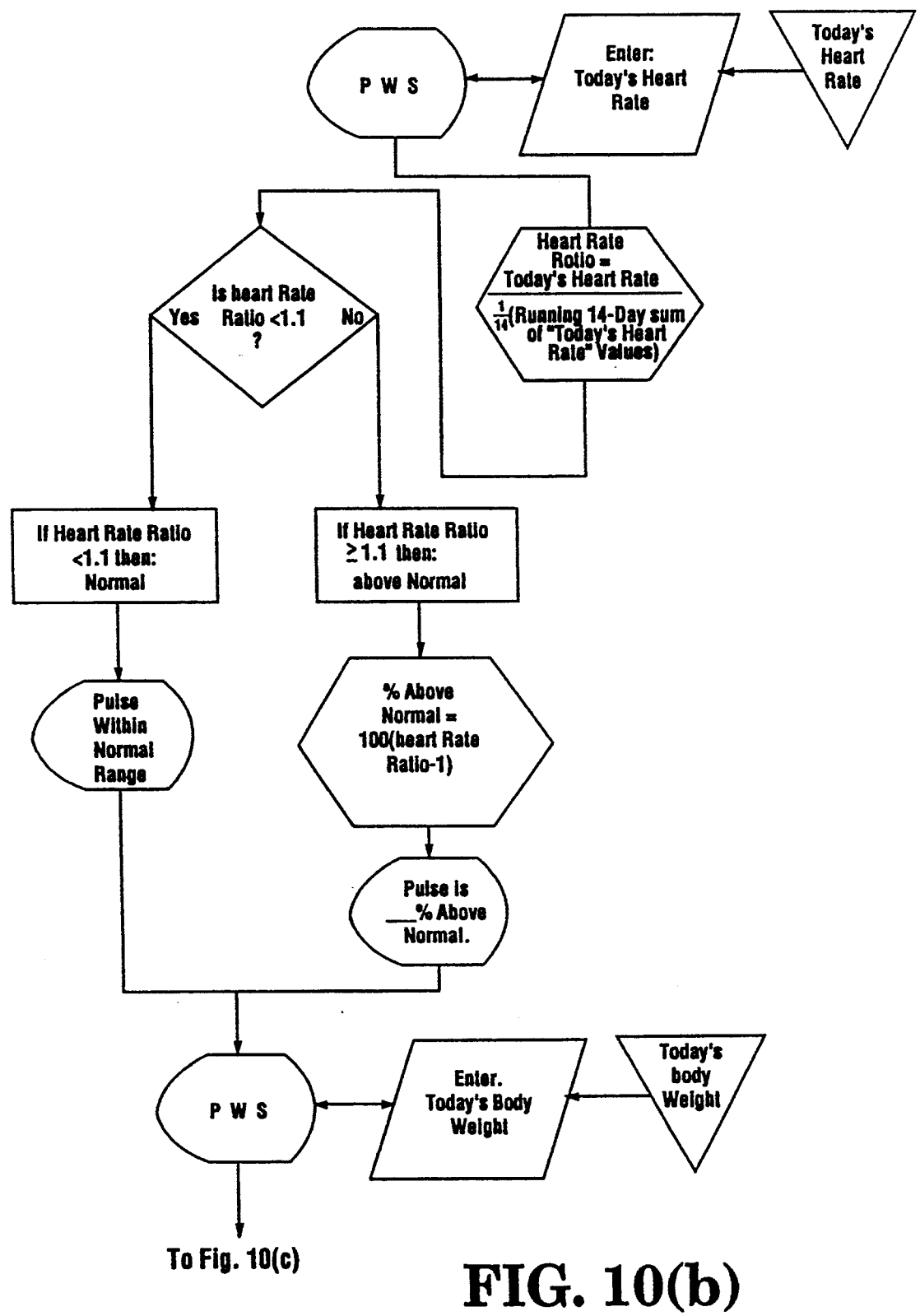
FIGS. 10(b) through 10(d) are flow charts of the Recovery Indicators, Section 7.
Figure 10C:
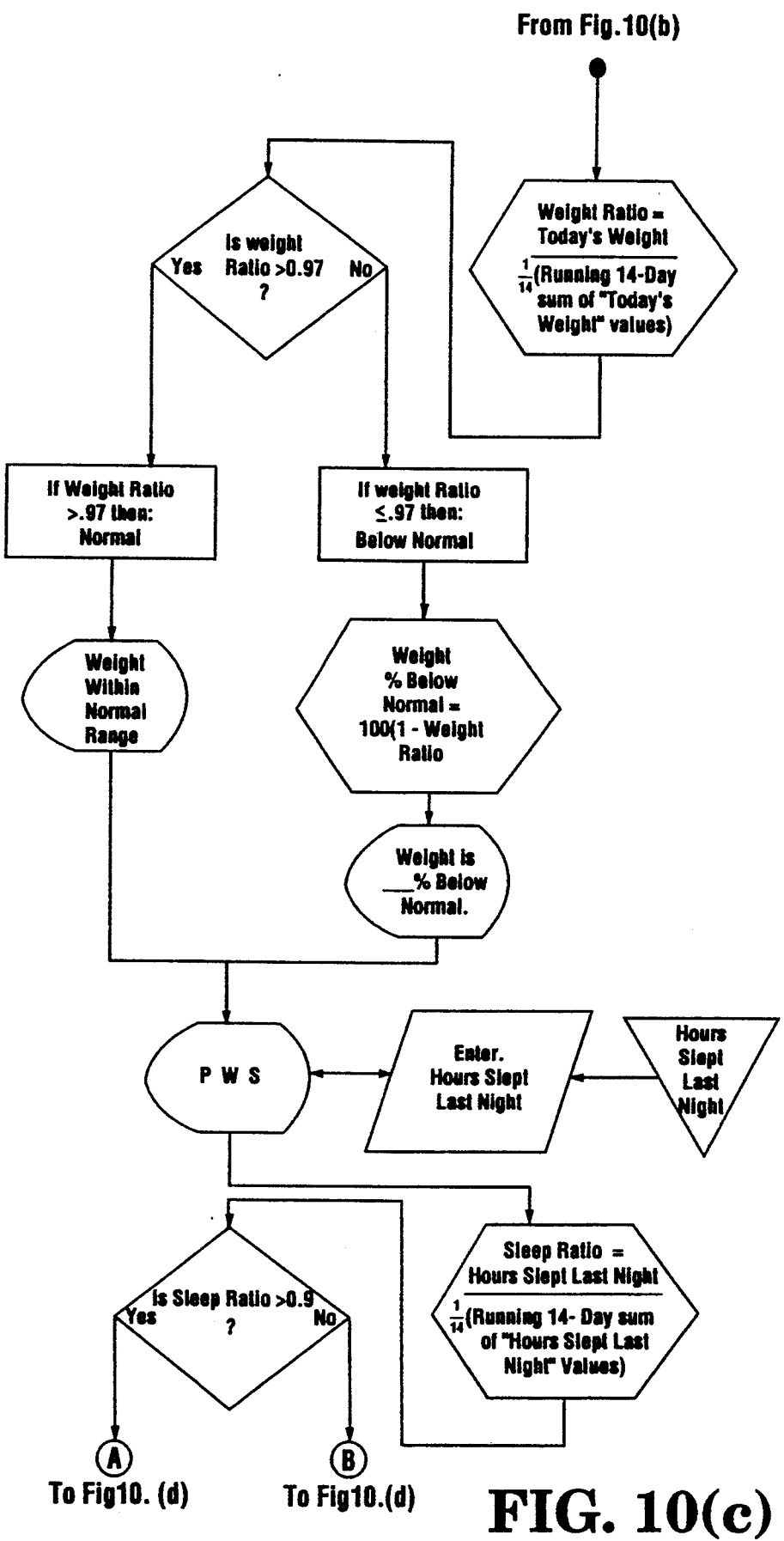
Figure 10D:
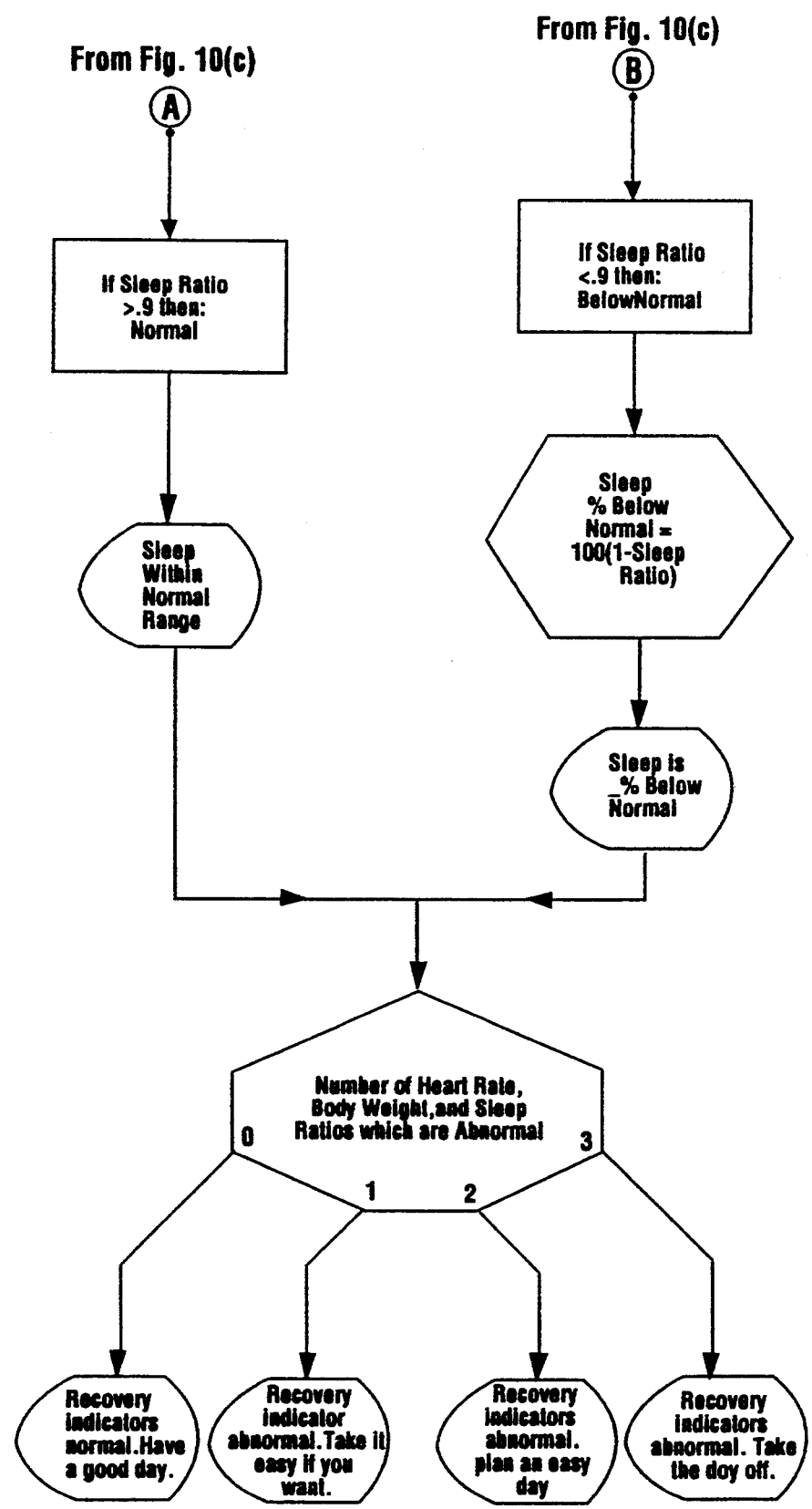

General overview for the diary 34 and recovery indicators 48 are set forth on FIG. 7(a), and the flow charts for recovery indicators 48 (Section 7) as set forth in FIGS. 10(b) through 10(d). The recovery indicators, as their name implies, are indicators of recovery from recent challenge or stress. They are predicated upon research, and include the morning heart rate which the user gauges before getting out of bed (box 256, FIG. 10(a)), the morning body weight nude, after the user voids and before eating (box 258, FIG. 10(a)), and the user's subjective evaluation of how many hours the user believes were slept (box 260, FIG. 10(a)). These pieces of information are all analyzed, and based on a running average, the daily indicators are compared with the average indicators. If the daily indicators indicate a normal range, the user is given a message essentially stating that the recovery indicators are normal. If one recovery indicator is abnormal the user is advised to take it easy, if the user feels that he should. If two recovery indicators are abnormal the user is asked to plan an easy day, and if three recovery indicators are abnormal the user is asked to take the day off. This recovery indicator response 262 is chosen from the four choices 262(a) through (d), FIG. 10(a). Heart rate calculation is set forth in FIG. 10(b), rate ratio on FIG. 10(c), and sleep ratio on FIG. 10(c) through 10(d). The particular outcomes set forth as 262(a) through (d) on FIG. 10(a) are set forth at the bottom of FIG. 10(d), and are determined under the formulas set forth in 10(b), (c) and (d), and repeated as follows:

7.1.1 Heart Rate Ratio=Today's heart rate/total heart rate/14% above normal=heart rate ratio−1

7.2.1 Weight Ratio=Today's weight/total weight/14% below normal=100 (1−weight ratio)

7.3.1 Sleep Ratio=Hours slept last night/total hours slept/14% below normal=100 (1−sleep ratio)

Figure 11A:
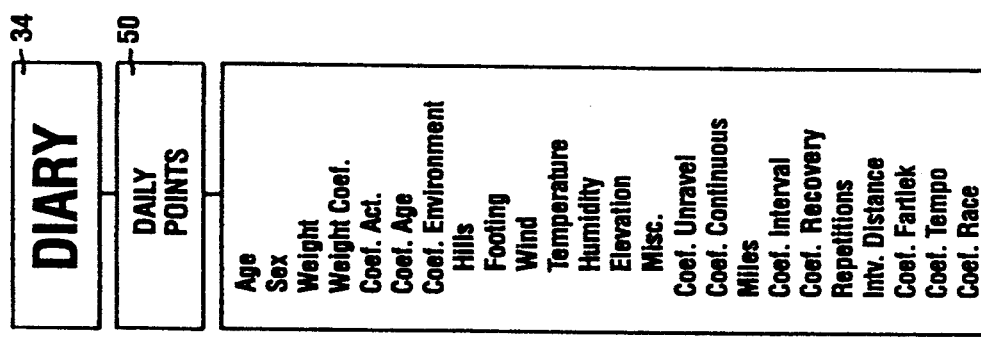
FIGS. 11(a) and 11(b) are an overview of the Daily Points, Section 8 of the Diary of the resident software.
Figure 11B:
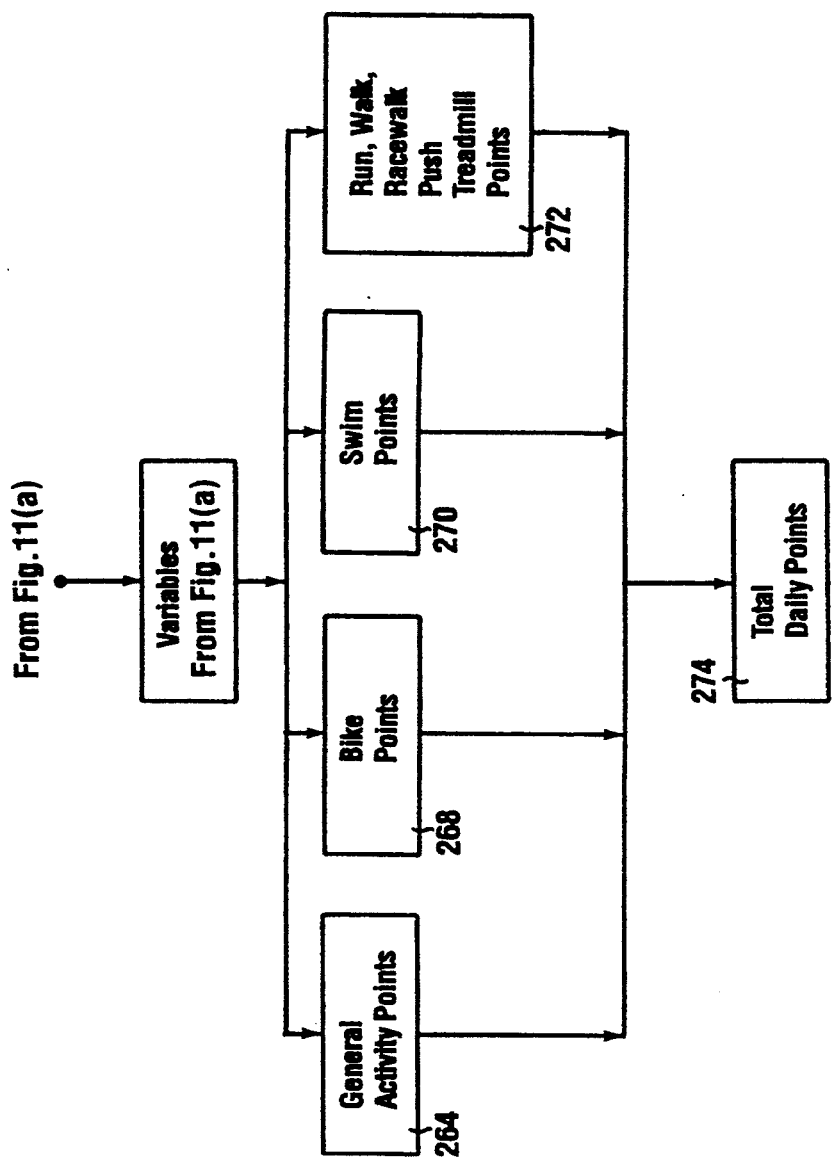
Figure 11C:
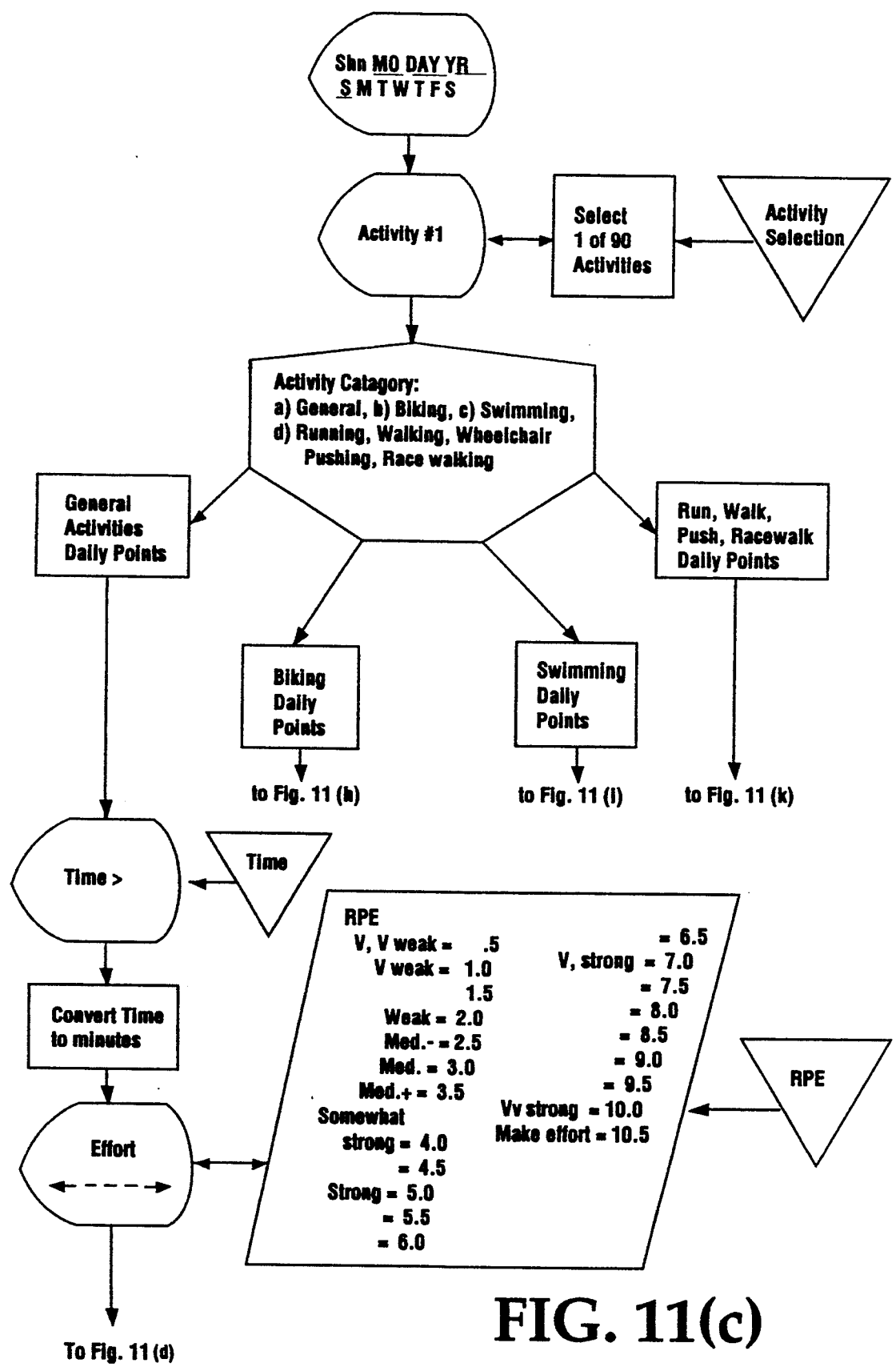
FIGS. 11(c) through 11(l) are flow charts of the Daily Points, Section 8 of the Diary.
Figure 11D:
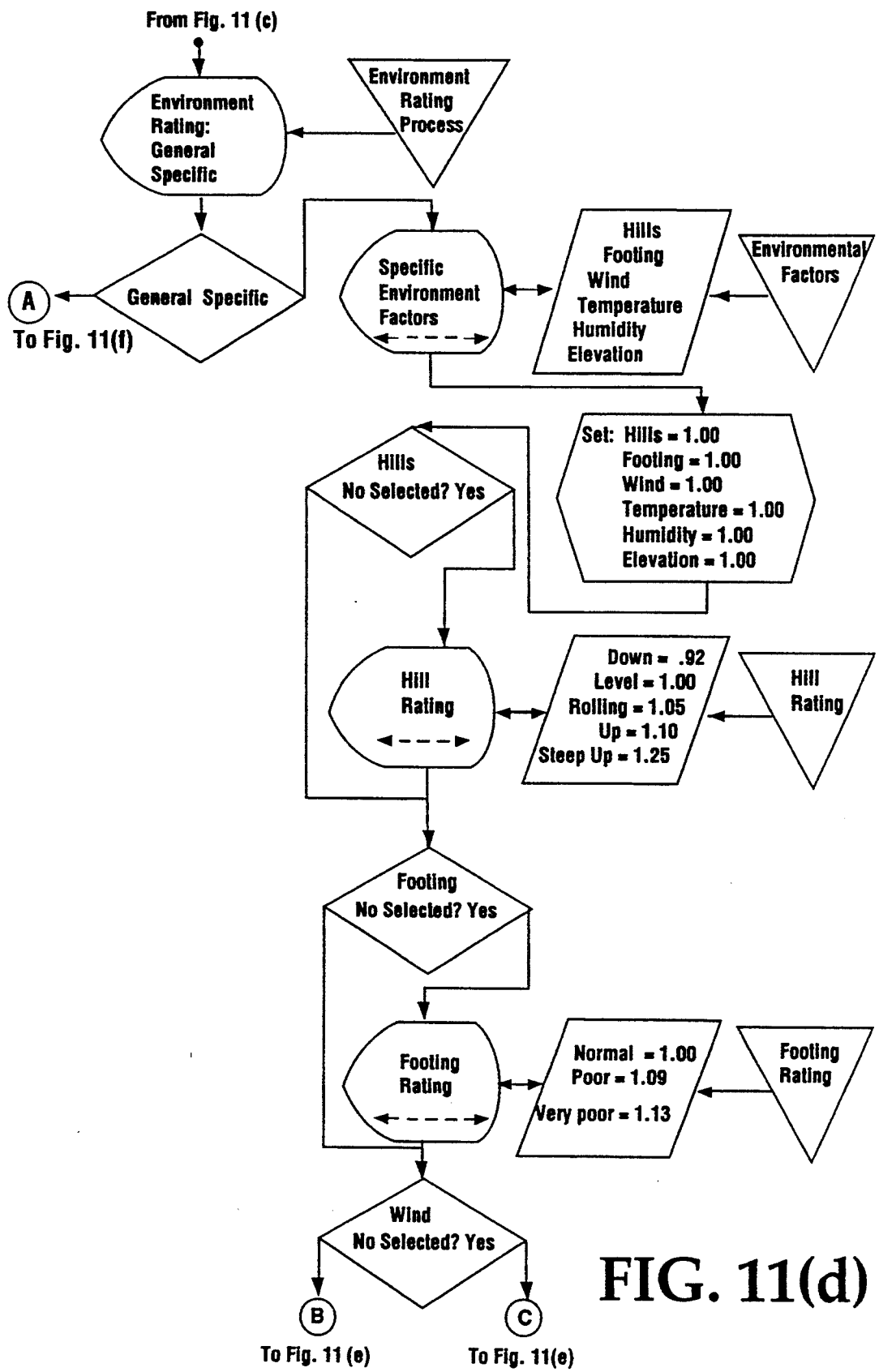
Figure 11E:
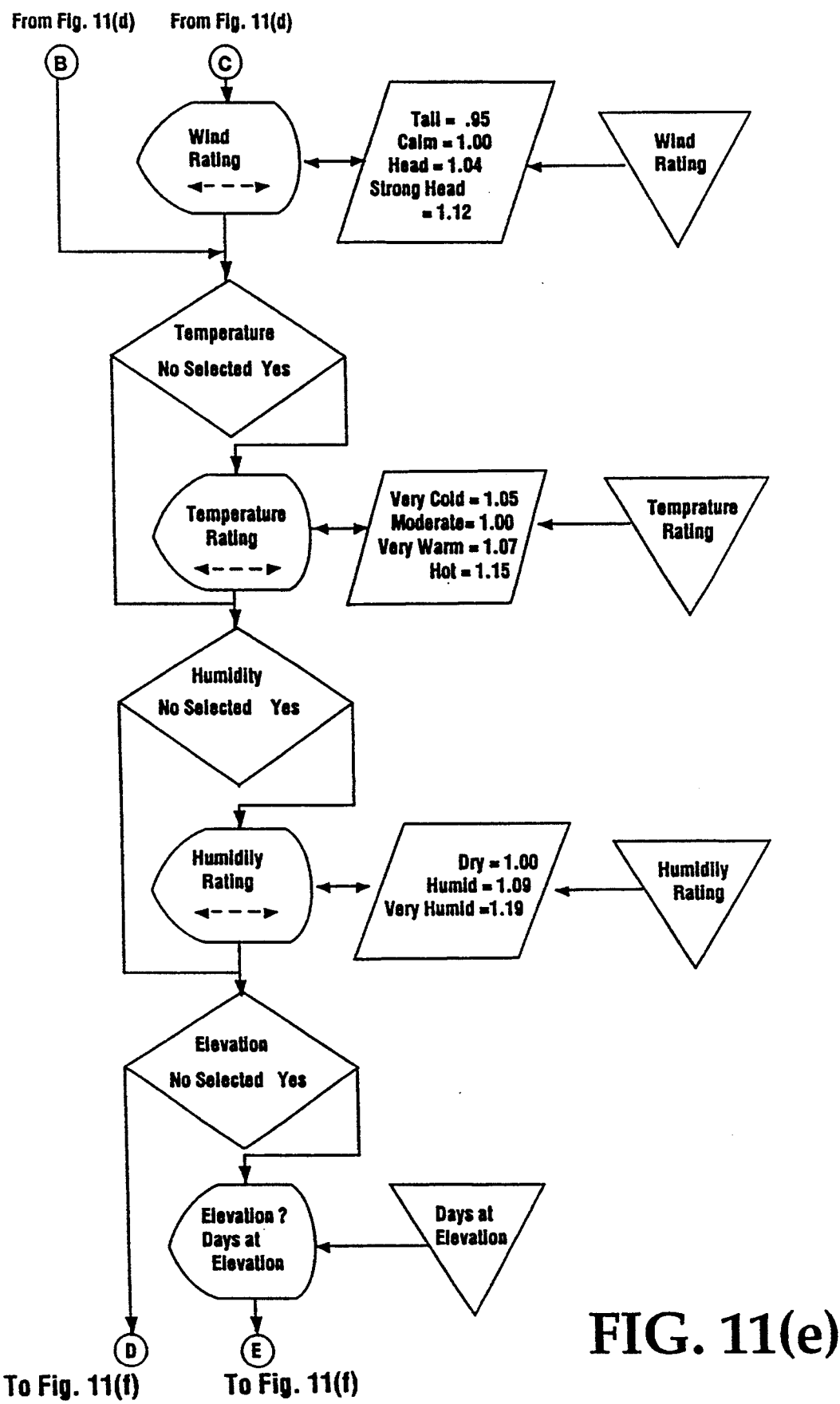
Figure 11F:
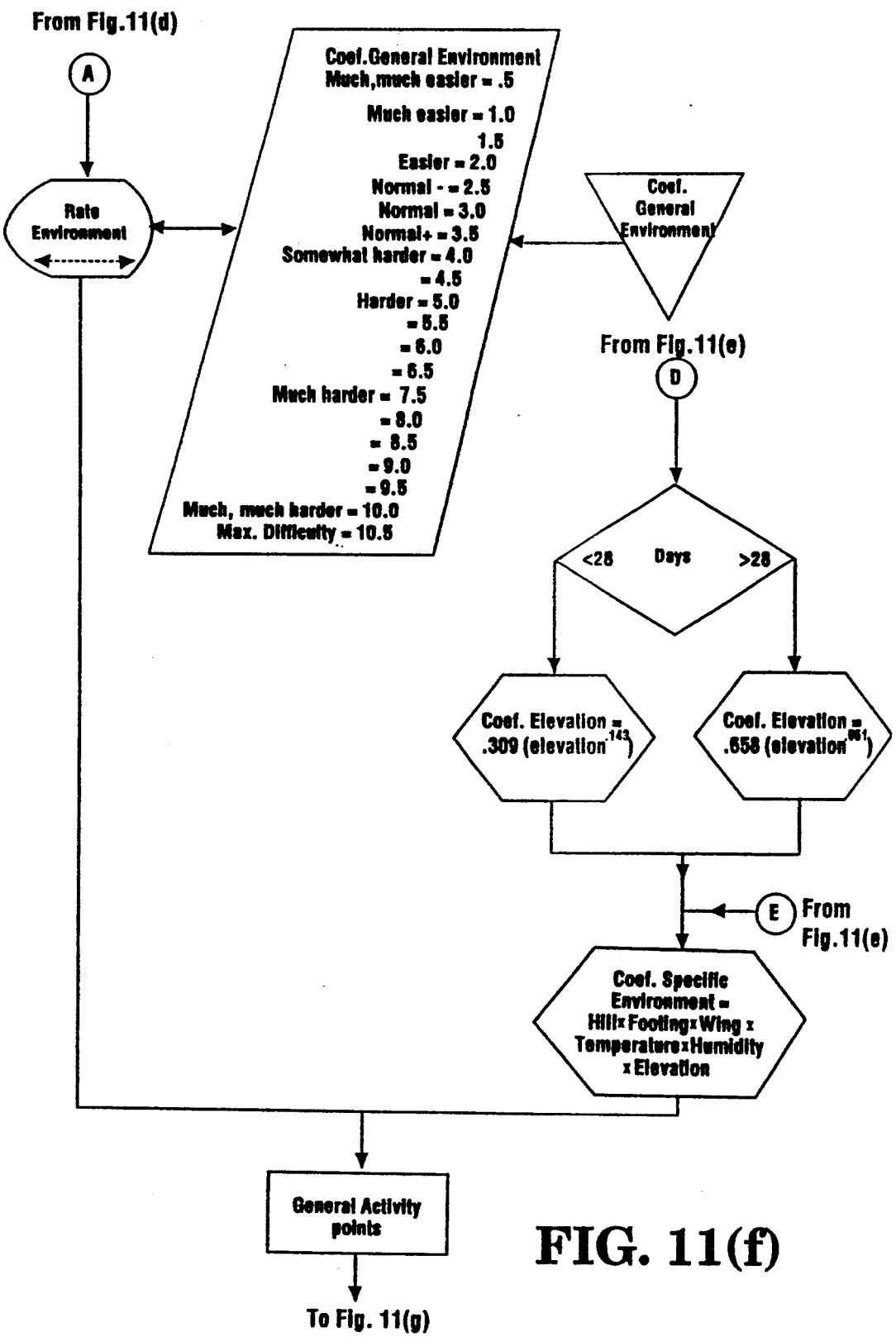
Figure 11G:
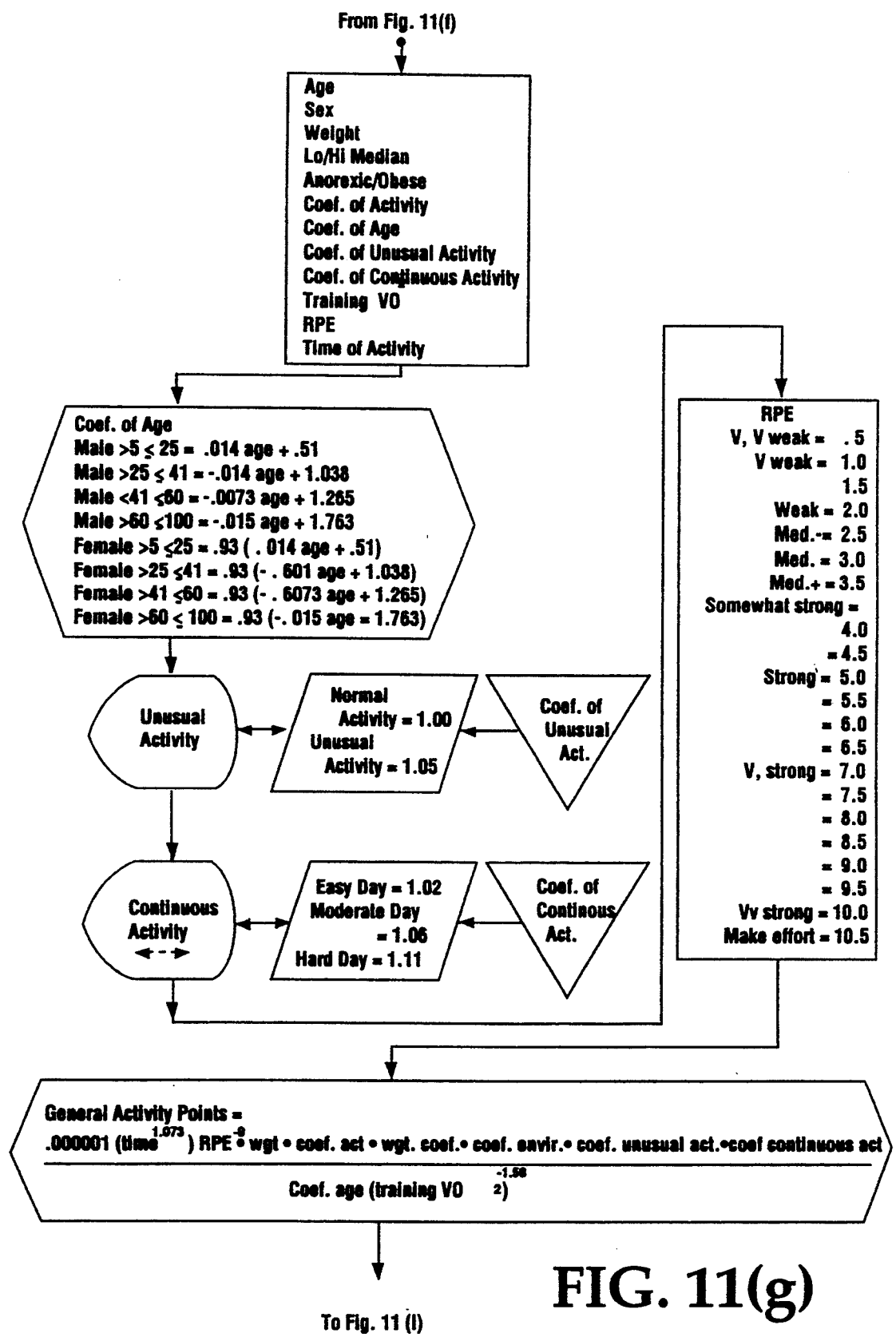
Figure 11H:
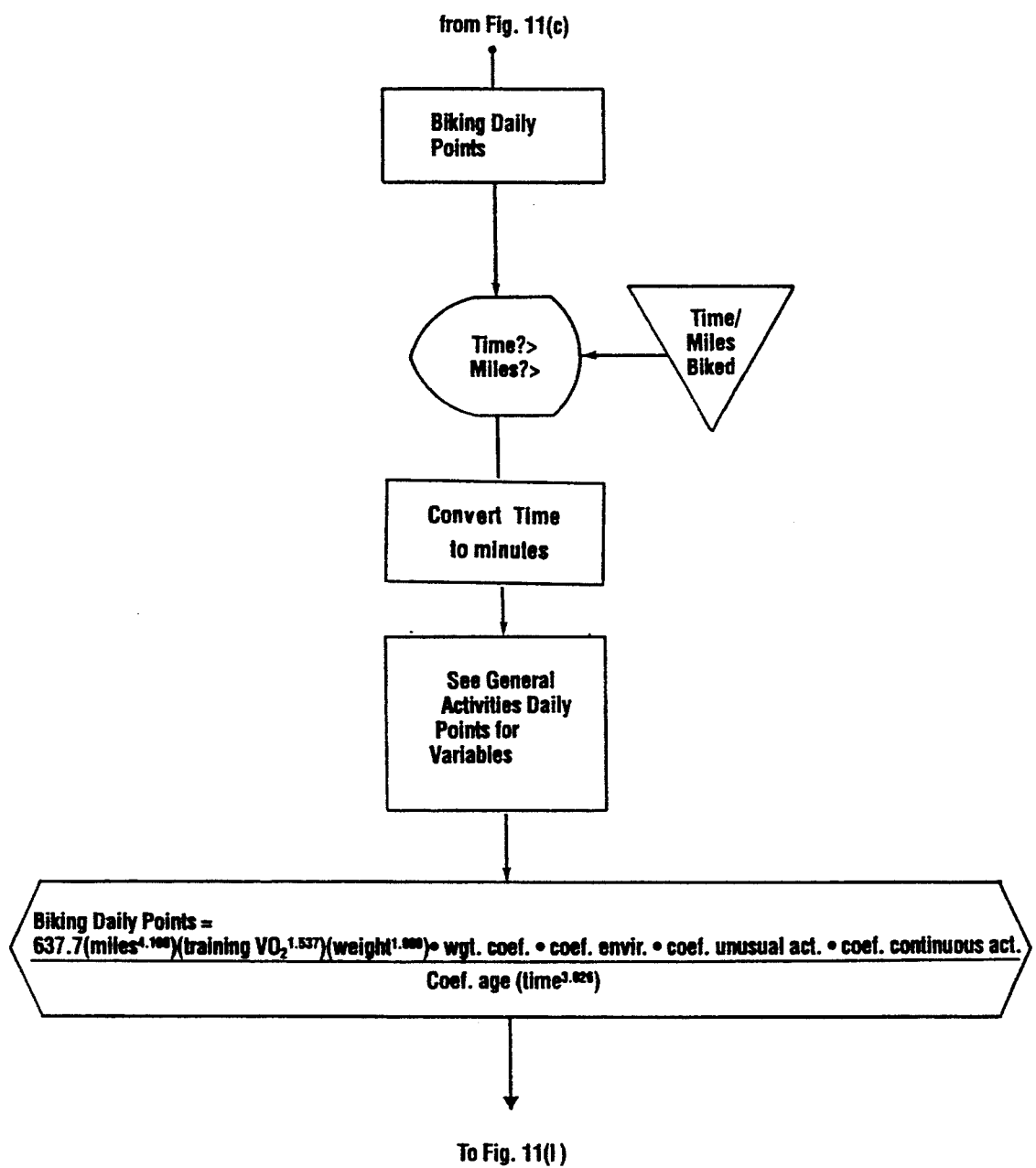
Figure 11I:
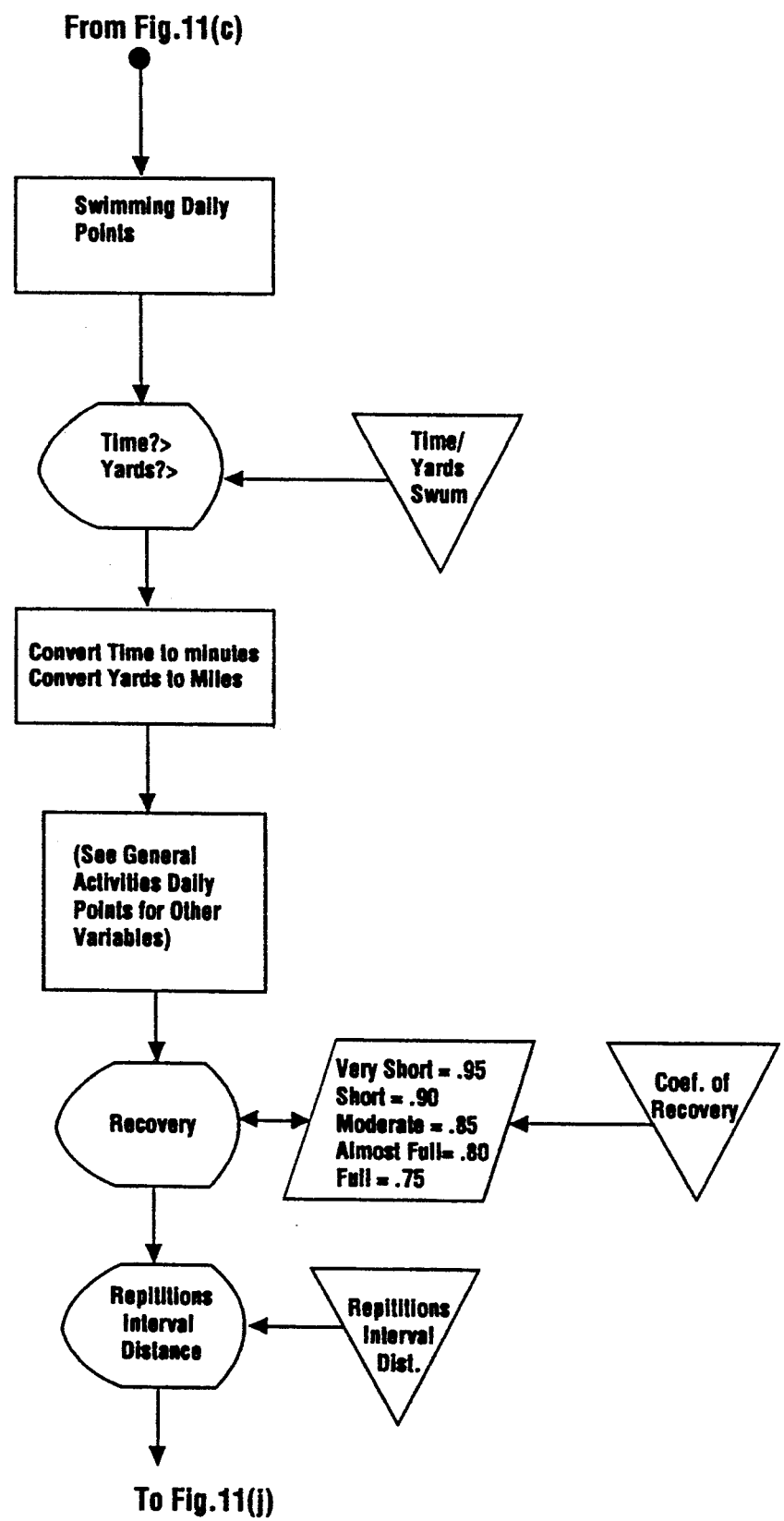
Figure 11J:
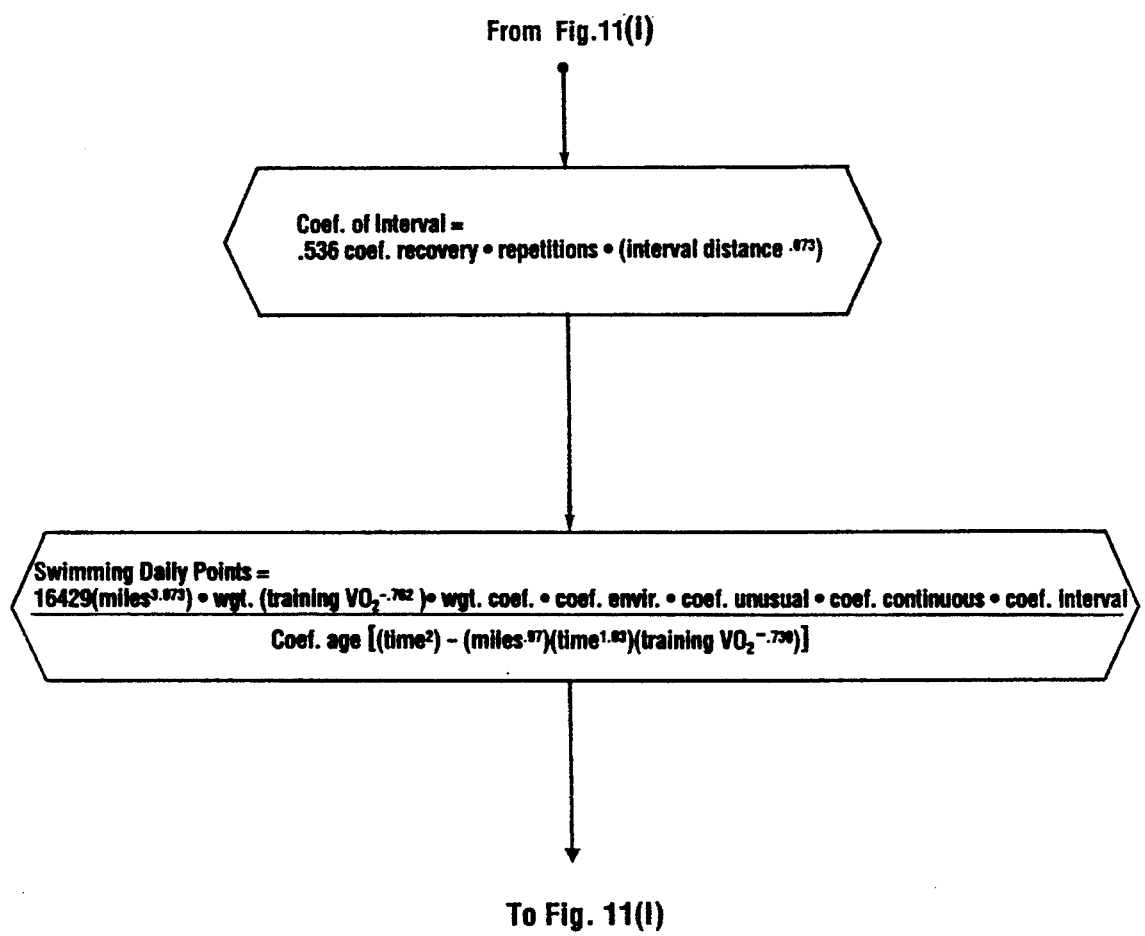
Figure 11K:
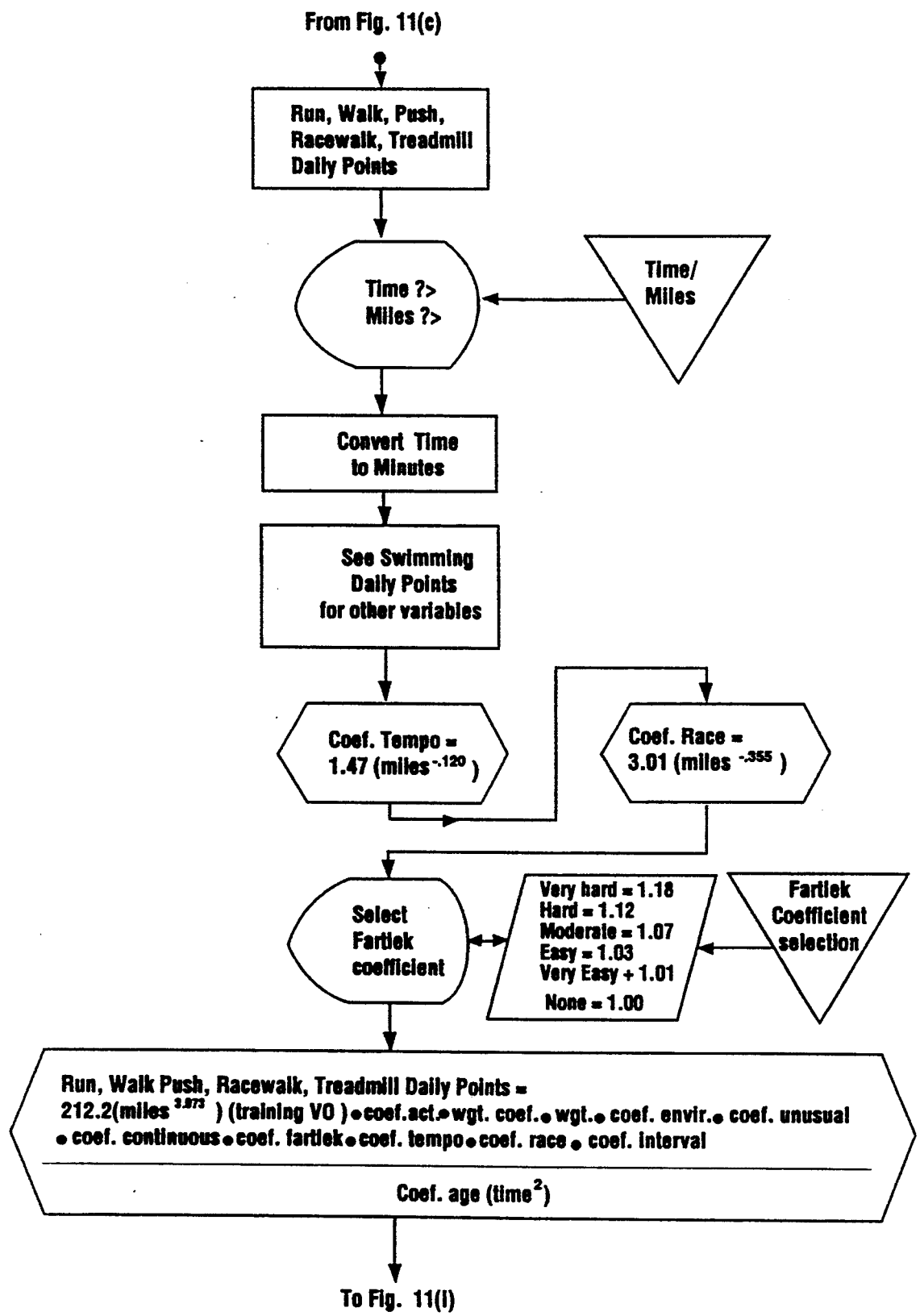
Figure 11:
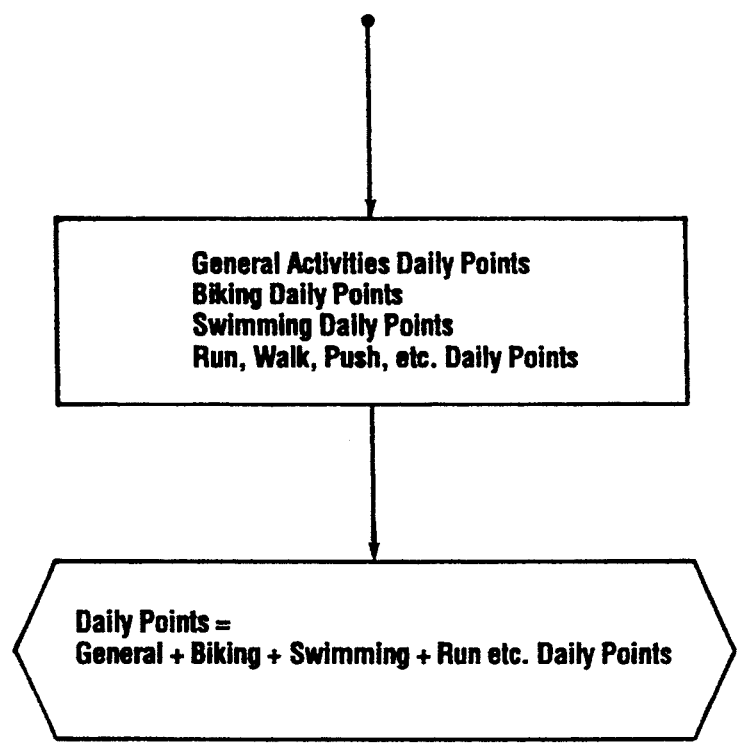

After one completes the recovery indicators 48, the next section, Section 8, is daily points 50 in FIG. 3, set forth in FIGS. 11(a) through 11(l). Daily points 50 is a critical part of the whole program because this is the section that the user is involved in consistently, (along with the recovery indicators), to evaluate the user's daily effort and compare that effort against his goals. The variables in this section, set forth in FIG. 11(a), are age, sex, weight, a coefficient of weight, a coefficient of activity, a coefficient of age, a coefficient of environment, a coefficient of unusual activity, a coefficient of continuous activity, training VO$_2$, coefficient of intervals, a rating of perceived exertion ("RPE"), and duration of activity. From these variables, which are put into a series of complex formulas set forth in the flow charts in FIGS. 11(b) through (k), the user can evaluate the effort of over 90 different activities for himself as an individual in many different types of environments. From the variables listed in FIG. 11(a), general activity points 264, bike points 268, swim points 270 and remaining run/walk, race/walk, push, treadmill points 272 are added together to form total daily points 274, pursuant to the formula set forth in the remaining portion of FIG. 11(c) through 11(l), and repeated at length below:

8.1.1  Coef of Age =
       5–25 yrs., male .019 age + .51
       24–41 yrs., male − .001 age + 1.038
       42–60 yrs., male − .0073 age + 1.265
       61–100 yrs., male − .015 + 1.763
For female multiply all above by .93

8.1.2.6  Coef of Elevation =
         ≤ 28 days = .309 (elevation$^{.143}$)
         > 28 days = .658 (elevation$^{.051}$)

8.1.5 General Activities Daily Points =

$$\frac{.00001(time^{1.073})(RPE^{.9})wt \times coef\ act \times wt\ coef \times coef\ environment \times coef\ unusual\ act \times coef\ continuous\ act}{coef\ age(training\ VO_2^{-1.58})}$$

8.2 Biking Daily Points =

$$\frac{637.74^{.108}(training\ VO_2^{1.537})(weight^{1.009})wt\ coef \times coef\ environment \times coef\ unusual\ act \times coef\ continuous\ act}{coef\ age(time^{3.026})}$$

8.3.1.1.2 Coef of Internal =
          .536 coef recovery (repetition × interval distance$^{.037}$)

8.3.1.1.3 Swimming Daily Points =

$$\frac{16429(miles^{3.073})wt(training\ VO_2^{-.762})wt\ coef \times coef\ environment \times coef\ unusual\ act \times coef\ continuous\ act \times coef\ interval}{coef\ age[time^2 - 119(miles^{.97})(time^{1.03})(training\ VO_2^{-.739})]}$$

8.4.1.2 Coef Tempo = 1.47(miles$^{-.130}$)

8.4.1.3 Coef Race = 3.01(miles$^{-.355}$)

8.4.1.5 Run, Walk, Push, Race/walk, Treadmill, Daily Points =

-continued $$\frac{212.2(\text{miles}^{3.073})(\text{training VO}_2^{-.762})\text{coef act} \times \text{wt coef} \times}{\text{coef age}(\text{time}^2)}$$
$$\text{wt coef environment} \times \text{coef unusual act} \times \text{coef continuous}$$
$$\text{act} \times \text{coef fartlek} \times \text{coef tempo} \times \text{coef race} \times \text{coef interval}$$

Figure 12A:
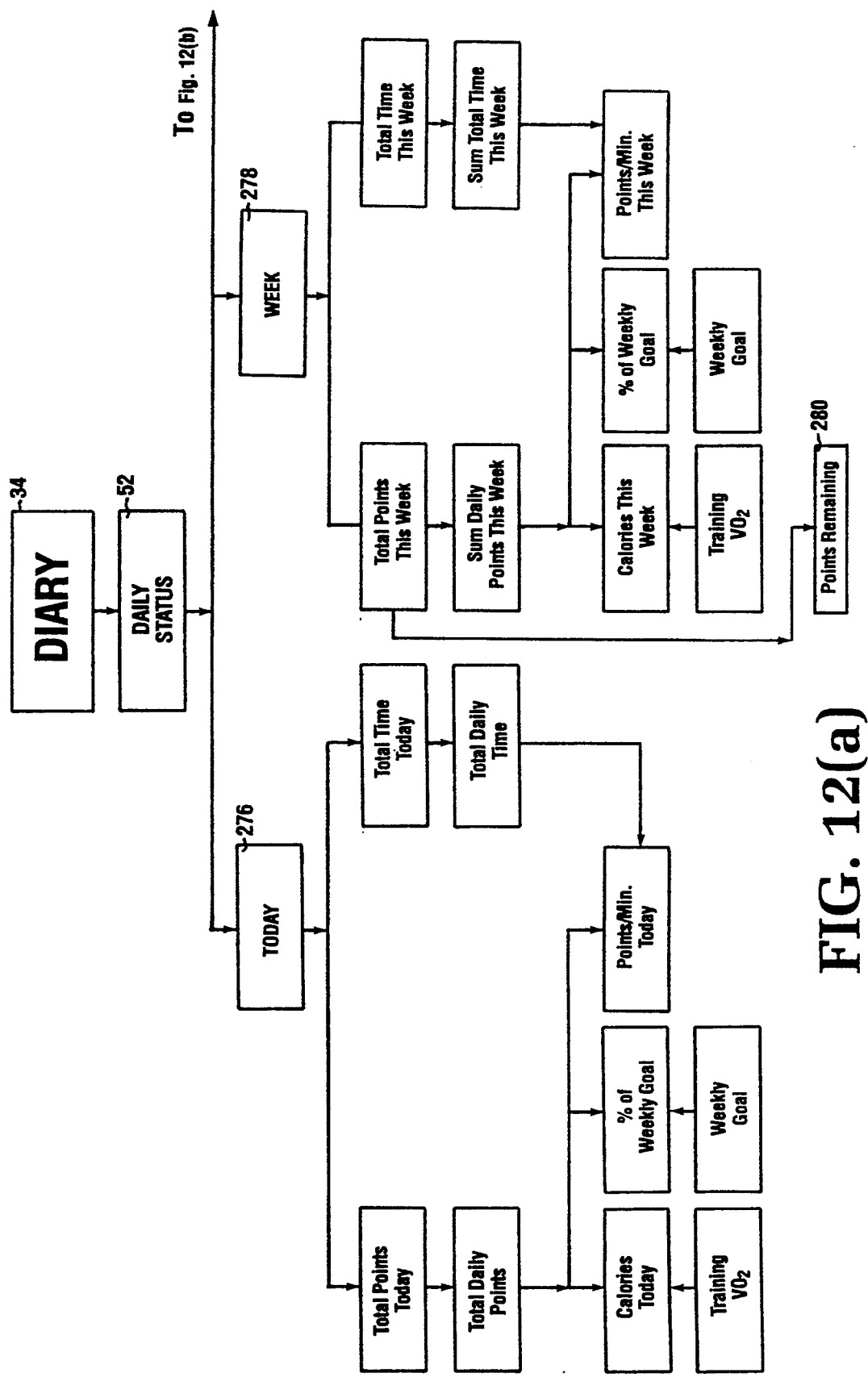
FIGS. 12(a) and 12(b) are an overview of the Daily Status, Section 9 of the Diary section of the resident software.
Figure 12B:
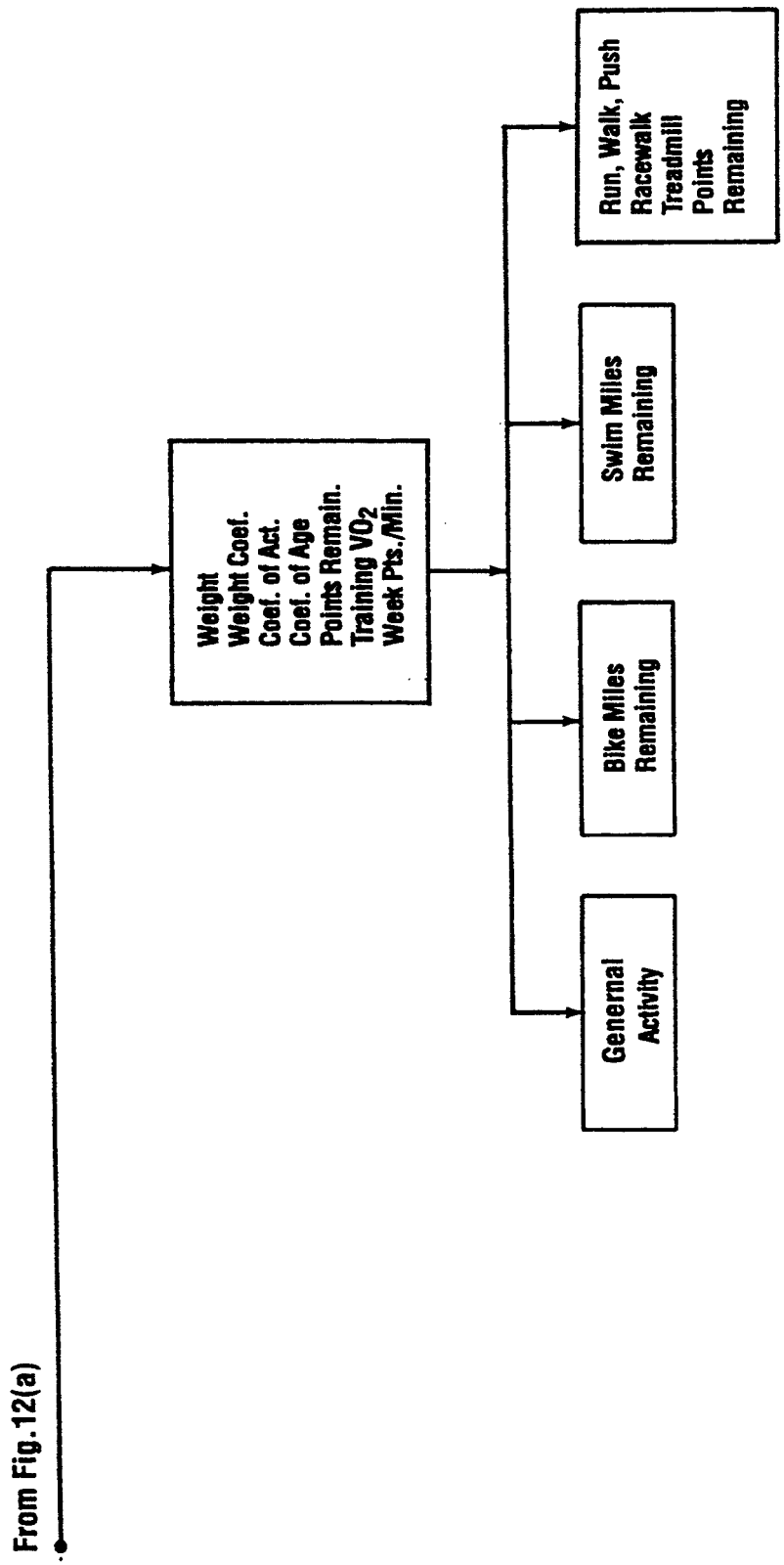
Figure 12:
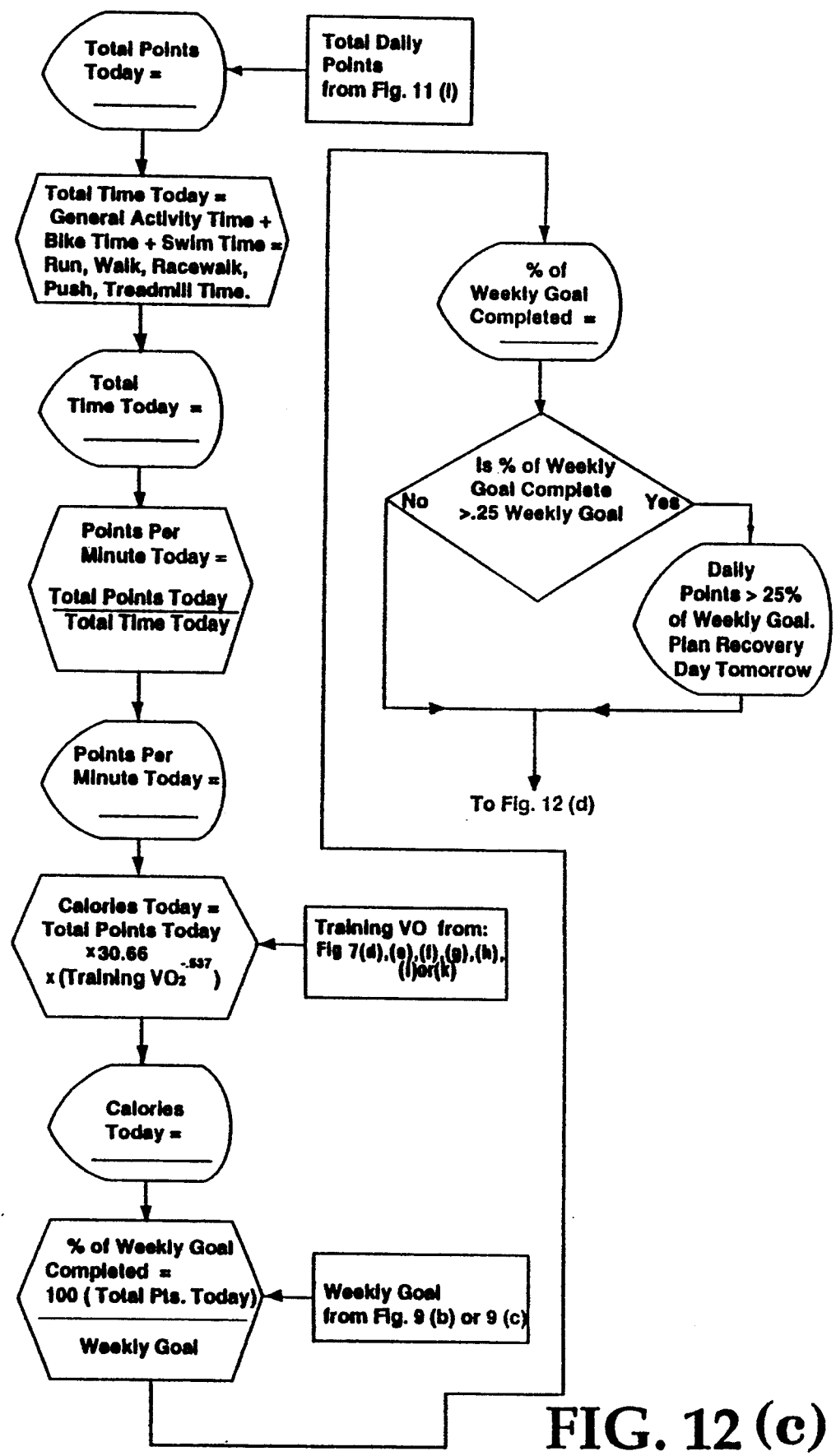
FIGS. 12(c) through 12(f) are flow charts of the Daily Status, Section 9 of the Diary section.
Figure 12:
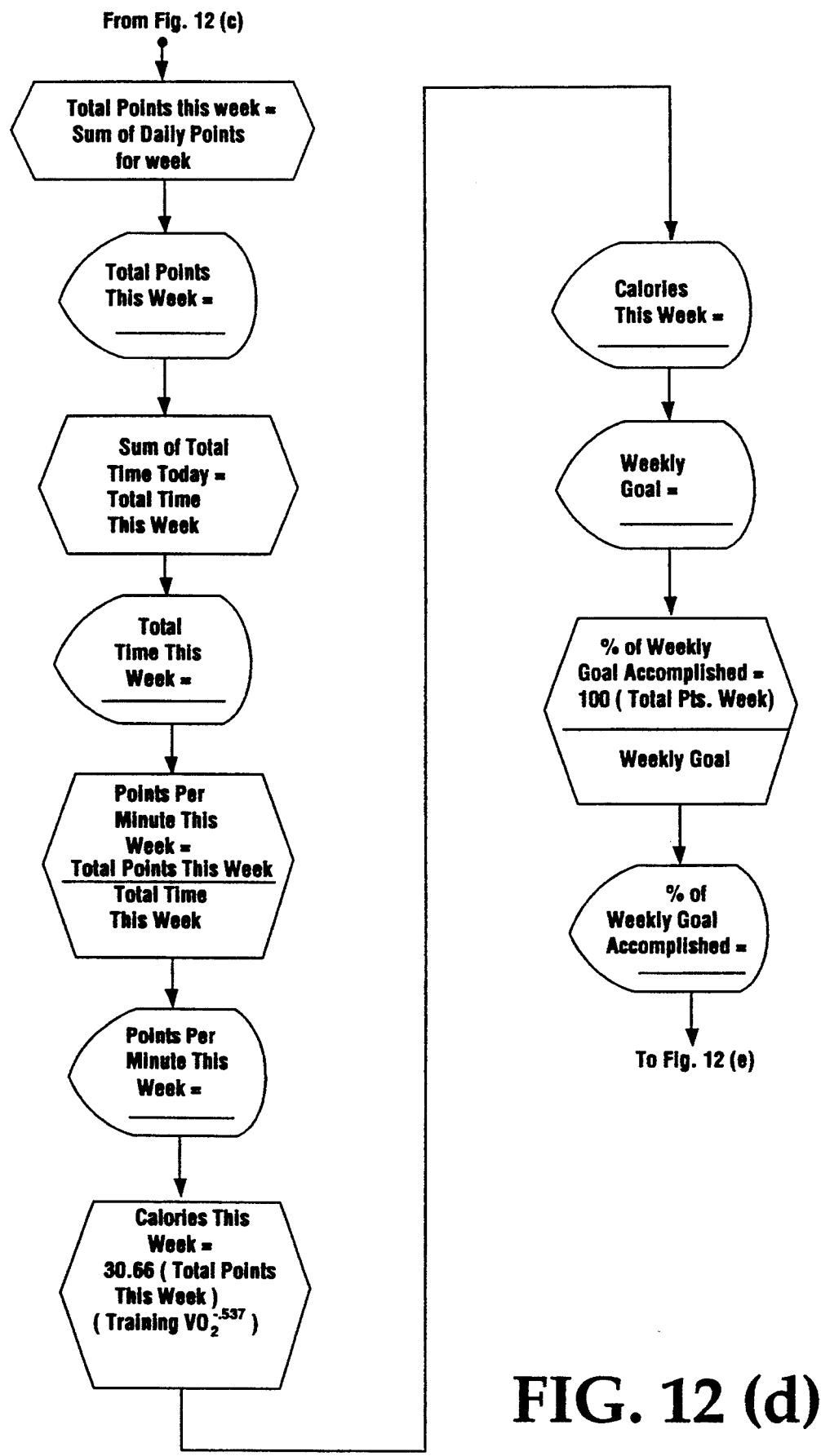
Figure 12:
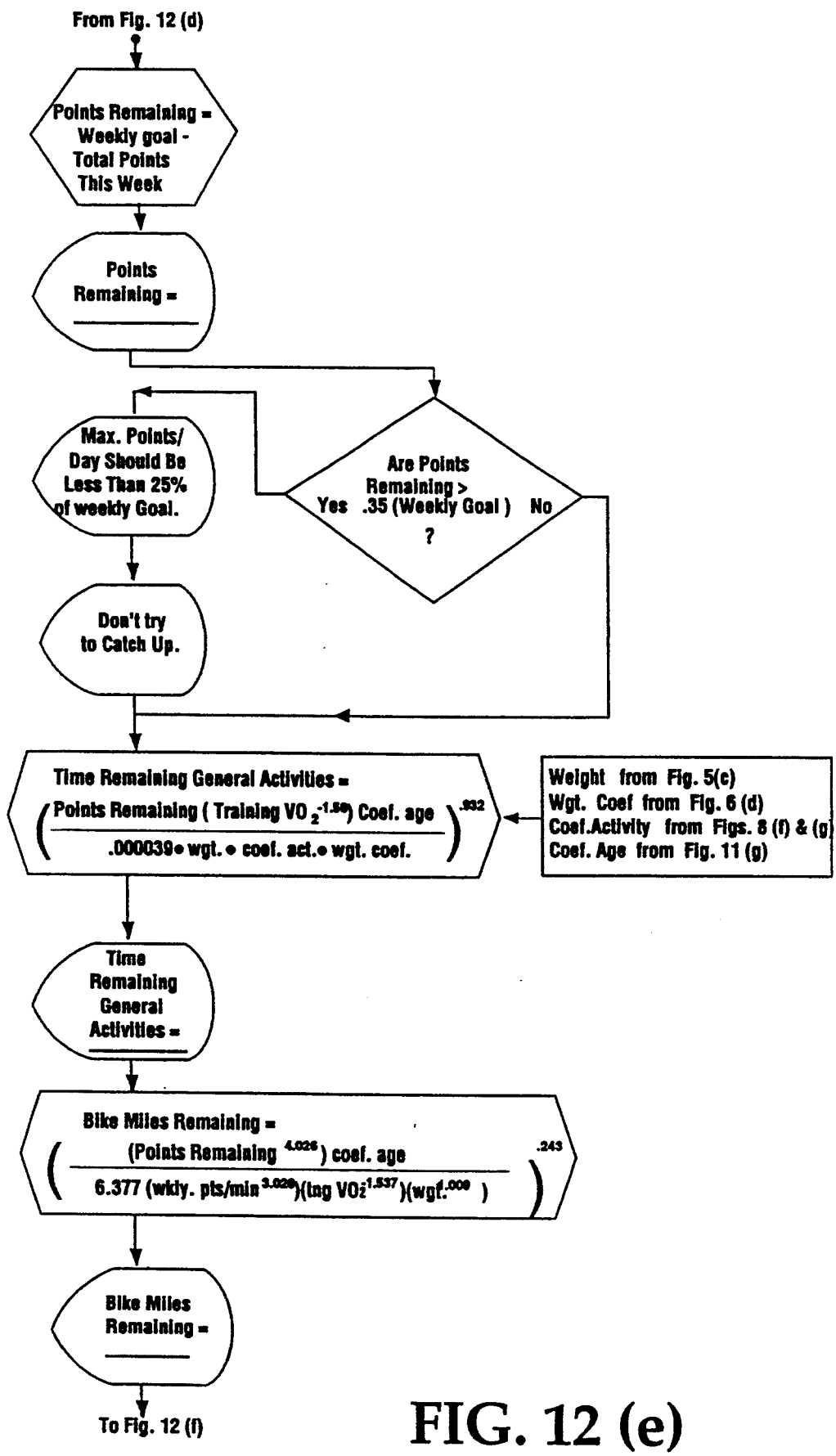
Figure 12F:
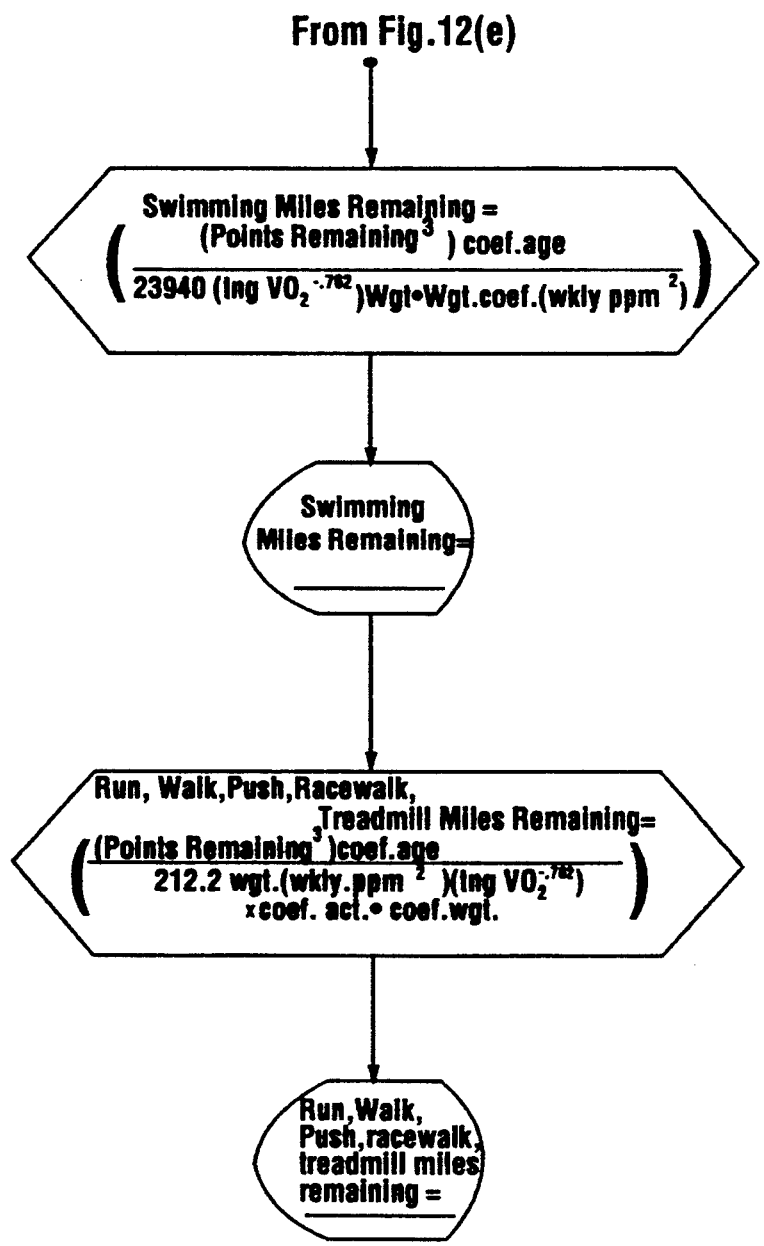

The information determined via the foregoing formulas is entered and compared under daily status 52, Section 9, set forth in FIGS. 12(a) through 12(f). Under daily status 52, the user is given an understanding of the comparison between the daily points reached against the weekly goals, set forth in box 276 in FIG. 12(a) and box 278 in FIG. 12(a), and the points remaining for the week are determined and set forth via box 280, and then broken down by individual activities selected from the group of 90 activities above, as shown in FIG. 12(b). At this point the user is also provided information with respect to overtraining. If more than 25% of the weekly goal is obtained in one day, the user is advised to take the next day easy.

The computations for the comparison between points achieved for the day and total points and miles and the like remaining are set forth in FIGS. 12(c) through 12(f), and this daily status determination is also set forth below:

9.4 Calories Today = 30.66 total daily points(training $VO_2^{-.537}$)

9.5 % Weekly Goal = 100 total points today/weekly goal 9.9 Calories This Week =

30.66 total points this week(training $VO_2^{-.537}$)

9.13.1 Time Remaining General Activity =

$$\left( \frac{\text{points remaining}(\text{training VO}_2^{-1.58}) \times \text{coef age}}{.000039 \times \text{weight} \times \text{coef act} \times \text{weight coef}} \right)^{.932}$$

9.14.1 Bike Miles Remaining =

$$\left[ \frac{\text{points remaining}^{4.026} \times \text{coef age}}{6.377(\text{weekly points per minute}^{3.026})(\text{training VO}_2^{1.537})(\text{wt}^{1.009})} \right]^{.243}$$

9.15.1 Swimming Miles Remaining =

$$\frac{\text{points remaining}^3 \times \text{coef age}}{23940(\text{training VO}_2^{-.762})\text{wt} \times \text{wt coef} \times (\text{wkly pts per min})^2}$$

9.16.1 Run, Walk, Push, Race/walk, Treadmill Miles $$\text{Remaining} = \frac{\text{points remaining}^3 \times \text{coef age}}{212.2 \text{ wt}(\text{weekly points per minute}^2)(\text{training VO}_2^{-.762})\text{contact} \times \text{coef wt}}$$

Figure 13A:
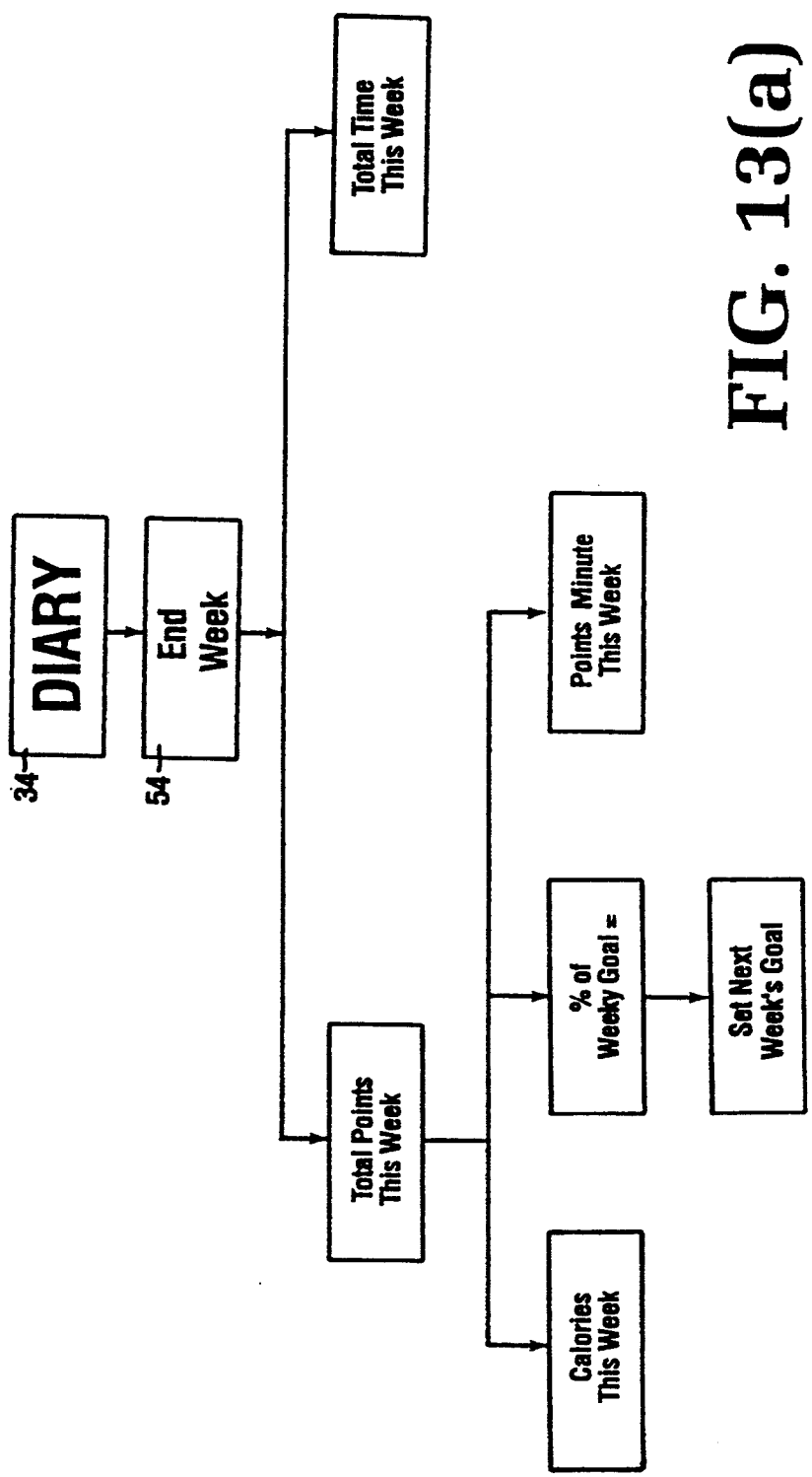
FIG. 13(a) is the End of Week, Section 10 of the Diary section of the resident software.
Figure 13:
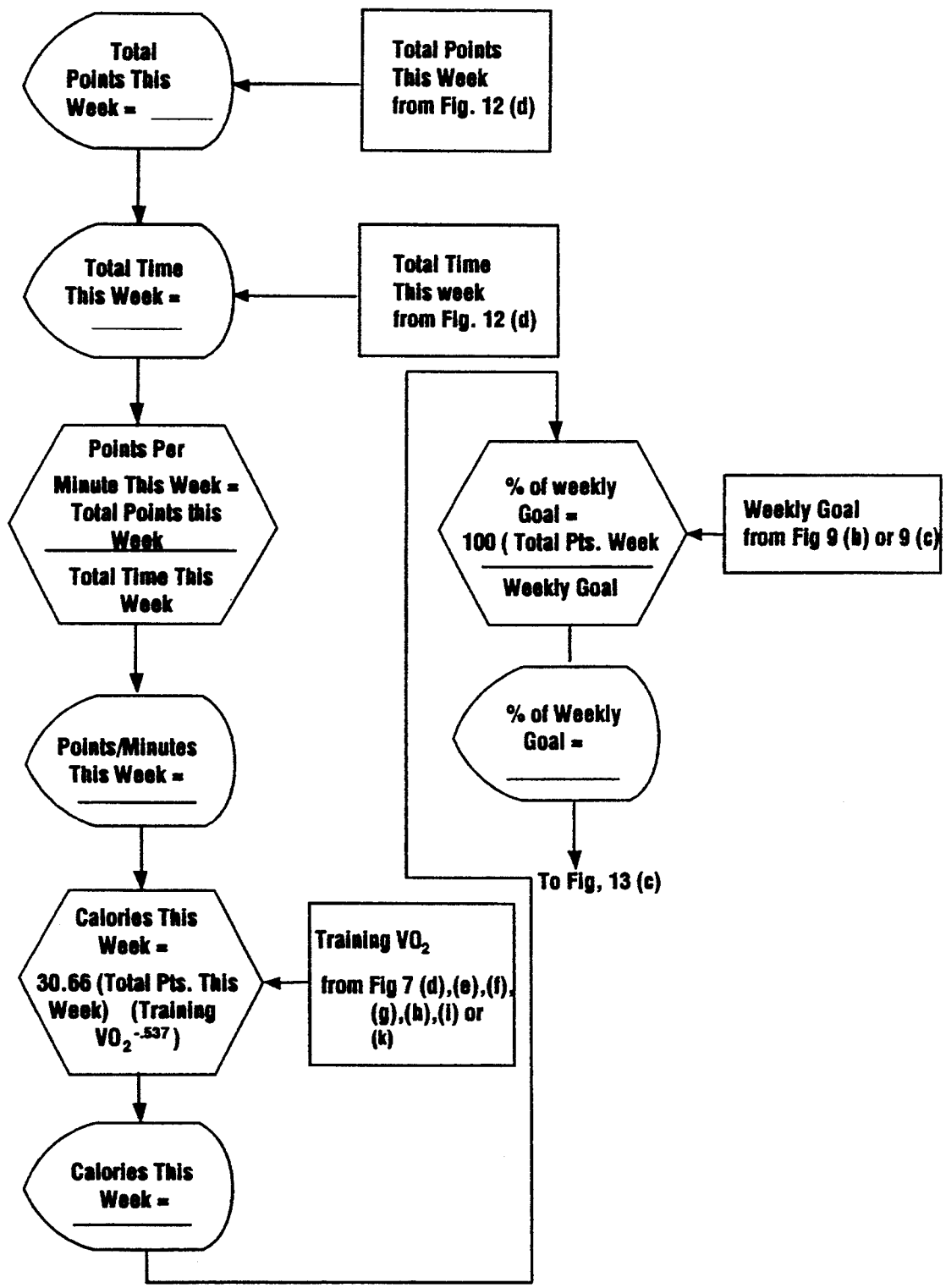
FIGS. 13(b) and 13(c) are flow charts of the End Weeks, Section 10 of the Diary section.
Figure 13:
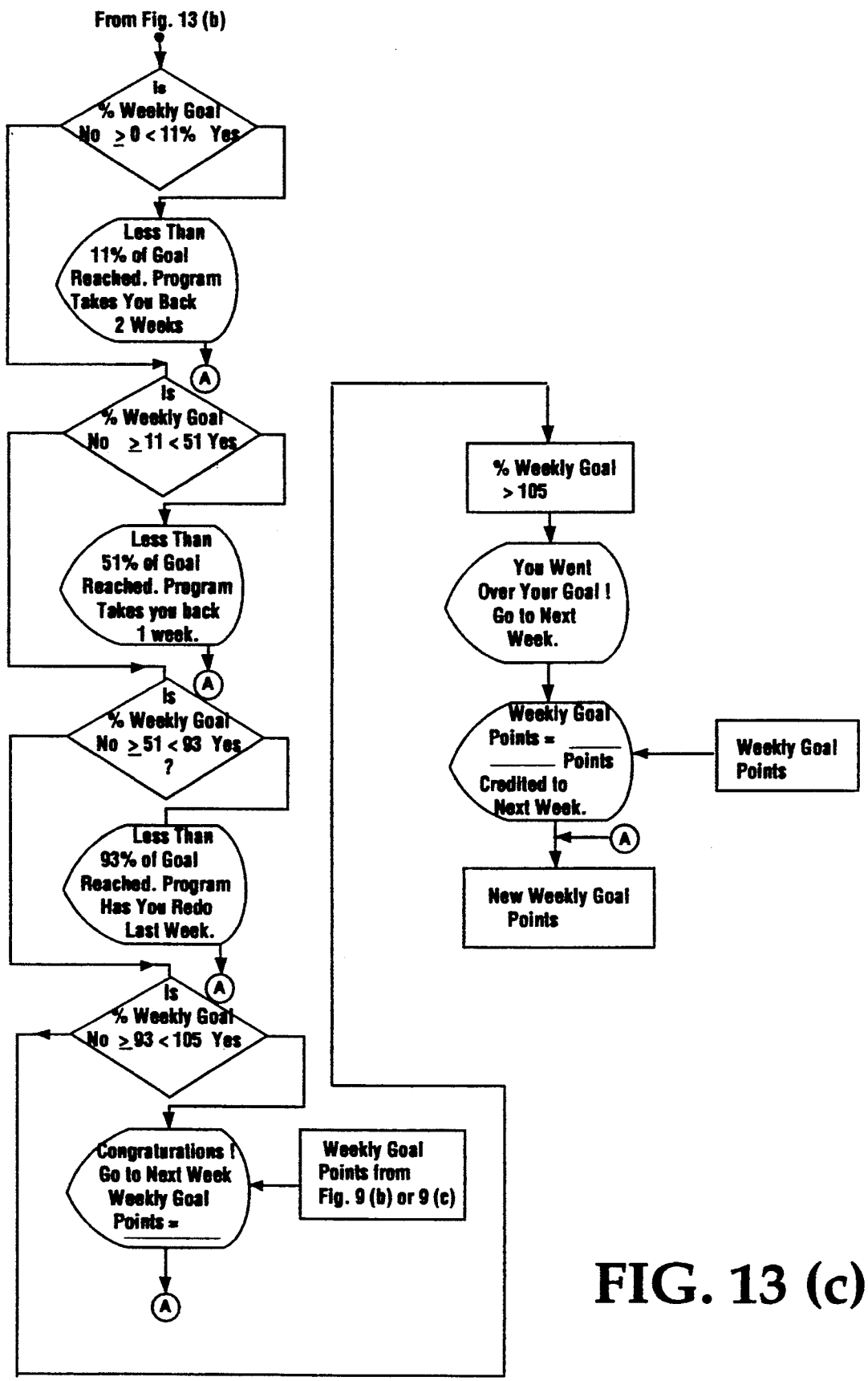

At the end of each week the weekly goals are reviewed and new goals set for the following week, based upon the total points achieved through the week, via diary 34 in entry and week 54, as set forth in FIGS. 13(a) through 13(c). The simple mathematical calculations are set forth in 13(b) and (c), and allow the user to know if the goals have been achieved, the total points reached for the week, total time for the week, the points per minutes for the week, the calories for the week and the overall percent of the weekly goals reached. Depending upon that percent of the weekly goal, user is given advise on what his weekly goal points should be for the following week. If the user has gone within approximately 5% of the user's weekly goal, the user goes on to the weekly points for the next week that his coach, or he, himself, or the program has suggested for him. If he goes under his goal, then the user is asked to go back or redo a certain week. If the user goes over his goal, the user is told to go on to the next week but his weekly goal points include the additional points he obtained from the week before.

Figure 14:
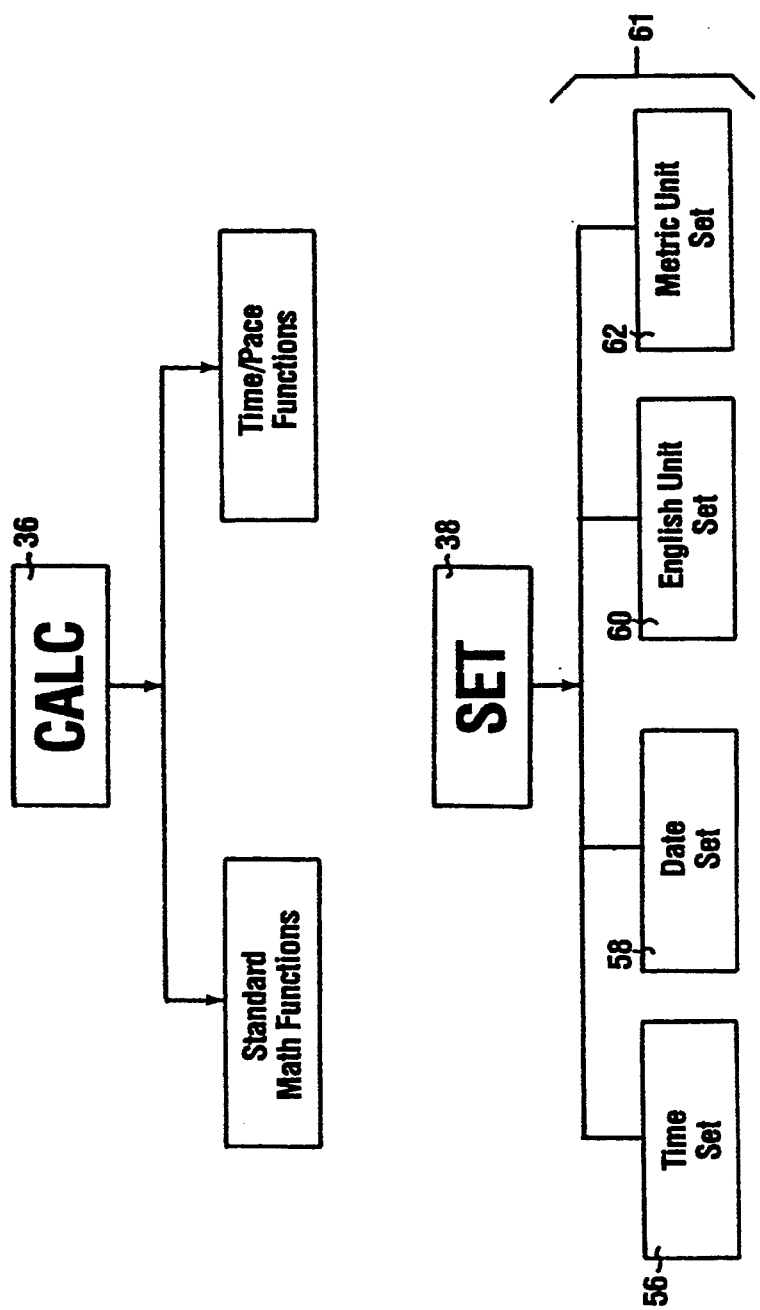
FIG. 14 is an overview of the Calculator, Section 11 of the resident software.

The last Sections 11, and 12 through 15, comprise calculator 36 and set 38 set forth in FIG. 14. As their names imply, calculator 36 allows time/pace function and standard math functions, and set 38 allows the user to set the time 56, the date 58, switch to English units 60 or the metric units 62.

It is to be understood that the foregoing preferred embodiment shall not be a limitation of the full scope of the invention, but are merely one method of practicing the invention. Other, further and different methods for practicing the invention are included within its scope.

I claim:

1. A method for scheduling and monitoring physical activities of an individual over an interval of time to tend to achieve progressively improved levels of fitness, while minimizing the individual's chance of injury and loss of fitness, the interval of time extending a plurality of multiday calendar periods, the method comprising the steps of:

(a) displaying on a display output of a data processing system a plurality of biographic/fitness-level prompts adapted to elicit biographic/fitness-level data from an individual for calculating a starting-fitness-level fitness-level point total for the individual, the starting-fitness-level fitness-level point total representing an estimate of an amount of physical activity which if performed by the individual over the course of a multiday calendar period would tend to improve the fitness level of the individual;

(b) calculating a sequence of fitness-level-progression point-total preliminary goals for the individual with the data-processing system from biographic/fitness-level data entered into the data-processing system in response to the biographic/fitness-level prompts, each of the sequence of fitness-level-progression point-total preliminary goals corresponding in turn to one of the multiday calendar periods, with the fitness-level-progression point-total preliminary goal corresponding to the initial multiday calendar period being the starting-fitness-level fitness-level point total, a fitness-level point-total goal for the initial multiday calendar period being defined to be the starting-fitness-level fitness-level point total, the fitness-level-progression point-total preliminary goals generally differing one from another and representing estimates of amounts of physical activity which if performed by the individual in the corresponding calendar periods in sequence would tend to result in progressively improved levels of fitness for the individual;

(c) for each of a plurality of days in a multiday calendar period, displaying on the display output of the data-processing system a plurality of daily-physical-activity-accomplishment prompts adapted to elicit daily-physical-activity accomplishment information from the individual, the daily-physicalactivity accomplishment information including an identification of each type of a plurality of types of physical activity engaged in during the day by the individual and, for each type of physical activity so identified, the time and intensity of the physical activity carried out during the day;

(d) for each of such plurality of days in such multiday calendar period, calculating a daily fitness-level point-total with the data-processing system from daily-physical-activity accomplishment information entered into the data-processing system in response to the daily-physical-activity accomplishment prompts for that day in accordance with predetermined fitness-benefit formulas, the daily fitness-level point total being representative of the cumulative physical benefits of the various specific types of physical activity engaged in by the individual for that day;

(e) for each of such plurality of days in such multiday calendar period, calculating with the data-processing system a fitness-level-points-remaining difference between a cumulative sum of the daily fitness-level point totals calculated for days to date during the multiday calendar period and a fitness-level-point-total goal defined for the calendar period and displaying fitness-level-points-remaining data on a display output of the data-processing system;

(f) for each of such plurality of days in such multiday calendar period, calculating comparison data between the daily fitness-level point total for that day and the fitness-level point-total goal for the calendar period with the data-processing system, and, in the event the comparison indicates that the daily fitness-level point total is excessive relative to a predetermined limit fraction of the fitness-level point-total goal, displaying a caution message on the display output of the data-processing system to minimize the individual's chance of injury and loss of fitness, the caution message cautioning against excessive activity by the individual;

(g) in correspondence with the conclusion of each multiday calendar period, generating with the data-processing system a new fitness-level point-total goal defined for the following multiday calendar period, the new fitness-level point-total goal being based on the fitness-level-progression point-total preliminary goal corresponding to such following multiday calendar period as possibly modified in accordance with an outcome of a comparison carried out in the data-processing system between a cumulative sum of the daily-fitness-level point totals for the multiday calendar period just concluded and the fitness-level point-total goal for such calendar period, so that in the event the cumulative sum of the daily-fitness-level point totals for the calendar period just concluded substantially equals or exceeds the fitness-level point-total goal for such calendar period, the new fitness-level point-total goal is defined to be a value which generally equals or exceeds the fitness-level-progression point-total preliminary goal for the following calendar period to tend to induce progressive improvement in the level of fitness of the individual, and, in the event the cumulative sum of the daily-fitness-level point totals for the calendar period just concluded is significantly lower than the fitness-level point-total goal for such calendar period, the new fitness-level point-total goal is defined to be a value which is generally lower than the fitness-level-progression point-total preliminary goal for the following multiday calendar period; and (h) displaying the new fitness-level point-total goal for the multiday calendar period on the display output of the data-processing system.

* * * * *